(12) United States Patent
Andrews et al.

(10) Patent No.: US 10,590,139 B2
(45) Date of Patent: Mar. 17, 2020

(54) METHOD OF TREATMENT USING SUBSTITUTED IMIDAZO[1,2B]PYRIDAZINE COMPOUNDS

(71) Applicant: Array BioPharma Inc., Boulder, CO (US)

(72) Inventors: Steven W. Andrews, Boulder, CO (US); Julia Haas, Boulder, CO (US); Yutong Jiang, Boulder, CO (US); Gan Zhang, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 16/025,281

(22) Filed: Jul. 2, 2018

(65) Prior Publication Data
US 2019/0169193 A1    Jun. 6, 2019

Related U.S. Application Data

(63) Continuation of application No. 14/984,353, filed on Dec. 30, 2015, now Pat. No. 10,011,604, which is a continuation of application No. 13/614,968, filed on Sep. 13, 2012, now Pat. No. 9,227,975, which is a continuation of application No. 13/063,894, filed as application No. PCT/US2009/057729 on Sep. 21, 2009, now Pat. No. 8,450,322.

(60) Provisional application No. 61/099,030, filed on Sep. 22, 2008.

(51) Int. Cl.
| C07D 487/04 | (2006.01) |
| C07D 471/04 | (2006.01) |
| C07C 51/41 | (2006.01) |
| C07C 53/18 | (2006.01) |
| C07D 519/00 | (2006.01) |
| A61K 31/5025 | (2006.01) |
| A61K 31/5377 | (2006.01) |
| A61K 31/541 | (2006.01) |

(52) U.S. Cl.
CPC ........ *C07D 487/04* (2013.01); *A61K 31/5025* (2013.01); *A61K 31/5377* (2013.01); *A61K 31/541* (2013.01); *C07C 51/412* (2013.01); *C07C 53/18* (2013.01); *C07D 471/04* (2013.01); *C07D 519/00* (2013.01); *Y02A 50/414* (2018.01)

(58) Field of Classification Search
CPC .................................................. C07D 487/04
See application file for complete search history.

(56) References Cited

U.S. PATENT DOCUMENTS

| 5,430,021 A | 7/1995 | Rudnic et al. |
| 5,760,068 A | 6/1998 | Talley et al. |
| 5,844,092 A | 12/1998 | Presta et al. |
| 5,877,016 A | 3/1999 | Presta et al. |
| 5,910,574 A | 6/1999 | Presta et al. |
| 6,025,166 A | 2/2000 | Presta et al. |
| 6,027,927 A | 2/2000 | Presta et al. |
| 6,153,189 A | 11/2000 | Presta et al. |
| 6,534,085 B1 | 3/2003 | Zeligs |
| 7,384,632 B2 | 6/2008 | Devaux et al. |
| 7,491,794 B2 | 2/2009 | Blatt et al. |
| 7,514,446 B2 | 4/2009 | Davis-Ward et al. |
| 7,550,470 B2 | 6/2009 | Fraley |
| 7,612,067 B2 | 11/2009 | Barbosa et al. |
| 7,615,383 B2 | 11/2009 | Devaux et al. |
| 7,863,289 B2 | 1/2011 | Spevak et al. |
| 8,026,247 B2 | 9/2011 | Bold et al. |
| 8,106,167 B2 | 1/2012 | Wild, Jr. et al. |
| 8,114,989 B2 | 2/2012 | Wang et al. |
| 8,119,592 B2 | 2/2012 | Beigelman et al. |
| 8,148,107 B2 | 4/2012 | Macdonald et al. |
| 8,299,021 B2 | 10/2012 | Blatt et al. |
| 8,299,057 B2 | 10/2012 | Lombardi Borgia et al. |
| 8,338,417 B2 | 12/2012 | Li et al. |
| 8,399,442 B2 | 3/2013 | Berdini et al. |

(Continued)

FOREIGN PATENT DOCUMENTS

| AU | 2015/101722 | 5/2016 |
| CN | 1938311 | 3/2007 |

(Continued)

OTHER PUBLICATIONS

McMahon et al. (2000).*

(Continued)

*Primary Examiner* — Paul V Ward
(74) *Attorney, Agent, or Firm* — Meunier Carlin & Curfman LLC

(57) ABSTRACT

Methods for treating a disease or disorder selected from pain, cancer, inflammation, neurodegenerative disease, *Typanosoma cruzi* infection and osteolytic disease in a mammal, which comprise administering to said mammal a therapeutically effective amount of a compound of Formula I

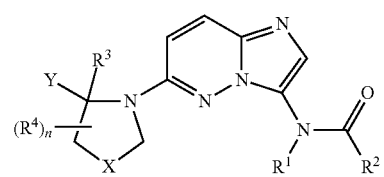

in which $R^1$, $R^2$, $R^3$, $R^4$, X, Y and n have the meanings given in the specification.

22 Claims, No Drawings

(56) References Cited

U.S. PATENT DOCUMENTS

| | | |
|---|---|---|
| 8,450,322 B2 | 5/2013 | Andrews et al. |
| 8,501,756 B2 | 8/2013 | Artman, III et al. |
| 8,513,263 B2 | 8/2013 | Haas et al. |
| 8,552,002 B2 | 10/2013 | Ding et al. |
| 8,568,998 B2 | 10/2013 | Mani |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,691,221 B2 | 4/2014 | Pavone et al. |
| 8,791,123 B2 | 7/2014 | Allen et al. |
| 8,815,901 B2 | 8/2014 | Furet et al. |
| 8,865,698 B2 | 10/2014 | Haas et al. |
| 8,911,734 B2 | 12/2014 | Latham et al. |
| 8,912,194 B2 | 12/2014 | Ciomei |
| 8,912,204 B2 | 12/2014 | Ibrahim et al. |
| 8,933,084 B2 | 1/2015 | Andrews |
| 8,937,071 B2 | 1/2015 | Eidam et al. |
| 8,946,226 B2 | 2/2015 | Ciomei et al. |
| 9,006,256 B2 | 4/2015 | Matsui |
| 9,035,063 B2 | 5/2015 | Eidam et al. |
| 9,102,671 B2 | 8/2015 | Molteni et al. |
| 9,127,013 B2 | 9/2015 | Haas et al. |
| 9,187,489 B2 | 11/2015 | Takeda et al. |
| 9,227,975 B2 | 1/2016 | Andrews et al. |
| 9,242,977 B2 | 1/2016 | Takeuchi et al. |
| 9,260,437 B2 | 2/2016 | Ibrahim et al. |
| 9,273,051 B2 | 3/2016 | Chen et al. |
| 9,346,788 B2 | 5/2016 | Wu et al. |
| 9,447,104 B2 | 9/2016 | Haas et al. |
| 9,447,135 B2 | 9/2016 | Rohr et al. |
| 9,469,876 B2 | 10/2016 | Kuslich |
| 9,493,476 B2 | 11/2016 | Andrews et al. |
| 9,511,050 B2 | 12/2016 | Toretsky et al. |
| 9,670,207 B2 | 6/2017 | Sasmal et al. |
| 9,676,783 B2 | 6/2017 | Haas et al. |
| 9,682,979 B2 | 6/2017 | Allen et al. |
| 9,701,681 B2 | 6/2017 | Kim et al. |
| 9,718,822 B2 | 8/2017 | Andrews et al. |
| 9,750,744 B2 | 9/2017 | Andrews et al. |
| 9,782,400 B2 | 10/2017 | Yao et al. |
| 9,782,414 B2 | 10/2017 | Arrigo et al. |
| 9,782,415 B2 | 10/2017 | Allen et al. |
| 9,795,611 B2 | 10/2017 | Andrews et al. |
| 9,796,723 B2 | 10/2017 | Andrews et al. |
| 9,796,724 B2 | 10/2017 | Allen et al. |
| 9,840,519 B2 | 12/2017 | Andrews et al. |
| 9,902,741 B2 | 2/2018 | Andrews et al. |
| 10,005,783 B2 | 6/2018 | Haas et al. |
| 10,011,604 B2 | 7/2018 | Andrews et al. |
| 10,045,991 B2 | 8/2018 | Cox et al. |
| 10,047,097 B2 | 8/2018 | Haas et al. |
| 10,137,127 B2 | 11/2018 | Reynolds et al. |
| 10,172,861 B2 | 1/2019 | Arrigo et al. |
| 2005/0209195 A1 | 9/2005 | Menta et al. |
| 2006/0094699 A1 | 5/2006 | Kampen et al. |
| 2006/0128725 A1 | 6/2006 | Guzi |
| 2006/0211696 A1 | 9/2006 | Hibi et al. |
| 2007/0025540 A1 | 2/2007 | Travis |
| 2007/0042941 A1 | 2/2007 | Hirashima et al. |
| 2007/0082900 A1 | 4/2007 | Guzi et al. |
| 2007/0082902 A1 | 4/2007 | Paruch et al. |
| 2007/0184117 A1 | 8/2007 | Gregory et al. |
| 2007/0225270 A1 | 9/2007 | Guzi et al. |
| 2007/0281951 A1 | 12/2007 | Guzi et al. |
| 2009/0041717 A1 | 2/2009 | Macdonald et al. |
| 2009/0099167 A1 | 4/2009 | Bold et al. |
| 2009/0130229 A1 | 5/2009 | Lanzi et al. |
| 2009/0227556 A1 | 9/2009 | Obaishi |
| 2010/0029633 A1 | 2/2010 | Allen et al. |
| 2010/0152219 A1 | 6/2010 | Block et al. |
| 2010/0297115 A1 | 11/2010 | Blaustein |
| 2010/0324065 A1 | 12/2010 | Ibrahim et al. |
| 2011/0053934 A1 | 3/2011 | Angell et al. |
| 2011/0166122 A1 | 7/2011 | Andrews et al. |
| 2011/0195948 A1 | 8/2011 | Haas et al. |
| 2011/0268725 A1 | 11/2011 | Shelton |
| 2011/0301157 A1 | 12/2011 | Bold et al. |
| 2012/0108568 A1 | 5/2012 | Allen et al. |
| 2013/0029925 A1 | 1/2013 | Vandier et al. |
| 2013/0203776 A1 | 8/2013 | Andrews et al. |
| 2013/0217662 A1 | 8/2013 | Andrews et al. |
| 2014/0121239 A1 | 5/2014 | Aftab |
| 2014/0194403 A1 | 7/2014 | Haas et al. |
| 2014/0227287 A1 | 8/2014 | Kamohara et al. |
| 2014/0243332 A1 | 8/2014 | Davare |
| 2014/0315199 A1 | 10/2014 | Rhodes et al. |
| 2014/0336236 A1 | 11/2014 | Cronin et al. |
| 2015/0005499 A1 | 1/2015 | Haas et al. |
| 2015/0018336 A1 | 1/2015 | Chen et al. |
| 2015/0031667 A1 | 1/2015 | Allen et al. |
| 2015/0051222 A1 | 2/2015 | Barbugian et al. |
| 2015/0073036 A1 | 3/2015 | Hawryluk et al. |
| 2015/0166564 A1 | 6/2015 | Allen et al. |
| 2015/0218132 A1 | 8/2015 | Wu |
| 2015/0218652 A1 | 8/2015 | Doebele et al. |
| 2015/0283132 A1 | 10/2015 | Lim et al. |
| 2015/0306086 A1 | 10/2015 | Wilcoxen |
| 2015/0315657 A1 | 11/2015 | Rhodes et al. |
| 2015/0336970 A1 | 11/2015 | Andrews et al. |
| 2016/0000783 A1 | 1/2016 | Takeuchi et al. |
| 2016/0009785 A1 | 1/2016 | Lipson et al. |
| 2016/0010068 A1 | 1/2016 | Bastian |
| 2016/0032396 A1 | 2/2016 | Diehn |
| 2016/0032404 A1 | 2/2016 | Schweighofer et al. |
| 2016/0108123 A1 | 4/2016 | Freeman et al. |
| 2016/0108380 A1 | 4/2016 | Iavarone et al. |
| 2016/0137654 A1 | 5/2016 | Arrigo et al. |
| 2016/0145237 A1 | 5/2016 | Hu et al. |
| 2016/0228441 A1 | 8/2016 | Haas et al. |
| 2016/0251357 A1 | 9/2016 | Andrews et al. |
| 2016/0263086 A1 | 9/2016 | Toretsky |
| 2016/0272725 A1 | 9/2016 | Stransky et al. |
| 2016/0305943 A1 | 10/2016 | Takeuchi et al. |
| 2016/0367547 A1 | 12/2016 | Yao et al. |
| 2017/0107232 A1 | 4/2017 | Andrews et al. |
| 2017/0112842 A1 | 4/2017 | Andrews et al. |
| 2017/0112849 A1 | 4/2017 | Andrews et al. |
| 2017/0114059 A1 | 4/2017 | Andrews et al. |
| 2017/0114067 A1 | 4/2017 | Haas et al. |
| 2017/0114068 A1 | 4/2017 | Andrews et al. |
| 2017/0114069 A1 | 4/2017 | Allen et al. |
| 2017/0114415 A1 | 4/2017 | Doebele et al. |
| 2017/0119770 A1 | 5/2017 | Allen et al. |
| 2017/0165267 A1 | 6/2017 | Arrigo et al. |
| 2017/0224662 A1 | 8/2017 | Motheram et al. |
| 2017/0260589 A1 | 9/2017 | Nanda et al. |
| 2017/0281632 A1 | 10/2017 | Cox et al. |
| 2017/0283435 A1 | 10/2017 | Andrews et al. |
| 2017/0296544 A1 | 10/2017 | Reynolds et al. |
| 2018/0021342 A1 | 1/2018 | Arrigo et al. |
| 2018/0030548 A1 | 2/2018 | Nanda et al. |
| 2018/0030549 A1 | 2/2018 | Nanda et al. |
| 2018/0119228 A1 | 5/2018 | Nanda et al. |
| 2018/0127427 A1 | 5/2018 | Haas et al. |
| 2018/0133222 A1 | 5/2018 | Cox et al. |
| 2018/0140604 A1 | 5/2018 | Tuch et al. |
| 2018/0142306 A1 | 5/2018 | Nanda et al. |
| 2018/0207162 A1 | 7/2018 | Arrigo et al. |
| 2018/0263984 A1 | 9/2018 | Allen et al. |
| 2019/0031684 A1 | 1/2019 | Andrews |
| 2019/0076436 A1 | 3/2019 | Andrews |
| 2019/0076437 A1 | 3/2019 | Andrews |
| 2019/0151322 A1 | 5/2019 | Andrews et al. |
| 2019/0211017 A1 | 7/2019 | Haas et al. |
| 2019/0216814 A1 | 7/2019 | Reynolds et al. |
| 2019/0218222 A1 | 7/2019 | Reynolds et al. |
| 2019/0247398 A1 | 8/2019 | Zhao et al. |

FOREIGN PATENT DOCUMENTS

| | | |
|---|---|---|
| CN | 101119996 | 2/2008 |
| CN | 101208093 | 6/2008 |
| EA | 009517 | 2/2008 |

(56) References Cited

FOREIGN PATENT DOCUMENTS

| | | |
|---|---|---|
| EP | 0810217 | 12/1997 |
| EP | 1873157 | 1/2008 |
| EP | 1948633 | 8/2011 |
| EP | 2986736 | 2/2016 |
| EP | 2558490 | 12/2016 |
| EP | 3266795 | 10/2018 |
| JP | 2004-087707 | 3/2004 |
| JP | 2004-277337 | 10/2004 |
| JP | 2005-008581 | 1/2005 |
| JP | 2006-518364 | 8/2006 |
| JP | 2007-504276 | 3/2007 |
| JP | 2007-514712 | 6/2007 |
| JP | 2008-523034 | 7/2008 |
| JP | 2008-285464 | 11/2008 |
| JP | 2009-502734 | 1/2009 |
| JP | 2009-511487 | 3/2009 |
| JP | 2009-541242 | 11/2009 |
| JP | 2010-508315 | 3/2010 |
| JP | 2011-520887 | 7/2011 |
| JP | 2012-506446 | 3/2012 |
| JP | 2012-507569 | 3/2012 |
| JP | 2014-082984 | 5/2014 |
| WO | WO 1998/49167 | 11/1998 |
| WO | WO 2003/080064 | 10/2003 |
| WO | WO 2004/022561 | 3/2004 |
| WO | WO 2004/052286 | 6/2004 |
| WO | WO 2004/052315 | 6/2004 |
| WO | WO 2004/074290 | 9/2004 |
| WO | WO 2004/082458 | 9/2004 |
| WO | WO 2004/087707 | 10/2004 |
| WO | WO 2004/089415 | 10/2004 |
| WO | WO 2004/089471 | 10/2004 |
| WO | WO 2005/049033 | 6/2005 |
| WO | WO 2006/052913 | 5/2006 |
| WO | WO 2006/087538 | 8/2006 |
| WO | WO 2006/115452 | 11/2006 |
| WO | WO 2006/123113 | 11/2006 |
| WO | WO 2006/131051 | 12/2006 |
| WO | WO 2006/131952 | 12/2006 |
| WO | WO 2007/013673 | 2/2007 |
| WO | WO 2007/015824 | 2/2007 |
| WO | WO 2007/022999 | 3/2007 |
| WO | WO 2007/024680 | 3/2007 |
| WO | WO 2007/025090 | 3/2007 |
| WO | WO 2007/025540 | 3/2007 |
| WO | WO 2007/038314 | 4/2007 |
| WO | WO 2007/044410 | 4/2007 |
| WO | WO 2007/044449 | 4/2007 |
| WO | WO 2007/044893 | 4/2007 |
| WO | WO 2007/048066 | 4/2007 |
| WO | WO 2007/062805 | 6/2007 |
| WO | WO 2007/084815 | 7/2007 |
| WO | WO 2007/102679 | 9/2007 |
| WO | WO 2007/103308 | 9/2007 |
| WO | WO 2007/113000 | 10/2007 |
| WO | WO 2007/129161 | 11/2007 |
| WO | WO 2008/016131 | 2/2008 |
| WO | WO 2008/021924 | 2/2008 |
| WO | WO 2008/030579 | 3/2008 |
| WO | WO 2008/037477 | 4/2008 |
| WO | WO 2008/052734 | 5/2008 |
| WO | WO 2008/058126 | 5/2008 |
| WO | WO 2008/115974 | 9/2008 |
| WO | WO 2008/116898 | 10/2008 |
| WO | WO 2008/155421 | 12/2008 |
| WO | WO 2009/013126 | 1/2009 |
| WO | WO 2009/052145 | 4/2009 |
| WO | WO 2009/053442 | 4/2009 |
| WO | WO 2009/060197 | 5/2009 |
| WO | WO 2009/092049 | 7/2009 |
| WO | WO 2009/140128 | 11/2009 |
| WO | WO 2010/012733 | 2/2010 |
| WO | WO 2010/033941 | 4/2010 |
| WO | WO 2010/048314 | 4/2010 |
| WO | WO 2010/051549 | 5/2010 |
| WO | WO 2010/058006 | 5/2010 |
| WO | WO 2010/093928 | 8/2010 |
| WO | WO 2011/006074 | 1/2011 |
| WO | WO 2011/130340 | 10/2011 |
| WO | WO 2011/133637 | 10/2011 |
| WO | WO 2011/146336 | 11/2011 |
| WO | WO 2012/024650 | 2/2012 |
| WO | WO 2012/034091 | 3/2012 |
| WO | WO 2012/034095 | 3/2012 |
| WO | WO 2012/116217 | 8/2012 |
| WO | WO 2012/158413 | 11/2012 |
| WO | WO 2013/059740 | 4/2013 |
| WO | WO 2013/074518 | 5/2013 |
| WO | WO 2013/174876 | 11/2013 |
| WO | WO 2013/183578 | 12/2013 |
| WO | WO 2014/036387 | 3/2014 |
| WO | WO 2014/047572 | 3/2014 |
| WO | WO 2014/078322 | 5/2014 |
| WO | WO 2014/078323 | 5/2014 |
| WO | WO 2014/078325 | 5/2014 |
| WO | WO 2014/078328 | 5/2014 |
| WO | WO 2014/078331 | 5/2014 |
| WO | WO 2014/078372 | 5/2014 |
| WO | WO 2014/078408 | 5/2014 |
| WO | WO 2014/078417 | 5/2014 |
| WO | WO 2014/078454 | 5/2014 |
| WO | WO 2014/083567 | 6/2014 |
| WO | WO 2014/130975 | 8/2014 |
| WO | WO 2014/134096 | 9/2014 |
| WO | WO 2014/152777 | 9/2014 |
| WO | WO 2015/017533 | 2/2015 |
| WO | WO 2015/064621 | 5/2015 |
| WO | WO 2015/112806 | 7/2015 |
| WO | WO 2015/124697 | 8/2015 |
| WO | WO 2015/175788 | 11/2015 |
| WO | WO 2015/183837 | 12/2015 |
| WO | WO 2016/027754 | 2/2016 |
| WO | WO 2016/097869 | 6/2016 |
| WO | WO 2016/187508 | 11/2016 |
| WO | WO 2016/196141 | 12/2016 |
| WO | WO 2016/196671 | 12/2016 |
| WO | WO 2017/001491 | 1/2017 |
| WO | WO 2017/004342 | 1/2017 |
| WO | WO 2017/075107 | 5/2017 |
| WO | WO 2017/155018 | 9/2017 |
| WO | 2017/184597 | 10/2017 |
| WO | 2017/201156 | 11/2017 |
| WO | WO 2017/201241 | 11/2017 |
| WO | WO 2018/081417 | 5/2018 |
| WO | 2018/170381 | 9/2018 |
| WO | WO 2019/005796 | 1/2019 |
| WO | 2019/084285 | 5/2019 |

OTHER PUBLICATIONS

Pinedo et al. (2000).*
Adriaenssens et al., "Nerve Growth Factor is a Potential Therapeutic Target in Breast Cancer," Cancer Res., 2008, 68(2):346-351.
Agaram et al., "Recurrent NTRK1 gene fusions define a novel subset of locally aggressive lipofibromatosis-like neural tumors," Am. J. Surg. Pathol, Oct. 2016, 40(10): 1407-1416.
Agaram, et al., "Abstract 33: NTRK1 Associated Gene Fusions in Pediatric Fibroblastic Myofibroglastic Neoplasms: A Molecular Staudy of 58 Cases," 105th Annual Meeting of the United States and Canadian Academy of Pathology, 2016, 12A.
Aisner et al., "ROS1 and ALK fusions in colorectal cancer, with evidence of intratumoral heterogeneity for molecular drivers.", Mal. Cancer Res., 12(1): 111-8, 2014.
Albaugh et al., "Discovery of GNF-5837, a Selective TRK Inhibitor with Efficacy in Rodent Cancer Tumor Models," ACS Medicinal Chemistry Letters, 2012, 3(2):140-145.
Ali et al., "Comprehensive Genomic Profiling Identifies a Subset of Crizotinib-Responsive ALK-Rearranged Non-Small Cell Lung Cancer Not Detected by Fluorescence In Situ Hybridization.", Oncologist, 21(6): 762-70, 2016.
Alvarez-Breckenridge et al., "Clinical and radiographic response following targeting of BCAN-NTRK1 fusion in glioneuronal tumor,"

(56) References Cited

OTHER PUBLICATIONS

NPJ Precision Oncology, Mar. 2017, 5 pages.
Amatu et al., "NTRK gene fusions as novel targets of cancer therapy across multiple tumour types", ESMD Open, 1-9, 2016.
American Cancer Society, "Sarcoma: Adult Soft Tissue Cancer," Jun. 2014, retrieved on Apr. 27, 2015, http://www.cancer.org/cancer/sarcoma-adultsofttissuecancer/detailedguide/sarcoma-adult-soft-tissue-cancer-key-statistics, 45 pages.
Andreason et al., "ETV6 Gene Rearrangements Characterize a Morphologically Distinct Subset of Sinonasal Low-grade Non-intestinal-type Adenocarcinoma," Am. J. Surg. Pathol, Nov. 2017, 41(11):1552-1560.
Arce et al., "Secretory cacinoma of the breast containing the ETV6-NTRK3 fusion gene in a male: case report and review of the literature," World J. Surg. Oncol, Jun. 2005, 3:35.
Ardini et al., "The TPM3-NTRK1 rearrangement is a recurring event in colorectal carcinoma and is associated with tumor sensitivity to TRKA kinase inhibition," Mol. Oncol. 8(8): 1495-1507, 2014.
Asaumi et al., "Expression of neurotrophins and their receptors (TRK) during fracture healing," Bone, 2000, 26(6):625-633.
Awad et al., "Acquired resistance to crizotinib from a mutation in CD74-ROS1.", N Engl. J Med, 368(25): 2395-401, 2013.
Bartenstein et al., "Lipofibromatosis-like neural tumor: Case report of a unique infantile presentation," JAAD Case Reports, 4(2):185-188, 2018.
Baughn et al., "Abstract 5115: Whole-Genome Mate Pair Sequencing Reflex Test to Characterize Chromosome Rearrangements in Hematologic Neoplasia," Blood, 2017, 130: 5115.
Bavle et al., "Abstract GENE-04: Pediatric Malignant Epithelioid Glioneuronal Tumor: Pathological, Clinical, and Molecular Characterization of a Rare and Deadly Malignancy," Neuro-Oncology, Jun. 2017, iv18-iv19.
Bender et al., Abstract HG-024: Multiple Novel Fusion Genes with the RTK-RAS-PI3K Signalling Axis Highlight its Central Role in the Turmorigenesis of Pediatric Gioblastoma, Neuro-oncology, Jun. 2014, 145.
Bensinger et al., "Transplantation of allogeneic peripheral blood stem cells mobilized by recombinant human granulocyte colony stimulating factor," Stem Cells, Jan. 1996;14(1):90-105.
Bensinger et al., "Transplantation of allogeneic peripheral blood stem cells mobilized by recombinant human granulocyte colony-stimulating factor [see comments].," Blood, Mar. 15, 1995;85(6):1655-8.
Bertrand et al., "The crystal structures of TrkA and TrkB suggest key regions for achieving selective inhibition," Journal of molecular biology, Oct. 26, 2012;423(3):439-53.
Birch et al., "Chromosome 3 anomalies investigated by genome wide SNP analysis of benign, low malignant potential and low grade ovarian serous tumours.", PLoS One, 6(12): e28250, 2011.
Branford, S., et al. "High frequency of point mutations clustered within the adenosine triphosphate-binding region of BCR/ABL in patients with chronic myeloid leukemia or Ph-positive acute lymphoblastic leukemia who develop imatinib (STI571) resistance," Blood, May 2002, 99, 3472-3475.
Brastianos et al., "Abstract OS06.4: Identification of Novel NTRK Fusion in Glioneuronal Tumors and Radiographic Response Following Therapy with an NTRK Inhibitor," Neuro-Oncology, May 2017, iii11, 1 pageMeeting Info: 5th Quadrennial Meeting of the World Federation of Neuro-Oncology Societies, WFNOS. Zurich, Switzerland, 2017.
Brenca et al., "Transcriptome sequencing identifies ETV6-NTRK3 as a gene fusion involved in GIST," J. Pathol. 238(4):543-549, 2016.
Brinner et al., "A rapid and general method for asymmetric syntesis of 2-substituted pyrrolidines using ter-butanesulfinamide," Organic & Biomolecular Chemistry, Jan. 2005, 3(11): 2109.
Brodeur, "Neuroblastoma: biological insights into a clinical enigma," Nat. Rev. Cancer, 2003, 3:203-216.

Bruse et al., "Improvements to Bead Based Oligonucleotide Ligation SNP Genotyping Assays," Biotechniques, Nov. 2008, 45:559-571.
Brzezianska et al., "Rearrangements of NTRK1 oncogene in papillary thyroid carcinoma," Neuroendocrinology Letters, 2007, 28(3):221-229.
Burris et al., "Pharmacokinetics (PK) of LOXO-101 During the First-in-Human Phase I Study in Patients with Advanced Solid Tumors," Interim Update AACR Annual Meeting, Mar. 2015, Philadelphia, PA., 1 page.
Butti et al., "A sequence analysis of the genomic regions involved in the rearrangements between TPM3 and NTRK1 genes producing TRK oncogenes in papillary thyroid carcinomas," Genomics. 28(1):15-24, 1995.
Caira, "Crystalline Polymorphism of Organic Compounds," Topics in Current Chemistry, Feb. 1999, 198: 163-208.
Cajaiba et al., "Expanding the spectrum of ALK-rearranged renal cell carcinomas in children: Identification of a novel HOOK1-ALK fusion transcript.", Genes Chromosomes Cancer, 55(10): 814-7, 2016.
Calabresi and Chabner, Goodman & Gilnnan's the Pharmacological Basis of Therapeutics, 10th ed., 2001, p. 1388, para 2, lines 4-5.
Calero et al., "Sunitinib suppress neuroblastoma growth through degration of MYCN and inhibition of angiogenesis," PLoS One, Apr. 23, 2014;9(4):e95628. doi: 10.1371/journal.pone.0095628. eCollection 2014.
Camoratto et al., "CEP-751 inhibits trk receptor tyrosine kinase activity in vitro and exhibits anti-tumor activity." International Journal of cancer. 72(4): 673-9, 1997.
Campos et al., "Enantioselective, palladium-catalyzed alpha-acylation of N-Boc-pyrrolidine," J. Am. Chem Soc., 2006, 128:3538-3539.
Capparelli et al., "Stromal neuregulin-1 modulates the response to MEK inhibitors in WT BRAF/WT NRAS (WT/WT) melanomas", Pigment Cell Melanoma Res. vol. 30, No. 5, pp. e61, 2017.
Caria et al., "Cytogenetic and molecular events in adenoma and well-differentiated thyroid follicular-cell neoplasia," Cancer Genet. Cytogenet., 2010, 203:21-29.
Carpinelli et al., "PHA-739358, a potent inhibitor of Aurora kinases with a selective target inhibition profile relevant to cancer," Mol Cancer Ther, Dec. 2007;6(12 Pt 1):3158-3168.
Catic et al., "Abstract 1537: The frequency of a novel KANK1 and NTRK3translocation and BRAFV600E mutation in patients diagnosed with metanephric adenoma utilizing molecular mechanisms," 2017 Annual Meeting of the American Society of Clinical Oncology, 2017, 1 page.
Catic et al., "A novel cytogenetic and molecular characterization of renal metanephric adenoma, identification of partner genes involved in translocation t(9;15)(p24;q24)," Cancer Genet. 214-215:9-15, doi: 10.1016/j.cancergen.2017.03.001, 2017.
Chang-Qi et al., "Brain derived neurotrophic factor (BDNF) contributes to the pain hypersensitivity following surgical incision in the rats," Molecular Pain, 2008, 4:27.
Chaudhuri et al., "Early Detection of Molecular Residual Disease in Localized Lung Cancer by Circulating Tumor DNA Profiling," Cancer Discov, Dec. 2017, 7(12):1394-1403.
Chen et al., "40: The landscape of kinase fusions in 445 Chinese NSCLC patients," Annals of Oncology, Oct. 2017, 28(7): vii16, 1 page.
Cherry et al., "Recent kinase and kinase inhibitor X-ray structures: mechanisms of inhibition and selectivity insights," Curr Med Chem. Mar. 2004;11(6):663-73.
Chiang et al., "NTRK Fusions Define a Novel Uterine Sarcoma Subtype with Features of Fibrosarcoma," Am. J. Surg. Pathol. doi: 10.1097/PAS.0000000000001055, 2018.
Chinese Office Action in Chinese Patent Application No. CN 201180025013.9, dated Apr. 28, 2014, 11 pages.
Chinese Office Action in Chinese Patent Application No. CN201080040095.X, dated Feb. 27, 2015, 8 pages (English translation).
Chmielecki et al., "Abstract LB-178: Genomic profiling of 1239 diverse pediatric cancers identifies novel discoveries across tumors", Cancer Research, vol. 76, No. 14, Supp. Supplement. Abstract No.

(56) References Cited

OTHER PUBLICATIONS

LB-178. 107th Annual meeting of the American Association for Cancer Research, AACR. New Orleans, LA Apr. 16-20, 2016.
Chmielecki et al., "Genomic Profiling of a Large Set of Diverse Pediatric Cancers Identifies Known and Novel Mutations across Tumor Spectra.", Cancer Research, 77(2): 509-519, 2017.
Cho et al., "Expression of mRNA for brain-derived neurotrophic factor in the dorsal root ganglion following peripheral inflammation," Brain Research, 1997, 749:358-362.
Choi et al., "(R)-2-Phenylpyrrolidine Substituted Imidazopyridazines: A New Class of Potent and Selective Pan-TRK Inhibitors," ACS medicinal chemistry letters, Mar. 19, 2015;6(5):562-567.
Church et al., "Abstract ST16: A Novel EML4-NTRK3 Translocation in Infantile Fibrosarcoma and Congenital Mesoblastic Nephroma Requires a New Approach to Conventional Diagnostic Algorithms," J Molecular Diag, 2015, 816.
Church et al., "Recurrent EML4—NTRK3 fusions in infantile fibrosarcoma and congenital mesoblastic nephroma suggest a revised testing strategy," Mod. Pathol. 31(3), 463-473, 2018.
Cocce et al., "Identification of ZCCHC8 as fusion partner of ROS1 in a case of congenital glioblastoma multiforme with a t(6;12)(q21;q24.3)", Genes Chromosomes Cancer, 55(9): 677-87, 2016.
Coebergh et al., "Abstract 490: Identification of oncogenic gene fusions in primary colon cancers," Cancer Research, Jul. 2017, DOI: 10.1158/1538-7445.AM2017-490, 2 page.
Colombian Office Action in Colombian Application No. CO 12-022-116-4, dated Feb. 14, 2014, 8 pages.
Colombian Office Action in Colombian Application No. CO 12-229421-4, dated Jan. 21, 2014, 6 pages.
Comina-Mendez and Turner, "Predicting Relapse with Circulating Tumor DNA Analysis in Lung Cancer," Cancer Discov, Dec. 2017, 7(12): 1368-1370.
Cook et al., "Somatic chromosomal engineering identifies BCAN-NTRK1 as a potent glioma driver and therapeutic target," Nat. Comm. 8(15987). DOI 10.1038/ncomms15987, 2017.
Crescenzo et al., "Convergent mutations and kinase fusions lead to oncogenic STAT3 activation in anaplastic large cell lymphoma.", Cancer Cell., 27(4): 516-32, 2015.
Croucher et al., "TrkB inhibition by GNF-4256 slows growth and enhances chemotherapeutic efficacy in neuroblastoma xenografts," Cancer Chemother Pharmacol. Jan. 2015;75(1):131-41. doi: 10.1007/s00280-014-2627-1. Epub Nov. 14, 2014.
Cruz, "Lung cancer: epidemiology, etiology and prevention," Clinics in Chest Medicine, 2011, 32(4): 1-61.
Cui et al., "Abstract #MA 07.09: ALK/ROS1/Inhibitor TPX-0005 Effectively Overcomes Clinical Resistance Solvent Front Mutations," Abstracts, Nov. 2017, p. S1829.
Cui et al., "Use of capture-based next-generation sequencing to detect ALK fusion in plasma cell-free DNA of patients with non-small-cell lung cancer", Oncotarget, 2771-2780, 2016.
Dacic et al., "ALK FISH patterns and the detection of ALK fusions by next generation sequencing in lung adenocarcinoma", Oncotarget, vol. 7, No. 50, pp. 82943-82952, 2016.
Dang et al., "Expression of nerve growth factor receptors is correlated with progression and prognosis of human pancreatic cancer," J. Gastroenterology and Hepatology, 2006, 21(5): 850-858.
Das et al., "Synergistic Effects of Crizotinib and Temozolomide in Experimental FIG-ROS1 Fusion-Positive Glioblastoma.", Cancer Growth Metastasis, 8:51-60, 2015.
Davare et al., "Foretinib is a potent inhibitor of oncogenic ROS1 fusion proteins.", Proc. Natl. Acad. Sci. USA., 110(48): 19519-24, 2013.
Davare et al., "Structural insight into selectivity and resistance profiles of ROS1 tyrosine kinase inhibitors.", Proc. Natl. Acad Sci. USA., 1 12(39): E5381-90, 2015.
Davidson et al., "Expression and activation of the nerve growth factor receptor TrkA in serous ovarian carcinoma," Clin. Cancer Res., 2003, 9(6):2248-2259.
Davies and Dobele, "Molecular pathways: ROS1 fusion proteins in cancer.", Clin. Cancer Res, 19(15): 4040-4045, 2013.
Davies et al., "Identifying and targeting ROS1 gene fusions in non-small cell lung cancer.", Clin Cancer Res 18: 4570-4579, 2012.
Davies et al., "Resistance to ROS1 inhibition mediated by EGFR pathway activation in non-small cell lung cell," PLoS One, 2013, 8(12):e82236, 13 pages.
Davis et al., "Infantile NTRK-associated Mesenchymal Tumors," Pediatr. Dev. Pathol. 21(1):68-78, 2018.
de Smith et al., "Clonal and microclonal mutational heterogeneity in high hyperdiploid acute lymphoblastic leukemia", Oneatarget., 7(45) 72733-72745, 2016.
Deihimi et al., "BRCA2, EGFR, and NTRK mutations in mismatch repair-deficient colorectal cancers with MSH2 or MLH1 mutations," Oncotarget. Jun. 20;8(25):39945-39962, 2017.
Delafoy et al., "Role of nerve growth factor in the trinitrobenzene sulfonic acid-induced colonic hypersensitivity," Pain, 2003, 105:489-497.
Demaria et al., "Development of tumor-infiltrating lymphocytes in breast cancer after neoadjuvant paclitaxel chemotherapy," Clin Cancer Res, Oct. 2001;7(10):3025-30.
Di Mola et al., "Nerve growth factor and Trk high affinity receptor (TrkA) gene expression in inflammatory bowel disease," Gut, 2000, 46(5):670-678.
Dionne et al., "Cell cycle-independent death of prostate adenocarcinoma is induced by the trk tyrosine kinase inhibitor CEP-751 (KT6587)," Clin. Cancer Research, 1998, 4(8):1887-1898.
Doebele et al., "Abstract 8023: NTRK1 gene fusions as a novel oncogene target in lung cancer," 2013 Annual Meeting of the American Society of Clinical Oncology, Chicago, IL, 2013, 1 page.
Doebele et al., "Phase II Trial of Stereotactic Body Radiation Therapy Combined with Erlotinib for Patients With Limited but Progressive Metastatic Non-Small-Cell Lung Cancer," J. Clin. Oncol., 2014, 32:9 pages.
Dolle et al., "Nerve growth factor-induced migration of endothelial cells," J. Pharmacol Exp Ther, 2005, 315(3):1220-1227.
Dolomanov et al., "OLEX2: a complete structure solution, refinement and analysis program," J Appl. Cryst. 2009, 42, 339-341.
Dou et al., "Increased nerve growth factor and its receptors in atopic dermatitis: an immunohistochemical study," Archives of Dermatological Research, 2006, 298(1):31-37.
Drilon et al., "A Novel Crizotinib-Resistant Solvent-Front Mutation Responsive to Cabozantinib Therapy in a Patient with ROS1-Rearranged Lung Cancer.", Clin. Cancer Res., 22(10): 2351-8, 2016.
Drilon et al., "A phase 1 study of oral LOXO 292 in adult patients with advanced solid tumors, including RET-fusion non-small cell lung cancer, medullary thyroid cancer and other tumors with increased RET activity," Annals of oncology Developmental Therapeutics, Sep. 2017, 28(5): 138.
Drilon et al., "Abstract CT007: Entrectinib, an oral pan-Trk, ROS1, and ALK inhibitor in TKI-naïve patients with advanced solid tumors harboring gene rearrangements: Updated phase I results," Cancer research, 76(14), AACR 107th Annual Meeting, Apr. 2016, URL <http://cancerres.aacrjournals.org/content/76/14_Supplement/CT007.short>, 5 pages.
Drilon et al., "What hides behind the MASC: clinical response and acquired resistance to entrectinib after ETV6-NTRK3 identification in a mammary analogue secretory carcinoma (MASC)," Annals of Oncology., Feb. 15, 2016, 27(5):920-926.
Du et al., "Expression of NGF family and their receptors in gastric carcinoma: a cDNA microarray study," World Journal of Gastroenterology, http://www.wjgnet.com/1007-9327/full/v9/i7/1431.htm, Jul. 2003, 9(7):1431-1434.
Duranti et al., "Homologation of Mexiletine alkyl chanin and stereoselective blockade of skelatal muscle sodium channels," Euro. J. Med. Chem., 2000, 35:147-156.
Durham et al. "Diverse and Targetable Kinase Alterations Drive Histiocytic Neoplasms," Blood. 126(23):481, 215.
Eguchi et al., "Fusion of ETV6 to neurotrophin-3 receptor TRKC in acute myeloid leukemia with t(12;15)(p13;q25)," Blood, 1999, 93(4):1355-1363.
Ellison et al., "Abstract O13: Genetic alterations in uncommon low-grade neural tumors—BRAF, FGFR1, and MYB/MYBL1 muta-

(56) References Cited

OTHER PUBLICATIONS tions occur frequently and align with morphology," Neuropathology and Applied Neurobiology, 2016, 42(S1): 18.
Elvin et al., "319:Genomic profiling of uterin leiomyosarcomas reveal frequent alterations in Akt/mammalian target of rapamycin (mTOR) pathway genes and other actionable genomic abnormalties linked to targeted therapies," Poseter Session-Molecular Targeted Agents I, Nov. 2014, 1 page.
Engman et al., "Syngeneic transplant in mantle cell lymphoma: a rare event and review of the literature," Clin Adv Hematol Oncol. May 2009;7(5):321-3.
Esmo, "TRK Cancer-Causing Mutation Discovered in 1982 Finally Target of Clinical Trials: Matching drugs to long-overlooked oncogene," European Society of Medical Oncology, Jan. 2015, 2 pages.
Essand et al., "Genetically engineered T cells for the treatment of cancer," J Intern Med. Feb. 2013;273(2):166-81. doi: 10.1111/joim.12020.
Estrada-Bernal et al., "Abstract #: C65: TRK kinase domain mutations that induce resistance to a pan-TRK inhibitor," Poster, Presented at Proceedings of the AACR—NCI—EORTC International Conference: Molecular Targets and Cancer Therapeutics, Boston MA, Nov. 5-9, 2015; Mol Cancer Ther, Dec. 2015, 14(12)(Suppl. 2): 1 page.
Estrada-Bernal et al., "Abstract #: LB-118: Identification of TRKA and TRKB kinase domain mutations that induce resistance to a pan-TRK inhibitor," Poster, Presented at Proceedings of the 107th Annual Meeting of the American Association for Cancer Research, New Orleans LA, Apr. 16-20, 2016; Cancer Res, Jul. 2016, 76(14): 1 page.
European Office Action in Application No. 15808300.6, dated Nov. 20, 2018.
European Search Report in European Application No. 13197815.7, dated Apr. 1, 2014, 5 pages.
Euthus et al., "ETV6-NTRK3—Trk-ing the primary event in human secretory breast cancer," Cancer Cell, 2002, 2(5):347-348.
Extended European Search Report in European Application No. 17199899.0, dated Feb. 26, 2018, 7 pages.
Extended European Search Report in European Application No. 18151233.6, dated Jun. 26, 2018, 6 pages.
Facchinetti et al., "Crizotinib-Resistant ROS1 Mutations Reveal a Predictive Kinase Inhibitor Sensitivity Model for ROS1- and ALK-Rearranged Lung Cancers.", Clin. Cancer Res., 22(24): 5983-5991, 2016.
Farago et al., "Abstract MINI30.09: Clinical Response to Entrectinib in a Patient with NTRK1-Rearranged Non-small cell Lung Cancer," J Thoracic Oncol, Sep. 2015, 10(9-S2): S374-S375.
Farago et al., "Durable clinical response to entrectinib in NTRK1-rearranged non-small cell lung cancer," J. Thorac Oncol. 10(12):1670-1674, 2015.
Farhat et al., "Primary benign and malignant thyroid neoplasms with signet ring cells: cytologic, histologic, and molecular features," Am. J. Clin. Pathol., 148(3):251-258, 2017.
Fernandez-Cuesta et al., "Abstract 1531: Cross-entity mutation analysis of lung neuroendocrine tumors sheds light into their molecular origin and identifies new therapeutic targets," AACR Annual Meeting 2014, Apr. 2014, URL <http://cancerres.aacrjournals.org/content/74/19_Supplement/1531.short>, 5 pages.
Flannery et al., "Immunomodulation: NK cells activated by interferon-conjugated monoclonal antibody against human osteosarcoma," Eur J Cancer Clin Oncol. Jun. 1984;20(6):791-8.
Forghieri et al., Abstract P137: Chronic Eosinophilic Leukemia with ETV6-NTRK3 Fusion Transcript in an Elderly Patient Affected with Pancreatic Carcinoma, Haemologica, 2010, 95(s3): S125-S126.
Frattini et al., "The integrated landscape of driver genomic alterations in glioblastoma," Nature Genet., 2013, 45:1141-1149.
Freund-Michel and Frossard, "The nerve growth factor and its receptors in airway inflammatory diseases," Pharmacology & Therapeutics, 2008, 117(1):52-76.
Frey et al., "7-Aminopyrazolo[1,5-a]pyrimidines as potent multitargeted receptor tyrosine kinase inhibitors," J. Med. Chem, Jul. 2008, 51(13):3777-3787.
Fu et al., "The Frequency and Clinical Implication of ROS1 and RET Rearrangements in Resected Stage IIIA-N2 Non-Small Cell Lung Cancer Patients.", PLoS One, 10(4):e0124354, 2015.
Fuse et al., "Mechanisms of Resistance to NTRK Inhibitors and Therapeutic Strategies in NTRK1-Rearranged Cancers," Mol. Cancer Ther.,. Jan;6(1):36-44, 2016.
Gainor et al., "Patterns of Metastatic Spread and Mechanisms of Resistance to Crizotinib in ROS1-Positive Non—Small-Cell Lung Cancer", JCO Precis Oneal. 10.1200/PO. 17.00063, 2017.
Gang et al., "The landscape of fusion transcripts in spitzoid melanoma and biologically indeterminate spitzoid tumors by RNA sequencing.", Mod Pathol., 29(4): 359-69, 2016.
Gao et al., "Driver fusions and their implications in the development and treatment of human cancers," Cell Rep. 23(1):227-238.e3, 2018.
Gatalica et al., "Abstract A047: Molecular characterization of the malignancies with targetable NTRK gene fusions," American Association for Cancer Research, Jan. 2018, 2 pages.
Gaudet et al., "Allele-specific PCR in SNP genotyping," Methods Mol Biol. 2009;578:415-24. doi: 10.1007/978-1-60327-411-1_26.
Gavrin et al., "Synthesis of Pyrazolo[1,5-[alpha]]pyrimidoinone Regioisomers," J Org Chem, Feb. 2007, 72(3): 1043-1046.
GenBank Accession No. AAB33109.1, "trkB [*Homo sapiens*]," Jul. 27, 1995, 1 page.
GenBank Accession No. AAB33111.1, "trkC [*Homo sapiens*]," Jul. 27, 1995, 1 page.
GenBank Accession No. NM_ 002529, "high affinity nerve growth factor receptor isoform 2 precursor [*Homo sapiens*]," May 11, 2014, 4 pages.
GenBank Accession No. NM_001007792 "*Homo sapiens* neurotrophic tyrosine kinase, receptor, type 1 (NTRK1), transcript variant 3, mRNA," May 10, 2014, 5 pages.
GenBank Accession No. NP 001007793, "high affinity nerve growth factor receptor isoform 3 [*Homo sapiens*]," May 10, 2014, 3 pages.
GenBank Accession No. NP_ 002520 "high affinity nerve growth factor receptor isoform 2 precursor [*Homo sapiens*]," May 11, 2014, 4 pages.
GenBank Accession No. S76473.1, "trkB [human, brain, mRNA, 3194 nt]," Jul. 27, 1995, 2 pages.
GenBank Accession No. S76475.1, "trkC [human, brain, mRNA, 2715 nt]," Jul. 27, 1995, 2 pages.
Giacomini et al., "Breakpoint Analysis of Transcriptional and Genomic Profiles Uncovers Novel Gene Fusions Spanning Multiple Human Cancer Types", PLoS Gene.t, 9(4):e1003464, 2013.
Greco et al., "Chromosome I rearrangements involving the genes TPR and NTRK1 produce structurally different thyroid-specific TRK oncogenes,"Genes Chromosomes Cancer. 19(2):112-23, 1997.
Greco et al., "Rearrangements of NTRK1 gene in papillary thyroid carcinoma," Molecular and Cellular Endocrinology, 2010, 321(1):44-49.
Greco et al., "The DNA rearrangement that generates the TRK-T3 oncogene involves a novel gene on chromosome 3 whose product has a potential coiled-coil domain," Mol. Cell. Biol. 15(11):6118-6127, 1995.
Greco et al., "TRK-T1 is a novel oncogene formed by the fusion of TPR and TRK genes in human papillary thyroid carcinomas," Oncogene. 7(2):237-42, 1992.
Green & Wuts, eds, "Protective Groups in Organic Synthesis," John Wiley & Sons Inc, May 8, 1999.
Groisberg et al., "Clinical next-generation sequencing in sarcomas", Journal of Clinical Oncology, vol. 34, Supp. Supplement 15; Abstract No. 11046; 2016 Annual Meeting of the American Society of Clinical Oncology, ASCO 2016, Chicago, IL. Jun. 3-7, 2016.
Gruber-Olipitz et al., "Neurotrophin 3/TrkC-regulated proteins in the human medulloblastoma cell line DAOY," J. Proteome Research, 2008, 7(5):1932-1944.
Gu et al., "Lung adenocarcinoma harboring concomitant SPTBN1-ALK fusion, c-Met overexpression, and HER-2 amplification with inherent resistance to crizotinib, chemotherapy, and radiotherapy.", J Hematol Oneal, 9(1): 66, 2016.

(56) References Cited

OTHER PUBLICATIONS

Gwak et al., "Attenuation of mechanical hyperalgesia following spinal cord injury by administration of antibodies to nerve growth factor in the rat." Neurosci. Lett., 2003, 336:117-120.

Hainsworth et al., "Lung Adenocarcinoma with Anaplastic Lymphoma Kinase (ALK) Rearrangement Presenting as Carcinoma of Unknown Primary Site: Recognition and Treatment Implications.", Drugs Real World Outcomes, 3:115-120, 2016.

Hakinni et al., "Minimally invasive approaches to prostate cancer: a review of the current literature.", Urol. J., 4: 130-137, 2007.

Hallberg and Palmer, "The role of the ALK receptor in cancer biology.", Ann. Oncology, 27 (Suppl 3):iii4-iii15. doi: 10.1093/annonc/mdw301, 2016.

Hamdouchi et a l "Imidazo[1,2-b]pyridazines, novel nucleus with potent and broad spectrum activity against human picornaviruses: design, synthesis, and biological evaluation" J Med Chem., Sep. 25, 2003;46(20):4333-4341.

Hansen et al., "Autophagic cell death induced by TrkA receptor activation in human glioblastoma cells," J. of Neurochemistry, 2007, 103:259-275.

Harada et al., "Role and Relevance of TrkB Mutations and Expression in Non-Small Cell Lung Cancer," Clinical Cancer Research, Jan. 17, 2011, 17(9):2638-2645.

Harwood et al., "Experimental organic chemistry—Principles and practice," Experimental Chemistry—Organic Chemistry and Reaction, Jan. 1, 1989, 127-132.

Hayashi et al., "Crizotinib treatment for refractory pediatric acute myeloid leukemia with RAN-binding protein 2-anaplastic lymphoma kinase fusion gene.", Blood Cancer J, 6(8): e456, 2016.

Hechtman et al., "Identification of targetable kinase alterations in patients with colorectal carcinoma that are preferentially associated with wild-type RAS/RAF," Mol. Cancer Res. 14(3):296-301, 2016.

Hechtman et al., Abstract 1837: Pan-TRK IHC Is an Efficient and Reliable Screening Assay for Targetable NTRK Fusions, Annual Meeting Abstracts, 2017, 457A.

Herzberg et al., "NGF involvement in pain induced by chronic constriction injury of the rat sciatic nerve," Neuroreport, 1997, 8:1613-1618.

Hinrichs et al., "Exploiting the curative potential of adoptive T-cell therapy for cancer," Immunol Rev. Jan. 2014;257(1):56-71. doi: 10.1111/imr.12132.

Hobbs et al., "Effects of T-Cell Depletion on Allogeneic Hematopoietic Stem Cell Transplantation Outcomes in AML Patients," J Clin Med. Mar. 19, 2015;4(3):488-503. doi: 10.3390/jcm4030488.

Holla et al., "ALK: a tyrosine kinase target for cancer therapy", Cold Spring Harb Mol Case Study, 3(1):a001115. doi: 10.1101/mcs.a001115, 20 pages, 2017.

Hong et al., "Clinical Safety and activity from a Phase 1 study of LOXO-101, a selective TRKA/B/C inhibitor, in solid-tumor patients with NTRK gene fusions," 2016 AACR Annual Meeting, Apr. 17, 2016, 32 pages.

Hornick et al., "Expression of ROS1 predicts ROS1 gene rearrangement in inflammatory myofibroblastic tumors.", Mod Pathol., 28(5): 732-9, 2015.

Hover et al., "Abstract TMOD-07: NTRK3 Gene Fusions Drive Tumorigenesis in Novel Models of Pediatric High Grade Glioma," Neuro-Oncology, Jun. 2017, iv49.

Howell et al., "Dynamic allele-specific hybridization. A new method for scoring single nucleotide polymorphisms," Nat Biotechnol. Jan. 1999;17(1):87-8.

Hu et al., "Decrease in bladder overactivity with REN1820 in rats with cyclophosphamide induced cystitis," J. Urology, 2005, 173(3):1016-1021.

Hu et al., "Identification of brain-derived neurotrophic factor as a novel angiogenic protein in multiple myeloma" Cancer Genetics and Cytogenetics, 2007, 178:1-10.

Huehls et al., "Bispecific T-cell engagers for cancer immunotherapy,"Immunol Cell Biol. Mar. 2015;93(3):290-6. doi: 10.1038/icb.2014.93. Epub Nov. 4, 2014.

Hyrcza et al., "Abstract OFP-06-007: Comparison of ultrastructural features between pediatric Mammary Analogue Secretory Carcinoma (MASC) of the salivary glands and Pediatric Secretory Breast Carcinoma (SBC) reveals similar pathological features," Virchows Arch, Sep. 2016, 469(S1): S17.

Igaz et al., "Biological and clinical significance of the JAK-STAT pathway; lessons from knockout mice," Inflamm Res., 2001, 50:435-441.

Ihle et al., "The Roles of Jaks and Stats in Cytokine Signaling," Canc. J. Sci. Am., 1998, 4(1):84-91.

Ihuegbu et al., "Non-invasive detection of crizotinib resistance in ALK-rearranged lung adenocarcinoma directs treatment with next-generation ALK inhibitors", J Clin. Oncology, vol. 34, Supp. Supplement 15, Abstract No. e20643, 2016 Annual Meeting of the American Society of Clinical Oncology, Chicago, IL, 2016.

Ikeda et al., "Basic Sciene", Annals of Oncology. vol. 28 (suppl_10): xl x6.10.1093/annonc/mdx652, 2017.

Imamura et al., "Allogeneic hematopoietic stem cell transplantation in adult acute lymphoblastic leukemia: potential benefit of medium-dose etoposide conditioning," Exp Hematol Oncol, Jul. 16, 2015;4:20. doi: 10.1186/s40164-015-0015-0. eCollection 2015.

Iniguez-Ariza et al., "Abstract 6087: NTRK1-3 point mutations in poor prognosis thyroid cancers," J Clinical Oncology, May 2017, 35(15): 6087.

Isdori et al., "Advancement in high dose therapy and autologous stem cell rescue in lymphoma," World J Stem Cells, Aug. 2015, 7(7):1039-1046.

Iyama et al., "Identification of Three Novel Fusion Oncogenes, SQSTM1/NTRK3, AFAP1L2/RET, and PPFIBP2/RET, in Thyroid Cancers of Young Patients in Fukushima," Thyroid. 27(6):811-818, 2017.

Iyer et al., "AZ64 inhibits TrkB and enhances the efficacy of chemotherapy and local radiation in neuroblastoma xenografts," Cancer Chemother Pharmacol. Sep. 2012;70(3):477-86. doi: 10.1007/s00280-012-1879-x. Epub May 24, 2012.

Jaggar et al., "Inflammation of the rat urinary bladder is associated with a referred thermal hyperalgesia which is nerve growth factor dependent," Br. J. Anaesth, 1999, 83:442-448.

Japanese Office Action in Japanese Application No. JP 2013-511239, dated Mar. 4, 2015, 2 pages (English translation).

Jencks and Regenstein, "Ionization Constatns fo Acids and Bases," Handbook of Biochemistry and Molecular Biology, 3rd ed., G. D. Fassman, CRC Press, 1976, 1: 305-347.

Jin et al., "TrkC plays an essential role in breast tumor growth and metastasis," Carcinogenesis, 2010, 31(11):1939-1947.

Johnson et al., "Comprehensive Genomic Profiling of 282 Pediatric Low- and High-Grade Gliomas Reveals Genomic Drivers, Tumor Mutational Burden, and Hypermutation Signatures.", Oncologist. 22(12): 1478-1490, 2017.

Jones et al., "Recurrent somatic alterations of FGFR1 and NTRK2 in pilocytic astrocytoma," Nature Genetics, 2013, 45:927-932.

Kao et al., "Recurrent BRAF Gene Fusions in a Subset of Pediatric Spindle Cell Sarcomas," Am. J. Surg. Pathol. 42(1):28-38, 2018.

Karachialiou et al., "Real-time liquid biopsies become a reality in cancer treatment", Ann. Transl. Med, 3(3):36, 2016.

Katayama et al., "Cabozantinib Overcomes Crizotinib Resistance in ROS1 Fusion—Positive Cancer", Clin. Cancer Res., 21 (I): 166-7 4, 2015.

Katayama et al., "Mechanisms of Acquired Crizotinib Resistance in ALKRearranged Lung Cancers," Sci Transl Med, Feb. 2012, 4(120): 120ra17.

Katayama et al., "Therapeutic targeting of anaplastic lymphoma kinase in lung cancer: a paradigm for precision cancer medicine.", Clin Cancer Res, 21(10): 2227-35, 2015.

Keysar et al., "A patient tumor transplant model of Squamous cell cancer identifies PI3K inhibitors as candidate therapeutics in defined molecular bins," Molecular Oncology, 2013, 7(4):776-790.

Kim et al., "Mammaglobin-A is a target for breast cancer vaccination", OncoImmunology 5(2): e1069940, 2016.

Kim et al., "NTRK1 fusion in glioblastoma multiforme," PloS One, 2014, 9(3):e91940.

Kim et al., "SEC31A-ALK Fusion Gene in Lung Adenocarcinoma", Cancer Res Treat, 48(1): 398-402, 2016.

(56) References Cited

OTHER PUBLICATIONS

Klijn et al., "A comprehensive transcriptional portrait of human cancer cell lines," Nat Biotechnol., 2015, 33(3):306-312.
Koboldt et al., "The next-generation sequencing revolution and its impact on genomics," Cell, Sep. 26, 2013;155(1):27-38. doi: 10.1016/j.cell.2013.09.006.
Kohsaka et al., "Refractory and metastatic infantile fibrosarcoma harboring LMNA—NTRK1 fusion shows complete and durable response to crizotinib," Hum. Pathol. 72:167-173, 2017.
Kolokythas et al., "Nerve growth factor and tyrosine kinase A receptor in oral squamous cell carcinoma: is there an association with perineural invasion?" J. Oral Maxillofacial Surgery, 2010, 68(6):1290-1295.
Kralik et al., "Characterization of a newly identified ETV6-NTRK3 fusion transcript in acute myeloid leukemia," Diagn. Pathol. 6:19, 2011.
Kremer et al., "The safety and efficacy of a JAK inhibitor in patients with active rheumatoid arthritis: Results of a double-blind, placebo-controlled phase IIa trial of three dosage levels of CP-690,550 versus placebo," Arth. & Rheum., 2009, 60:1895-1905.
Kruettgen et al., "The dark side of the NGF family: neurotrophins in neoplasias," Brain Pathology, 2006, 16:304-310.
Kubler et al., "Self-adjuvanted mRNA vaccination in advanced prostate cancer patients: a first-in-man phase I/IIa study.", J. Immunother Cancer 3 :26, 2015.
Kusano et al., "Two Cases of Renal Cell Carcinoma Harboring a Novel STRN-ALK Fusion Gene.", Am J Surg Pathol. 40(6): 761-9, 2016.
Lamb et al., "Nerve growth factor and gastric hyperalgesia in the rat," Neurogastrenterol. Motil., 2003, 15:355-361.
Lansky et al., "The measurement of performance in childhood cancer patients," Cancer, 1987, 60(7):1651-1651.
Lecht et al., "Angiostatic effects of K252a, a Trk inhibitor, in murine brain capillary endothelial cells," Mol Cell Biochem, Jun. 2010;339(1-2):201-13. doi: 10.1007/s11010-010-0386-9. Epub Feb. 11, 2010.
Lee et al., "Identification of ROS1 rearrangement in gastric adenocarcinoma.", Cancer, 119(9): 1627-1635, 2013.
Leeman-Neill et al., "ETV6-NTRK3 is a common chromosomal rearrangement in radiation-associated thyroid cancer," Cancer, 2014, 120(6):799-807.
Leukemia, Wikipedia the Free Encyclopedia, Dec. 8, 2001, https://en.wikipedia.org/wiki/Leukemia, 15 pages.
Leyvraz et al., Abstract No. 897. Meeting Info: 33. Deutscher Krebskongress, DKK. Berlin, Germany, 2018.
Lezcano et al., "Regular transfusion lowers plasma free hemoglobin in children with sickle-cell disease at risk for stroke," Am. J. Surg. Pathol. doi: 10.1097/Pas.0000000000001070, 2018.
Li et al., "Brain derived neurotrophic factor (BDNF) contributes to the pain hypersensitivity following surgical incision in the rats," Molecular Pain, 2008, 4(28):1-11.
Li et al., "Combinational Analysis of FISH and Immunohistochemistry Reveals Rare Genomic Events in ALK Fusion Patterns in NSCLC that Responds to Crizotinib Treatment", J Thorac. Oneal., 12(1):94-101. doi: 10.1016/j .jtho.2016.08.145, 2017.
Li et al., "Correlation of expressions of GFAP, NT-3, TRK and NCAM with neurotropic molecular mechanism and clinical factors in adenoid cystic carcinoma of salivary gland," Chinese Journal of Cancer Prevention and Treatment, 2009, 16(6): 428-430 (with English abstract).
Li et al., "In vivo sensitized and in vitro activated B cells mediate tumor regression in cancer adoptive immunotherapy," J Immunol, Sep. 1, 2009;183(5):3195-203. doi: 10.4049/jimmunol.0803773. Epub Aug. 10, 2009.
Li et al., "Lumbar 5 ventral root transection-induced upregulation of nerve growth factor in sensory neurons and their target tissues: a mechanism in neuropathic pain," Mol. Cell. Neurosci., 2003, 23:232-250.
Li et al., "Trk inhibitor attenuates the BDNF/TrkB-induced protection of neuroblastoma cells from etopside in vitro and in vivo," Cancer Biol. Ther., Feb. 2015, 16(3):477-483.
Lin et al., "HG-48. Integrated Sequencing of Pediatric Pilocytic Astrocytomawith Anaplasia Reveals Molecular Features of Both Lowand High-Grade Glial Tumors", Neuro-Oneol, vol. 18, Supp. Supplement 3, pp. iii58, Abstract No. HG-48; 17th International Symposium on Pediatric Neuro-Oncology, ISPNO 2016. Liverpool, UK, Jun. 12, 2016-Jun 15, 2016.
Linch et al., "Systemic treatment of soft-tissue sarcoma [mdash] gold standard and novel therapies," Nature Reviews Clinical Oncology, 2014, 11(4):187-202.
Lorigan et al., "Phase III trial of two investigational Schedules of ifosfamide compared with standard-dose doxorubicin in advanced or metastatic soft tissue sarcoma: a European Organisation for Research and Treatment of Cancer Soft Tissue and Bone Sarcoma Group Study," J. Clin Oncol., 2007, 25(21):3144-3150.
Lovly et al., "Inflammatory myofibroblastic tumors harbor multiple potentially actionable kinase fusions," Cancer Discov., 2014, 4(8):889-895.
Lu et al., "Targeted next generation sequencing identifies somatic mutations and gene fusions in papillary thyroid carcinoma," Oncotarget. 8(28):45784-45792, 2017.
Ma and Woolf, "The progressive tactile hyperalgesia induced by peripheral inflammation is nerve growth factor dependent," Neuroreport, 1997, 8:807-810.
Ma et al., "Responses to crizotinib in patients with ALK-positive lung adenocarcinoma who tested immunohistochemistry (IHC)-positive and fluorescence in situ hybridization (FISH)-negative", Oncotarget, 7(39), 64410-64420, 2016.
Macleod, et al., "Abstract 0294: Gene Targets of ETV6-NTRK3 Fusion," Haematologica, 14th Congress of the European Hematology Association,2009, 94(s2): 116.
Majweska et al., Cancer Research, vol. 76, No. 14, Supp. Supplement. Abstract No. 3190. 107th Annual meeting of the American Association for Cancer Research, AACR. New Orleans, LA Apr. 16-20, 2016.
Marchetti et al., "Frequent mutations in neurotrophic tyrosine receptor kinase gene family in large cell neuroendocrine carcinoma of the the lung," Human Mutation, 2008, 29(5):609-616.
Marras et al., "Genotyping SNPs with molecular beacons," Methods Mol Biol, 2003;212:111-28.
Martin-Zanca et al., "A human oncogene formed by the fusion of truncated tropomyosin and protein tyrosine kinase sequences," Nature, 1986, 319:743-748.
Matayoshi, "Actions of brain-derived neurotrophic factor on spinal nociceptive transmission during inflammation in the rat," J. Physiol., 2005, 569:685-695.
McCahon et al., "Non-Resectable Congenital Tumors with the ETV6-NTRK3 Gene Fusion Are Highly Responsive to Chemotherapy," Med. Pediatr. Oncol., May 2003, 40(5):288-292.
McCarthy et al., "Tropomyosin receptor kinase inhibitors: a patent update 2009-2013," Expert Opin Ther Pat. Jul. 2014;24(7):731-44. doi: 10.1517/13543776.2014.910195. Epub May 8, 2014.
McMahon et al., "The biological effects of endogenous nerve growth factor on adult sensory neurons revealed by a trkA-IgG fusion molecule," Nat. Med., 1995, 1:774-780.
McMahon., "VEGF Receptor Signaling in Tumor Angiogenesis," The Oncologist, 2000, 5(1): 3-10.
Mekinist, Highlights of Prescribing Information, Initial Approval 2013, revised Nov. 2015, Novartis Pharmaceuticals Corp., 27 pages.
Melo-Jorge et al., The Chagas' disease parasite Trypanosoma cruzi exploits nerve growth factor receptor TrkA to infect mammalian hosts Cell Host & Microbe, 2007, 1(4):251-261.
Meyer et al., "Remarkable leukemogenic potency and quality of a constitutively active neurotrophin receptor, deltaTrkA," Leukemia, 2007, 21:2171-2180.
Milione et al., "Identification and characterization of a novel SCYL3-NTRK1 rearrangement in a colorectal cancer patient," Oncotarget, 8(33):55353-55360, 2017.
Montagnoli et al., "Anti-proliferative effects of GW441756, a novel inhibitor of NGFreceptor tyrosine kinase a (TRKA), in human sarcoma," Italian Journal of Anatomy and Embryology, Nov. 11, 2010, 115:117.

(56) References Cited

OTHER PUBLICATIONS

Morissette et al., "High-throughput crystallization: polymorphs, salts, co-crystals and solvates of pharmaceutical solids," Adv. Drug Deliv Rev, 2004, 56: 375-300.
Mulligan, "RET revisited: expanding the oncogenic portfolio.", Nature Reviews Cancer, 14, 173-186, 2014.
Murakami et al., "Integrated molecular profiling of juvenile myelomonocytic leukemia", Blood, blood-2017-07-798157; DOI: 10.1182/blood-2017-07-798157, 2018.
Nagasubruamanian et al., "Brief Report. Infantile Fibrsarcoma With NTRK3-ETV6 Fusion Successfully Treated With the Tropomyosin-Related Kinase Inhibitor LOXO-101," Pediatric Blood & Cancer, 2016, DOI 10.1002, 3 pages.
Nakagawara, "Trk receptor tyrosine kinases a bridge between cancer and neural development," Cancer Letters, 2001, 169(2):107-114.
Nakano et al., "Novel Oncogenic KLC1-ROS1 Fusion in Pediatric Low Grade Glioma", Pediatr Blood Cancer. vol. 64, S54-S55 Suppe. 4. 013-1-7, 2017.
Narayanan et al., "Discovery and preclinical characterization of novel small molecule TRK and ROS1 tyrosine kinase inhibitors for the treatment of cancer and inflammation," PLoS One, Dec. 26, 2013;8(12):e83380. doi: 10.1371/journal.pone.0083380. eCollection 2013.
National Cancer Institute at the National Institutes of Health, posted on or before Jan. 5, 2000, retrieved on Jan. 13, 2015, http://www.cancer.gov/, 2 pages.
National Comprehensive Cancer Network, posted on or before Dec. 3, 1998, retrieved on Jan. 13, 2015, http://www.nccn.org/, 1 page.
NCT02050919, "Sorafenib Tosylate, Combination Chemotherapy, Radiation Therapy, and Surgery in Treating Patients With High-Risk Stage IIB-IV Soft Tissue Sarcoma," ClinicalTrials.gov, First received Jan. 29, 2014, Last Updated Dec. 16, 2015, https://www.clinicaltrials.gov/ct2/show/NCT02050919, 5 pages.
NCT02122913, "Oral TRK Inhibitor LOXO-101 for Treatment of Advanced Adult Solid Tumors," ClinicalTrials.gov, First received Apr. 16, 2014, Last Updated Dec. 7, 2015, https://clinicaltrials.gov/ct2/show/NCT02122913.
Ni et al., "siRNA interference with a proliferation-inducing ligand gene in the Sgr-7901 gastric carcinoma cell line," Asian Pacific Journal of Cancer Prevention, 2012, 13:1511-1514.
NIH National Cancer Institute [online], "recurrence (ree-KER-ents)," NCI Dictionary of Cancer Terms, retrieved on Sep. 21, 2018, URL: <https://www.cancer.gov/publications/dictionaries/cancer-terms/def/recurrence>, 1 page.
NIH National Cancer Institute [online], "relapse (REE-laps)," NCI Dictionary of Cancer Terms, retrieved on Sep. 17, 2018, URL: <https://www.cancer.gov/publications/dictionaries/cancer-terms/def/relapse>, 1 page.
NIH National Cancer Institute [online], "progression (pru-GREH-shun)," NCI Dictionary of Cancer Terms, retrieved on Sep. 17, 2018, URL: <https://www.cancer.gov/publications/dictionaries/cancer-terms/def/progression>, 1 page.
NIH, "List of Cancer-causing Agents Grows," National Institute of Environmental Health Sciences, https://www.niehs.nih.gov/news/newsroom/releases/2005/january31/index.cfm, 4 pages.
Nikiforova et al., Abstract No. 5. Meeting Info: 84th Annual Meeting of the American Thyroid Association. Coronado, CA, United States, 2014.
Nollau et al., "Methods for detection of point mutations: performance and quality assessment. IFCC Scientific Division, Committee on Molecular Biology Techniques," Clin Chem. Jul. 1997;43(7):1114-28.
Obianyo et al., "Novel small molecule activators of the Trk family of receptor tyrosine kinases. Biochim Biophys Acta, 1834:2214-2218," Biochim Biophys Acta, Oct. 2013, 1834(10):2213-2218.
Oken et al., "Toxicity and response criteria of th Eastern Cooperative Oncology Group," Am J Clin Oncol, 1982, 5:649-655.
Olivier, "The Invader assay for SNP genotyping," Mutat Res, Jun. 3, 2005;573(1-2):103-10.
O'Shea, "Jaks, STATs, cytokine signal transduction, and immunoregulation: are we there yet?" Immunity, 1997, 7:1-11.
Otsubo et al., "Sporadic pediatric papillary thyroid carcinoma harboring the ETV6/NTRK3 fusion in oncogene in a 7-year-old Japanese girl: a case report and review of literature," J. Pediatr. Endocrinol. Metab. 28;31(4):461-467, 201.
Ott et al., "An immunogenic personal neoantigen vaccine for patients with melanoma.", Nature 547: 217-221, 2017.
Ou et al., "Emergence of novel and dominant acquired EGFR solvent-front mutations at Gly796 (G796S/R) together with C797S/R and L792F/H EGFR (L858R/T790M) NSCLC patient who progressed on osimertinib," Lung Cancer, 2017, 108: 228-231.
Ou et al., "Identification of a novel TMEM106B-ROS1 fusion variant in lung adenocarcinoma by comprehensive genomic profiling.", Lung Cancer, 88(3):352-4, 2015.
Ou et al., "Next-Generation Sequencing Reveals a Novel NSCLC ALK F1174V Mutation and Confirms ALK G1202R Mutation Confers High-Level Resistance to Alectinib (CH5424802/RO5424802) in ALK-Rearranged NSCLC Patients Who Progressed on Crizotinib," Journal of Thoracic Oncology, Apr. 2014, 9: 549-553.
Pan et al., Laboratory Investigation, vol. 96, Supp. Suppl. 1, pp. 367A, Abstract No. 1450, 105th Annual Meeting of the United States and Canadian Academy of Pathology, Seattle, WA, 2016.
Panagopoulos et al., "Recurrent fusion of the genes FN1 and ALK in gastrointestinal leiomyomas", Modern Pathology 29: 1415-1423, 2016.
Pao, W., et al. "Acquired resistance of lung adenocarcinomas to gefitinib or erlotinib is associated with a second mutation in the EGFR kinase domain," PLoS Med, Feb. 2005, 2(3), e73.
Papatsoris et al., "Manipulation of the nerve growth factor network in prostate cancer," Exper Opin Invest Drugs, 2007, 16(3):303-309.
Park et al., "NTRK1 fusions for the therapeutic intervention of Korean patients with colon cancer," Oncotarget. 7(7):8399-412, 2016.
Patani et al., "Bioisosterism: A rational approach in Drug Design," Chem Rev., Dec. 1996, 96(8):3147-3176.
Patapoutian et al., "Trk receptors: mediators of neurotrophin action," Current Opinion in Neurobiology, 2001, 11:272-280.
PCT International Preliminary Report on Patentability in International Application No. PCT/US2009/057729, dated Mar. 22, 2011, 7 pages.
PCT International Preliminary Report on Patentability in International Application No. PCT/US2009/061519, dated Apr. 26, 2011, 6 pages.
PCT International Preliminary Report on Patentability in International Application No. PCT/US2010/041538, dated Jan. 10, 2012, 7 pages.
PCT International Preliminary Report on Patentability in International Application No. PCT/US2011/036452, dated Nov. 29, 2012, 6 pages.
PCT International Preliminary Report on Patentability in International Application No. PCT/US2015/060953, dated May 16, 2017, 7 pages.
PCT International Preliminary Report on Patentability in International Application No. PCT/US2016/035327, dated Dec. 14, 2017, 9 pages.
PCT International Preliminary Report on Patentability in International Application No. PCT/US2016/058951, dated May 11, 2018, 11 pages.
PCT International Preliminary Report on Patentability in International Application No. PCT/US2017/033257, dated Nov. 20, 2018, 8 pages.
PCT International Preliminary Report on Patentability in International Appln. No. PCT/US/2017/058518, dated Apr. 30, 2019, 8 pages.
PCT International Search Report and Written Opinion in International Application No. PCT/US2009/0161519, dated Feb. 2, 2010, 8 pages.
PCT International Search Report and Written Opinion in International Application No. PCT/US2009/057729, dated Feb. 4, 2010, 10 pages.

(56) References Cited

OTHER PUBLICATIONS

PCT International Search Report and Written Opinion in International Application No. PCT/US2010/041538, dated Oct. 1, 2010, 10 pages.
PCT International Search Report and Written Opinion in International Application No. PCT/US2011/036452, dated Aug. 18, 2011, 9 pages.
PCT International Search Report and Written Opinion in International Application No. PCT/US2015/060953, dated Feb. 8, 2016, 12 pages.
PCT International Search Report and Written Opinion in International Application No. PCT/US2016/058951, dated Feb. 7, 2017, 20 pages.
PCT International Search Report and Written Opinion in International Application No. PCT/US2018/022833, dated Aug. 13, 2018.
PCT International Search Report and Written Opinion in International Application No. PCT/US2017/058518, dated May 2, 2018, 17 pages.
PCT International Search Report and Written Opinion in International Application No. PCT/US2018/039502, dated Apr. 16, 2018, 16 pages.
PCT International Search Report and Written Opinion in International Application No. PCT/US2018/057542, dated Mar. 6, 2019, 19 pages.
Perales et al., "Fast Cars and No Brakes: Autologous Stem Cell Transplantation as a Platform for Novel Immunotherapies," Biol Blood Marrow Transplant, Jan. 2016;22(1):17-22. doi: 10.1016/j.bbmt.2015.10.014. Epub Oct. 17, 2015.
Perez-Pinera et al., "The Trk tyrosine kinase inhibitor K252a regulates growth of lung adenocarcinomas," Molecular and Cellular Biochemistry, 2007, 295(1&2):19-26.
Perrault et al., "The Synthesis of N-Aryl-5(S)-aminomethyl-2-oxazolidinone Antibacterials and Derivatives in One Step from Aryl Carbamates," Org. Process Res. Dev., 2003, 7:533-546.
Peus et al., "Appraisal of the Karnofsky Performance Status and proposal of simple algorithmic system for its evaluation," BMC Med Infomr Decis Mak, 2013, 13:72.
Philippines Office Action in Philippines Application No. PH 1/2012/500048, dated May 30, 2014, 2 pages.
Picarsic et al., "Molecular characterization of sporadic pediatric thyroid carcinoma with the DNA/RNA ThyroSeq v2 next-generation sequencing assay," Pediatr. Dev. Pathol, Mar. 2016, 19(2):115-122.
Pierottia and Greco, "Oncogenic rearrangements of the NTRK1/NGF receptor," Cancer Letters, 2006, 232:90-98.
Pinedo et al., "Translational Research: The Role of VEGF in Tumor Angiogenesis," The Oncologist, 2000, 5(1): 1-2.
Pinski et al., "Trk receptor inhibition induces apoptosis of proliferating but not quiescent human.osteoblasts," Cancer Res, 2002, 62:986-989.
Plosker, "Sipuleucel-T: in metastatic castration-resistant prostate cancer.", Drugs 71(1): 101-108, 2011.
Ponsaerts et al., "Cancer immunotherapy using RNA-loaded dendritic cells," Clin. Exp. Immunol., Dec. 2003, 134:378-384.
Prabhakaran et al., "Novel TLE4-NTRK2 fusion in a ganglioglioma identified by array-CGH and confirmed by NGS: Potential for a gene targeted therapy," Neuropathology, Mar. 2018, doi:10.1111/neup.12458.
Prasad et al., "NTRK fusion oncogenes in pediatric papillary thyroid carcinoma in northeast United States," Cancer, Apr. 2016, 122(7):1097-1107.
PubChem, "Larotrectinib," https://pubchem.ncbi.nlm.nih.gov/compound/46188928, retrieved on Apr. 29, 2019, 20 pages.
Pulciani et al., "Oncogenes in solid human tumours," Nature, 1982, 300(5892):539-542.
Qaddoumi et al., "Genetic alterations in uncommon low-grade neuroepithelial tumors: BRAF, FGFR1, and MYB mutations occur at high frequency and align with morphology,"Acta Neuropathol, Jun. 2016, 131(6):833-845.

Qiu et al., "Next generation sequencing (NGS) in wild type GISTs", J Clin. Oneal. 35: 15 _suppl, e22507-e22507, 2017.
Ramer and Bisby, "Adrenergic innervation of rat sensory ganglia following proximal or distal painful sciatic neuropathy: distinct mechanisms revealed by anti-NGF treatment," Eur. J. Neurosci., 1999, 11:837-846.
Rausch et al., "mRNA vaccine CV9103 and CV9104 for the treatment of prostate cancer.", Human Vaccin Immunother 10(11): 3146-52, 2014.
Raychaudhuri et al., "K252a, a high-affinity nerve growth factor receptor blocker, improves psoriasis: an in vivo study using the severe combined immunodeficient mouse-human skin model," J. Investigative Dermatology, 2004, 122(3):812-819.
Reshmi et al., "Abstract 477: Genomic and Outcome Analyses of Philadelphia Chromosome like (Ph-like) NCI Standard Risk B-Acute Lymphoblastic Leukemia (SR B-ALL) Patients Treated on Children's Oncology Group (COG) AALL0331," Blood, 2017, 130(S1): 477.
Reungwetwattana et al., "Targeted therapies in development for non-small cell lung cancer," J Carcinog, Dec. 2013, 12:22, doi: 10.4103/1477-3163.123972. eCollection 2013.
Reuther et al., "Identification and characterization of an activating TrkA deletion mutation in acute myeloid leukemia," Mol. Cell. Biol. 2000, 20:8655-8666.
Ricarte-Filho et al., "Identification of kinase fusion oncogenes in post-Chernobyl radiation-induced thyroid cancers," J. Clin. Invest, Nov. 2013, 123(11): 4935-4944.
Ricci et al., Neurotrophins and neurotrophin receptors in human lung cancer, Am. J. Respiratory Cell and Molecular Biology, Oct. 2001, 25(4): 439-446.
Richard et al., "Syngeneic stem cell transplant for spent-phase polycythaemia vera: eradication of myelofibrosis and restoration of normal haematopoiesis," Br. J Haematol., Apr. 2002, 117(1):245-246.
Rimkunas et al., "Analysis of receptor tyrosine kinase ROS1-positive tumors in non-small cell lung cancer: identification of a FIG-ROS1 fusion.", Clin. Cancer Res., 18: 4449-58, 2012.
Ritterhouse et al., "ROS1 Rearrangement in Thyroid Cancer.", Thyroid, 26(6): 794-7, 2016.
Ro et al., "Effect of NGF and anti-NGF on neuropathic pain in rats following chronic constriction injury of the sciatic nerve," Pain, 1999, 79:265-274.
Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis," Acta Derm. Venereal., 2015, 95:542-548.
Rosenbaum et al., "Next Generation Sequencing Reveals Genomic Heterogenity of ALK Fusion Breakpoints in Non-Small Cell Lung Cancer", Laboratory Investigation, vol. 96, Supp. Suppl. 1, pp. 481A-482A, Abstract No. 1914, 105th Annual Meeting of the United States and Canadian Academy of Pathology, Seattle, WA, 2016.
Roskoski, Jr. et al., "Classification of small molecule protein kinase inhibitors based upon The structures of their drug-enzyme complexes," Pharmacological Research, 2016, 103: 26-48.
Ross et al., "New routes to targeted therapy of intrahepatic cholangiocarcinomas revealed by next-generation sequencing," Oncologist, 2014, 19:235-242.
Rossi et al., "Abstract 84: RNA-Sequencing Identifies ETV6-NTRAK3 as a Gene Fusion Involved in Gastrointestinal Stromal Tumors," Meeting Info: 105th Annual Meeting of the United States and Canadian Academy of Pathology, Seattle, WA, Annual Meeting Abstracts, 24A.
Rubin et al., "Congenital mesoblastic nephroma t(12;15) is associated with ETV6-NTRK3 gene fusion: cytogenetic and molecular relationship to congenital (infantile) fibrosarcoma," Am. J. Pathol, Nov. 1998, 153(5):1451-1458.
Russo et al., "Acquired Resistance to the Trk Inhibitor Entrectinib in Colorectal Cancer," Cancer Discovery, Jan. 1, 2016, 6(1):36-44.
Rutkowski et al., "Treatment of advanced dermatofibrosarcoma protuberans with imatinib mesylate with or without surgical resection," J. Eur. Acad. Dermatol. Venereol., 2011, 25:264-270.

(56) References Cited

OTHER PUBLICATIONS

Saborowski et al., "Mouse model of intrahepatic cholangiocarcinoma validates FIG-ROS as a potent fusion oncogene and therapeutic target.", Proc. Natl. Acad Sci. USA., 110(48): 19513-19518, 2013.
Sahin et al., "Personalized RNA mutanome vaccines mobilize poly-specific therapeutic immunity against cancer.", Nature 547: 222-226, 2017.
Santoro et al., "Doxorubicin versus CYVADIC versus doxorubicin plus ifosfamide in first-line treatment of advanced soft tissue sarcomas: a randomized study of the European Organization for Reasearh and Treatment of Cancer Soft Tissue and Bone Sarcoma Group," J. Clin Oncol., 1995, 13(7):1537-1545.
Saragovi et al., "A TrkA-selective, fast internalizing nerve growth factor-antibody complex induces trophic but not neuritogenic signals," J Biol Chem, Dec. 25, 1998;273(52):34933-34940.
Sartore-Bianchi et al., "Sensitivity to Entrectinib Associated With a Novel LMNA-NTRK1 Gene Fusion in Metastatic Colorectal Cancer," J. Natl. Cancer Inst, Nov. 2015, 108(1). doi: 10.1093/jnci/djv306.
Schmidt et al., "Heilmittelchemische untersuchungen in der Heterocyclischen Rihe. Pyrazolo-(3,4-D)-Pyrimidine (Medicinal chemical studies in the heterocyclic series.Pyrazolo-(3,4-D)-Pyrimidine)," Helvetica Chimica, Verlag Helvetica Chimica Acta, Jan. 1956, 39: 986-991 (with English Abstract).
Schram et al., "Abstract LB-302: Potential role of larotrectinib (LOXO-101), a selective pan-TRK inhibitor, in NTRK fusion-positive recurrent glioblastoma,"Cancer Research, Jul. 2017, DOI: 10.1158/1538-7445.AM2017-LB-302, 2 pages.
Schrock et al., "Gastrointestinal tumours, non-colorectal", Annals of Oncology. vol. 27, Suppl 6, 6130, 2016.
Shaver et al., "Diverse, Biologically Relevant, and Targetable Gene Rearrangements in Triple-Negative Breast Cancer and Other Malignancies.", Cancer Res, 76(16): 4850-60, 2016.
Shaw et al., "Ceritinib in ALK-rearranged non-small-cell lung cancer.", New Engl. J Med 370: 1189-1197, 2014.
Shaw et al., "Crizotinib in ROS1-rearranged non-small-cell lung cancer.", New Engl. J Med 371: 1963-1971, 2014.
Sheldrick, "A short history of SHELX," Acta Crystallogr A, Jan. 2008, 64(Pt1): 112-122.
Shelton et al., "Nerve growth factor mediates hyperalgesia and cachexia in auto-immune arthritis," Pain, 2005, 116:8-16.
Sigal, et al., "Activity of Entrectinib in a Patient With the First Reported NTRK Fusion in Neuroendocrine Cancer," J. Natl. Compr. Canc. Netw, Nov. 2017, 15(11): 1317-1322.
Silverman, The Organic Chemistry of Drug Design and Drug Action, Second Edition, 2007, 20-21.
Sims et al., Abstract P280: Profiling abscopal regression in a pediatric fibrosarcoma with a novel EML4-NTRK3 fusion using immunogenomics and high-dimensional histopathology, J mmunotherapy of Cancer, Nov. 2016, 4(S1): 73.
Skálová et al., "Mammary Analogue Secretory Carcinoma of Salivary Glands. Molecular Analysis of 25 ETV6 Gene Rearranged Tumors With Lack of Detection of Classical ETV6-NTRK3 Fusion Transcript by Standard RT-PCR: Report of 4 Cases Harboring ETV6-X Gene Fusion," Am. J. Surg. Pathol, Jan. 2016, 40(1):3-13.
Skalova et al., "Molecular Profiling of Mammary Analog Secretory Carcinoma Revealed a Subset of Tumors Harboring a Novel ETV6-RET Translocation: Report of 10 Cases," Am. J. Surg. Pathol, Feb. 2018, 42(2):234-246.
Skalova et al., "Newly described salivary gland tumors," Modern Pathology, Jan. 2017, 30(s1): S27-S43.
Sleijfer et al., "Prognostic and predictive factors for outcome to firs-line ifosfamide-containing chemotherapy for adult patients with advanced soft tissue sarcomas:an exploratory, retrospective analysis on large series from the European Organization for Research and Treatment of Cancer-Soft Tissue and Bone Sarcoma Group," Eur J. Cancer, 2010, 46(1):72-83.
Sleijfer et al., "Using single-agent therapy in adult patients with advanced soft tissue sarcoma can still be considered standard care," Oncologist, 2005, 10(10):833-841.

Smith et al., "Annotation of human cancers with EGFR signaling-associated protein complexes using proximity ligation assays," Sci Signal, 2015, 8(359):ra4, 12 pages.
Sohrabji et al., "Estrogen-BDNF interactions: implications for neurodegenerative diseases," Frontiers in Neuroendocrinology, 2006, 27(4):404-414.
Song et al., "Molecular Changes Associated with Acquired Resistance to Crizotinib in ROS1-Rearranged Non-Small Cell Lung Cancer.", Clin. Cancer Res., 21(10): 2379-87, 2015.
Stephens et al., "TRK receptors use redundant signal transduction pathways involving SHC and PLC-gamma 1 to mediate NGF responses," Neuron, Mar. 1994, 12(3):691-705.
Stransky et al., "The landscape of kinase fusions in cancer," Nature comm., 2014, 5:4846.
Subramaniam et al., Abstract 2019: RNA-Seq analysis of glioma tumors to reveal targetable gene fusions, 2017 Annual Meeting of the American Society of Clinical Oncology,2017, 1 page.
Sun et al., "P-loop conformation governed crizotinib resistance in G2032R-mutated ROS1 tyrosine kinase: clues from free energy landscape," PLoS computational biology, Jul. 17, 2014, 10(7):e1003729.
Tacconelli et al., "TrkA alternative splicing: a regulated tumor-promoting switch in human neuroblastoma," Cancer Cell, 2004, 6:347-360.
Tafinlar, Highlights of Prescribing Information, GlaxoSmithKline, Jan. 2014, 41 pages.
Tahira et al., "dbQSNP. A database of SNPs in human promoter regions with allele frequency information determined by single-strand conformation polymorphism-based methods," Hum Mutat, Aug. 2005;26(2):69-77.
Taipale et al., "Chaperones as thermodynamic sensors of drug-target interactions reveal kinase inhibitor specifities in living cells," Nat Biotech, 2013, 31(7):630-637.
Taiwan Office Action in Taiwan Application No. 098135670, dated Jan. 20, 2014, 7 pages (with English Translation).
Taiwan Search Report in Taiwan Application No. 098132033, dated Dec. 13, 2013, 1 page (English translation only).
Tan et al., "Genetic landscape of ALK+ non-small cell lung cancer (NSCLC) patients (pts) and response to ceritinib in ASCEND-1", J Clin. Oncology, vol. 34, Supp. Supplement 15, Abstract No. 9064, 2016 Annual Meeting of the American Society of Clinical Oncology, Chicago, IL, 2016.
Tannenbaum, et al., "Abstract 749: Characterization of a Novel Fusion Gene, EML4-NTRK3, in Infantile Fibrosarcoma," Pediatr Blood Cancer, DOI 10.1002/pbc, 1 page.
Taylor et al., "Abstract 794: Characterization of NTRK fusions and Therapeutic Response to NTRK Inhibition in Hematologic Malignancies," Blood, 2017, 130: 794.
The Cancer Genome Atlas Network, "Comprehensive Molecular Characterization of Human colon and Rectal Cancer," Nature, Jan. 2013, 487(7407): 330-337.
Theodosiou et al., "Hyperalgesia due to nerve damage: role of nerve growth factor," Pain, 1999, 81:245-255.
Thompson et al., "Brain-derived neurotrophic factor is an endogenous modulator of nociceptive responses in the spinal cord," Proc. Natl. Acad. Sci. USA, 1999, 96:7714-7718.
Thress et al., "Identification and preclinical characterization of AZ-23, a novel, selective, and orally bioavailable inhibitor of the Trk kinase pathway," Mol Cancer Ther, Jul. 2009;8(7):1818-27. doi: 10.1158/1535-7163.MCT-09-0036. Epub Jun. 9, 2009.
Truzzi et al., "Neurotrophins and their receptors stimulate melanoma cell proliferation and migration," J. Investigative Dermatology, 2008, 128(8):2031-2040.
Truzzi et al., "Neurotrophins in healthy and diseased skin ," Dermato-Endrocrinology, 2008, 3(1):32-36.
Turtle et al., "Artificial antigen-presenting cells for use in adoptive immunotherapy," Cancer J, Jul.-Aug. 2010;16(4):374-81. doi: 10.1097/PPO.0b013e3181eb33a6.
Vaishnavi et al., "Oncogenic and drug-sensitive NTRK1 rearrangements in lung cancer.", Nature Med 19: 1469-1472, 2013.
Vaishnavi et al., "TRKing Down an Old Oncogene in a New Era of Targeted Therapy," Cancer Discovery, Jan. 2015, 5(1):25-34.
Vaishnavi et al., "Oncogenic and drug-sensitive NTRK1 rearrangements in lung cancer," Nature Med., 2013, 19:1469-1472.

(56) References Cited

OTHER PUBLICATIONS

Van Gurp et al., "Phase 1 dose-escalation study of CP-690 550 in stable renal allograft recipients: preliminary findings of safety, tolerability, effects on lymphocyte subsets and pharmacokinetics," Am. J. Transpl., 2008, 8:1711-1718.
Van Noesel et al., "Pediatric neuroblastomas: genetic and epigenetic 'danse macabre'," Gene, 2004, 325:1-15.
Vanden et al., "endocrine and neuroendocrine tumours", Annals of Oncology, vol. 27, Supp Supplement 6. Abstract No. 427PD' 4pt European Society for Medical Oncology Congress, ESMO 2016; Copenhagen, Denmark; Oct. 7-11, 2016.
Vippagunta et al., "Crystalline Solids" Advanced Drug Delivery Rev., 2001, 48(1): 3-26.
Vogelstein and Kinzler, The Genetic Basis of Human Cancer, 2nd ed., 2002, p. 3, col. 1, para 2.
Wadhwa et al., "Expression of the neurotrophin receptors Trk A and Trk B in adult human astrocytoma and glioblastoma," Journal of Biosciences, 2003, 28(2):181-188.
Walch et al., "Role of neurotrophins and neurotrophins receptors in the in vitro invasion and heparanase production of human prostate cancer cells," Clin. Exp. Metastasis, 1999, 17:307-314.
Walther et al., "Cytogenetic and single nucleotide polymorphism array findings in soft tissue tumors in infants," Cancer Genet, Jul.-Aug. 2013, 206(7-8): 299-303.
Wang et al., "Identification of NTRK3 fusions in childhood melanocytic neoplasms," J. Mol. Diagn, May 2017, 19(3):387-396.
Wang et al., "Design, synthesis and biological evaluation of novel 4-arylaminopyrimidine derivatives possessing a hydrazone moiety as dual inhibitors of L1196M ALK and ROS1.", Eur. J Med Chem., 123, 80-99, 2016.
Wang et al., "Identification of 4-aminopyrazolylpyrimidines as potent inhibitors of Trk kinases," J Med Chem, Aug. 14, 2008;51(15):4672-84. doi: 10.1021/jm800343j. Epub Jul. 23, 2008.
Wang et al., "T cells sensitized with breast tumor progenitor cell vaccine have therapeutic activity against spontaneous HER2/neu tumors," Breast Cancer Res Treat, Jul. 2012;134(1):61-70. doi: 10.1007/s10549-011-1912-5. Epub Dec. 16, 2011.
Wang et al., "Trk kinase inhibitors as new treatments for cancer and pain," Expert Opin. Ther Patents, Mar. 2009, 19(3):305-319.
Wang, "Pan-cancer analysis of ROS1 genomic aberrations", University of Hong Kong, Pokfulam, Hong Kong SAR (Thesis), 44 pages, 2015.
Watanbe et al., "Cryptic t(12;15)(p13;q26) producing the ETV6-NTRK3 fusion gene and no loss of IGF2 imprinting in congenital mesoblastic nephroma with trisomy 11: fluorescence in situ hybridization and IGF2 allelic expression analysis," Cancer Genet. Cytogenet, Jul. 2002, 136(1):1016.
Wei et al., "Abstract #2136: Entrectinib is Effective Against the Gatekeeper and Other Emerging Resistance Mutations in NTRK-, ROS1- and ALK- Rearranged Cancers," Poster, Presented at Proceedings of the 107th Annual Meeting of the American Association for Cancer Research, New Orleans LA, Apr. 16-20, 2016; Cancer Res, Jul. 2016, 76(14): 1 page.
Wei et al., "Abstract 78: Entrectinib, a highly potent pan-Trk, and ALK inhibitor, has broad-spectrum, histology-agnostic anti-tumor activity in molecularly defined cancers," 28th EORTC-NCI-AACR Symposium on Molecular Targets and Cancer Therapeutics, Munich, Germany, 2016, 1 page.
Wen et al, "Updated response assessment criteria for high-grade gliomas: response assessment in neuro-oncology working group," J Clin Oncol, Apr. 2010, 28(11): 1963-1972.
Wiesner et al., "Kinase fusions are frequent in Spitz tumours and spitzoid melanomas," Nature Comm., 2014, 5:3116.
Winski et al., "LOXO-101, a pan-TRK inhibitor, for the treatment of TRK-driven cancers," 26th EORTC-NCI-AACR Symposium on Molecular Targets and Cancer Therapeutics, Barcelona, Spain, 2014, 175.
Wittwer et al., "High-resolution genotyping by amplicon melting analysis using LCGreen," Clin Chem, Jun. 2003;49(6 Pt 1):853-60.

Wlodarska et al., "ALK-Positive Anaplastic Large Cell Lymphoma with the Variant EEF1G-, RNF213- and Atic-ALK Fusions is Featured by Copy Number Gain of the Rearranged ALK Gene", Blood, vol. 126(23): 3654, 57th Annual Meeting of the American Society of Hematology, San Diego, CA, 2015.
Won et al., "Post-crizotinib management of effective ceritinib therapy in a patient with ALK-positive non-small cell lung cancer", BMC Cancer, 16: 568, 2016.
Woodward, "Bi-allelic SNP genotyping using the TaqMan® assay," Methods Mol Biol., 2014;1145:67-74. doi: 10.1007/978-1-4939-0446-4_6.
Woolf et al., "Letter to Neuroscience: Nerve Growth Factor Contributes to the Generation of Inflammatory Sensory Hypersensitivity," Neuroscience, 1994, 62:327-331.
Wu et al., "The genomic landscape of diffuse intrinsic pontine glioma and pediatric non-brainstem high-grade glioma," Nature Genetics, 2014, 444-450.
Xalkori, Highlights of Prescribing Information, Pfizer Labs, Initial approval 2011, revised Mar. 2016, 20 pages.
Yakirevich et al., "Colorectal Adenocarcinoma with ALK Rearrangement: Clinicopathologic and Molecular Characteristics", Laboratory Investigation, vol. 96, Supp. Suppl. 1, pp. 209A, Abstract No. 827, 105th Annual Meeting of the United States and Canadian Academy of Pathology, Seattle, WA, 2016.
Yakirevich et al., "Oncogenic ALK Fusion in Rare and Aggressive Subtype of Colorectal Adenocarcinoma as a Potential Therapeutic Target.", Clin Cancer Res, 22(15): 3831-40, 2016.
Yamamoto et al., "ALK, ROS1 and NTRK3 gene rearrangements in inflammatory myofibroblastic tumours.", Histopathology, 69(1): 72-83, 2016.
Yamamoto et al., "Anaplastic lymphoma kinase-positive squamous cell carcinoma of the lung: A case report.", Mal Clin. Oneal. 5(1): 61-63, 2016.
Yilmaz et al., "Theraputic targeting of Trk supresses tumor proliferation and enhances cisplatin activity in HNSCC," Cancer Biology and Therapy, 2010, 10(6):644-653.
Ying et al., "Atypical negative ALK FISH accompanied by immunohistochemistry positivity harbored various ALK rearrangements in NSCLC patients and respond to targeted therapy.", J Clin. Oncology, vol. 34, Supp. Supplement 15, Abstract No. e20506, 2016 Annual Meeting of the American Society of Clinical Oncology, Chicago, IL, 2016.
Yu et al., "Denaturing high performance liquid chromatography: high throughput mutation screening in familial hypertrophic cardiomyopathy and SNP genotyping in motor neurone disease," J ClinPathol, May 2005;58(5):479-85.
Yu et al., "Detection of Alk rearrangements in lung cancer patients using a homebrew PCR assay", Oncotarget, 8(5): 7722-7728, 2016.
Zage et al., "The selective Trk inhibitor AZ623 inhibits brain-derived neurotrophic factor—mediated neuroblastoma cell proliferation and signaling and is synergistic with topotecan," Cancer, Mar. 2011, 117(6): 1321-1391.
Zahn et al., "Effect of blockade of nerve growth factor and tumor necrosis factor on pain behaviors after plantar incision," J. Pain, 2004, 5:157-163.
Zehir et al., "Mutational landscape of metastatic cancer revealed from prospective clinical sequencing of 10,000 patients," Nat. Med, Jun. 2017, 23(6):703-713.
Zelboraf, Highlights of Prescribing Information, Genentech USA, Initial Approval 2011, revised Aug. 2015, 18 pages.
Zhang et al., "A novel multiplex tetra-primer ARMS-PCR for the simultaneous genotyping of six single nucleotide polymorphisms associated with female cancers," PLoS One, Apr. 17, 2013;8(4):e62126. doi: 10.1371/journal.pone.0062126. Print 2013.
Zhang et al., "Expression of nerve growth factor receptors and their prognostic value in human pancreatic cancer," Oncology Reports, 2005, 14:161-171.
Zhang et al., "Whole-genome sequencing identifies genetic alterations in pediatric low-grade gliomas," Nat. Genet., Jun. 2013, 45(6): 602-612.
Zheng et al., "Anchored multiplex PCR for targeted next-generation sequencing," Nature Med., Dec. 2014, 20(12):1479-1486.

(56) References Cited

OTHER PUBLICATIONS

Zhu et al., "TPD52L1-ROS1, a new ROS1 fusion variant in lung adenosquamous cellcarcinoma identified by comprehensive genomic profiling", Lung Cancer, 97:48-50, doi: 10.1016/j.lungcan.2016.04. 013, 2012.
Ziemiecki et al., "Oncogenic activation of the human trk proto-oncogene by recombination with the ribosomal large subunit protein L7a," EMBO J, Jan. 1990, 9(1):191-196.
Zou et al., "PF-06463922 is a potent and selective next-generation ROS1/ALK inhibitor capable of blocking crizotinib-resistant ROS1 mutations.", Proc. Natl. Acad Sci. USA., 112(11): 3493-8, 2015.
U.S. Appl. No. 13/382,858, filed Jan. 6, 2012, Shelley Allen.
U.S. Appl. No. 14/321,246, filed Jul. 1, 2014, Shelley Allen.
U.S. Appl. No. 15/401,895, filed Jan. 9, 2017, Shelley Allen.
U.S. Appl. No. 15/401,913, filed Jan. 9, 2017, Shelley Allen.
U.S. Appl. No. 15/724,601, filed Oct. 4, 2017, Shelley Allen.
U.S. Appl. No. 13/063,894, filed Mar. 14, 2011, Steven W. Andrews.
U.S. Appl. No. 13/614,968, filed Sep. 13, 2012, Steven W. Andrews.
U.S. Appl. No. 14/984,353, filed Dec. 30, 2015, Steven W. Andrews.
U.S. Appl. No. 15/401,792, filed Jan. 9, 2017, Steven W. Andrews.
U.S. Appl. No. 15/401,969, filed Jan. 9, 2017, Steven W. Andrews.
U.S. Appl. No. 13/698,922, filed Nov. 19, 2012, Steven W. Andrews.
U.S. Appl. No. 14/575,663, filed Dec. 18, 2014, Steven W. Andrews.
U.S. Appl. No. 15/350,888, filed Nov. 14, 2016, Steven W. Andrews.
U.S. Appl. No. 15/401,839, filed Jan. 9, 2017, Steven W. Andrews.
U.S. Appl. No. 15/401,952, filed Jan. 9, 2017, Steven W. Andrews.
U.S. Appl. No. 15/632,187, filed Jun. 23, 2017, Steven W. Andrews.
U.S. Appl. No. 15/900,019, filed Feb. 20, 2018, Steven W. Andrews.
U.S. Appl. No. 13/125,263, filed Apr. 20, 2011, Julia Haas.
U.S. Appl. No. 13/943,590, filed Jul. 16, 2013, Julia Haas.
U.S. Appl. No. 14/490,460, filed Sep. 18, 2014, Julia Haas.
U.S. Appl. No. 14/596,611, filed Jan. 14, 2015, Julia Haas.
U.S. Appl. No. 14/846,166, filed Sep. 4, 2015, Julia Haas.
U.S. Appl. No. 15/399,389, filed Jan. 5, 2017, Julia Haas.
U.S. Appl. No. 15/860,948, filed Jan. 3, 2018, Julia Haas
U.S. Appl. No. 16/044,653, filed Jul. 25, 2018, Julia Haas.
U.S. Appl. No. 14/943,014, filed Nov. 16, 2015, Alisha B. Arrigo.
U.S. Appl. No. 15/399,207, filed Jan. 5, 2017, Alisha B. Arrigo.
U.S. Appl. No. 15/706,062, filed Sep. 15, 2017, Alisha B. Arrigo.
U.S. Appl. No. 15/872,769, filed Jan. 16, 2018, Alisha B. Arrigo.
U.S. Appl. No. 16/199,818, filed Nov. 26, 2018, Steven W. Andrews.
U.S. Appl. No. 16/199,867, filed Nov. 26, 2018, Steven W. Andrews.
U.S. Appl. No. 16/199,875, filed Nov. 26, 2018, Steven W. Andrews.
U.S. Appl. No. 15/335,378, filed Oct. 26, 2016, Nisha Nanda.
U.S. Appl. No. 15/785,174, filed Oct. 16, 2017, Nisha Nanda.
U.S. Appl. No. 15/785,228, filed Oct. 16, 2017, Nisha Nanda.
U.S. Appl. No. 15/785,218, filed Oct. 16, 2017, Nisha Nanda.
U.S. Appl. No. 15/860,789, filed Jan. 3, 2018, Nisha Nanda
U.S. Appl. No. 16/302,312, filed Nov. 16, 2018, Mark Reynolds.
U.S. Appl. No. 16/170,976, filed Oct. 25, 2018, Zhao.
U.S. Appl. No. 15/579,007, filed Dec. 1, 2017, Tuch et al.
U.S. Appl. No. 15/622,388, filed Jun. 14, 2017, Michael Cox.
U.S. Appl. No. 15/861,017, filed Jan. 3, 2018, Michael Cox.
U.S. Appl. No. 15/622,544, filed Jun. 14, 2017, Mark Reynolds.
U.S. Appl. No. 16/199,739, filed Nov. 26, 2018, Mark Reynolds.
American Association for Cancer Research, "TRK Inhibitor Shows Early Promise," Cancer Discovery, 6(1), Jan 1, 2016, XP009194480.
Bailey, Justin J., et al. "Tropomyosin receptor kinase inhibitors: an updated patent review for 2010-2016—Part II." *Expert opinion on therapeutic patents* 27.7 (2017): 831-849.
Extended European Search Report in European Application No. 18208279.2, dated Jun. 27, 2019, 10 pages.
PCT International Search Report and Written Opinion in International Application No. PCT/US2019/024961, dated Jul. 23, 2019, 13 pages.
Schmidt, Charles. "Combinations on trial." Nature 552.7685 (Dec. 21, 2017): S67-S69.
U.S. Appl. No. 13/125,263, filed Oct. 21, 2009, Issued.
U.S. Appl. No. 13/943,590, filed Jul. 16, 2013, Issued.
U.S. Appl. No. 14/490,460, filed Sep. 18, 2014, Issued.
U.S. Appl. No. 14/596,611, filed Jan. 14, 2015, Issued.
U.S. Appl. No. 14/846,166, filed Sep. 4, 2015, Issued.
U.S. Appl. No. 15/399,389, filed Jan. 5, 2017, Issued.
U.S. Appl. No. 15/860,948, filed Jan. 3, 2018, Issued.
U.S. Appl. No. 16/044,653, filed Jul. 25, 2018, Published.
U.S. Appl. No. 14/943,014, filed Nov. 16, 2015, Published.
U.S. Appl. No. 15/399,207, filed Jan. 5, 2017, Issued.
U.S. Appl. No. 15/706,062, filed Sep. 15, 2017, Issued.
U.S. Appl. No. 15/872,769, filed Jan. 16, 2018, Issued.
U.S. Appl. No. 16/366,368, filed Mar. 27, 2019, Pending.
U.S. Appl. No. 16/302,312, filed May 18, 2017, Published.
U.S. Appl. No. 15/579,007, filed Jun. 1, 2016, Published.
U.S. Appl. No. 15/622,388, filed Apr. 4, 2017, Issued.
U.S. Appl. No. 15/861,017, filed Jan. 3, 2018, Published.
U.S. Appl. No. 15/622,544, filed Apr. 4, 2017, Issued.
U.S. Appl. No. 16/199,739, filed Nov. 26, 2018, Published.
U.S. Appl. No. 13/698,922, filed May 13, 2011, Issued.
U.S. Appl. No. 14/575,663, filed Dec. 18, 2014, Issued.
U.S. Appl. No. 15/350,888, filed Nov. 14, 2016, Issued.
U.S. Appl. No. 15/401,839, filed Jan. 9, 2017, Issued.
U.S. Appl. No. 15/632,187, filed Jun. 23, 2017, Issued.
U.S. Appl. No. 15/900,019, filed Feb 20, 2018, Allowed.
U.S. Appl. No. 15/401,952, filed Jan. 9, 2017, Issued.
U.S. Appl. No. 13/063,894, filed Sep. 21, 2009, Issued.
U.S. Appl. No. 13/614,968, filed Sep. 13, 2012, Issued.
U.S. Appl. No. 14/984,353, filed Dec. 30, 2015, Issued.
U.S. Appl. No. 15/401,792, filed Jan. 9, 2017, Issued.
U.S. Appl. No. 15/401,969, filed Jan. 9, 2017, Issued.
U.S. Appl. No. 16/025,281, filed Jul. 2, 2018, Published.
U.S. Appl. No. 16/170,976, filed Oct. 25, 2018, Pending.
U.S. Appl. No. 15/335,378, filed Oct. 26, 2016, Published.
U.S. Appl. No. 15/785,174, filed Oct. 16, 2017, Allowed.
U.S. Appl. No. 15/785,218, filed Oct. 16, 2017, Published.
U.S. Appl. No. 15/860,789, filed Jan. 3, 2018, Published.
U.S. Appl. No. 15/785,228, filed Oct. 16, 2017, Allowed.
U.S. Appl. No. 16/199,818, filed Nov. 26, 2018, Pending.
U.S. Appl. No. 16/199,867, filed Nov. 26, 2018, Published.
U.S. Appl. No. 16/199,875, filed Nov. 26, 2018, Published.
U.S. Appl. No. 13/382,858, filed Jul. 9, 2010, Issued.
U.S. Appl. No. 14/321,246, filed Jul. 1, 2014, Issued.
U.S. Appl. No. 15/401,895, filed Jan. 9, 2017, Issued.
U.S. Appl. No. 15/401,913, filed Jan. 9, 2017, Issued.
U.S. Appl. No. 15/724,601, filed Oct. 4, 2017, Issued.
U.S. Appl. No. 16/377,514, filed Apr. 8, 2019, Pending.
U.S. Appl. No. 16/345,571, filed Oct. 26, 2017, Pending.

* cited by examiner

METHOD OF TREATMENT USING SUBSTITUTED IMIDAZO[1,2B]PYRIDAZINE COMPOUNDS

This application is a Continuation of U.S. patent application Ser. No. 13/063,894, which is a 371 National Stage filing of PCT/US2009/057729 filed Sep. 21, 2009, which claims priority to U.S. Provisional Application Ser. No. 61/099,030 filed Sep. 22, 2008, each of which is incorporated herein in its entirety.

The present invention relates to novel compounds, to pharmaceutical compositions comprising the compounds, to a process for making the compounds and to the use of the compounds in therapy. More particularly, it relates to certain substituted imidazo[1,2-b]pyridazine compounds which exhibit Trk family protein tyrosine kinase inhibition, and which are useful in the treatment of pain, inflammation, cancer and certain infectious diseases.

The current treatment regimes for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members—TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's arc widely expressed in neuronal tissue and are implicated in the maintenance, signaling and survival of neuronal cells (Patapoutian, A. et al., Current Opinion in Neurobiology, 2001, 11, 272-280).

Inhibitors of the Trk/neurotrophin pathway have been demonstrated to be effective in numerous pre-clinical animal models of pain. For example, antagonistic TrkA/NGF pathway antibodies (for example, RN-624) have been shown to be efficacious in inflammatory and neuropathic pain animal models and in human clinical trials (Woolf, C. J. et al. (1994) *Neuroscience* 62,327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *Neuroreport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448). Additionally, recent literature indicates after inflammation, BDNF levels and TrkB signaling is increased in the dorsal root ganglion (Cho, L. et al. Brain Research 1997, 749, 358) and several studies have show antibodies that decrease signaling through the BDNF/TrkB pathway inhibit neuronal hypersensitization and the associated pain (Chang-Qi, L et al. Molecular Pain 2008, 4:27)

In addition it was shown that tumor cells and tumor invading macrophages secret NGF which directly stimulates TrkA located on peripheral pain fibers. Using various tumor models in both mouse and rats it was demonstrated that neutralizing NGF with a monoclonal antibody inhibits cancer related pain to a degree similar or superior to the highest tolerated dose of morphine. Therefore, an inhibitor of TrkA can be used in the treatment of pain, including pain associated with cancer.

Recent literature has also shown that overexpression, activation, amplification and/or mutation of Trks are associated with many cancers including neuroblastoma (Brodeur, G. M., Nat. Rev. Cancer 2003, 3, 203-216), ovarian cancer (Davidson. B., et al., Clin. Cancer Res. 2003, 9, 2248-2259), breast cancer (Kruettgen et al, Brain Pathology 2006, 16: 304-310), prostate cancer (Dionne et al, Clin. Cancer Res. 1998, 4(8): 1887-1898), pancreatic cancer (Dang et al, Journal of Gastroenterology and Hepatology 2006, 21(5): 850-858), multiple myeloma (Hu et al, Cancer Genetics and Cytogenetics 2007, 178: 1-10), astrocytoma and medulloblastoma (Kruettgen et al, Brain Pathology 2006, 16: 304-310) glioma (Hansen et al, Journal of Neurochemistry 2007, 103: 259-275), melanoma (Truzzi et al, Journal of Investigative Dermatology 2008, 128(8): 2031-2040, thyroid carcinoma (Brzezianska et al, Neuroendocrinology Letters 2007, 28(3), 221-229.), lung adenocarcinoma (Perez-Pinera et al, Molecular and Cellular Biochemistry 2007, 295(1&2), 19-26), large cell neuroendocrine tumors (Marchetti et al, Human Mutation 2008, 29(5), 609-616), and colorectal cancer (Bardelli, A., Science 2003, 300, 949). In preclinical models of cancer, non-selective small molecule inhibitors of Trk A, B and C and Trk/Fc chimeras were efficacious in both inhibiting tumor growth and stopping tumor metastasis (Nakagawara, A. (2001) *Cancer Letters* 169:107-114; Meyer, J. et al. (2007) *Leukemia,* 1-10; Pierottia, M. A. and Greco A., (2006) *Cancer Letters* 232:90-98; Eric Adriaenssens, E. et al. *Cancer Res* (2008) 68:(2) 346-351) (Truzzi et al, Journal of Investigative Dermatology 2008, 128(8): 2031-2040.

In addition, inhibition of the neurotrophin/Trk pathway has been shown to be effective in treatment of pre-clinical models of inflammatory disease. For example inhibition of the neurotrophin/Trk pathway has been implicated preclinical models of inflammatory lung disease including asthma (Freund-Michel, V; Frossard, N.; *Pharmacology & Therapeutics* (2008), 117(1), 52-76), interstitial cystitis (Hu Vivian Y; et. al. *The Journal of Urology* (2005), 173(3), 1016-21), inflammatory bowel disease including ulcerative colitis and Crohn's disease (Di Mola, F. F, et. al., Gut (2000), 46(5), 670-678) and inflammatory skin diseases such as atopic dermatitis (Dou, Y.-C.; et. al. *Archives of Dermatological Research* (2006), 298(1), 31-37), eczema and psoriasis (Raychaudhuri, S. P.; et. al. Journal of Investigative Dermatology (2004), 122(3), 812-819).

The neurotrophin/Trk pathway, particularly BDNF/TrkB, has also been implicated in the etiology neurodegenerative diseases including multiple sclerosis, Parkinson's disease and Alzheimer's disease (Sohrabji, Farida; Lewis, Danielle K. Frontiers in Neuroendocrinology (2006), 27(4), 404-414). Modulation of the neutrophin/Trk pathway may have utility in treatment of these and related diseases.

The TrkA receptor is also thought to be critical to the disease process in the infection of the parasitic infection of *Typanosoma cruzi* (Chagas disease) in human hosts (de Melo-Jorge, M. et al. *Cell Host & Microbe* (2007), 1(4), 251-261). Thus, TrkA inhibition my have utility in treating Chagas disease and related protozoan infections.

Trk inhibitors may also find use in treating disease related to an imbalance of the regulation of bone remodeling, such as osteoporosis, rheumatoid arthritis and bone metastases. Bone metastases are a frequent complication of cancer, occurring in up to 70 percent of patients with advanced breast or prostate cancer(1) and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA and TrkC receptors has been observed in the bone forming area in mouse models of bone fracture (K. Asaumi, et al., Bone (2000) 26(6) 625-633). In addition, localization of NGF was observed in almost all bone forming cells (K. Asaumi, et al.). Recently, it was demonstrated that a pan-Trk inhibitor inhibits the tyrosine signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Several classes of small molecule inhibitors of Trk kinases said to be useful for treating pain or cancer are known (*Expert Opin. Ther. Patents* (2009) 19(3)). International Patent Application Publications WO 2006/115452 and WO 2006/087538 describe several classes of small molecules said to be inhibitors or Trk kinases which could be useful for treating pain or cancer.

U.S. Patent Publication number 2007/025540 discloses certain substituted imidazo[1,2b]pyridazines having a secondary amino group or a BOC-protected piperazinyl group at the 6-position. These compounds are disclosed as being inhibitors of the protein kinase C (PKC).

International Publication No. WO 2008/052734 discloses (R)-4-(6-(2-(3-fluorophenyl)pyrrolidin-1-yl)imidazo[1,2-b]pyridazin-3-yl)benzonitrile, that is, an imidazo[1,2b]pyridazine compound bearing an aryl-substituted heterocyclic group at the 6-position and a benzonitrile group at the 3 position. This compound does not fall within the general formulae disclosed therein representing 3-aryl substiuted-imidazo[1,2-b]pyridazines. This compound is purported to be suitable for treating diseases mediated by the PI3K receptor, the JAK-2 receptor and the Trk receptor.

International Publication No. WO 2007/013673 discloses 1-phenyl-3-(6-(1-phenylethylamino)imidazo[1,2-b]pyridazin-3-yl)urea and N-(6-(4-hydroxycyclohexylamino)imidazo[1,2-b]pyridazin-3-yl)benzamide, that is, imidazo[1,2b]pyridazine compounds bearing an amino group at the 6-position and an amide or urea moiety at the 3 position. These compounds are said to be Lck inhibitors.

There is a continuing need for new and more effective treatments for the relief of pain, especially chronic pain. Because TrkA and other Trk kinases may serve as a mediator of NGF driven biological responses, inhibitors of TrkA and other Trk kinases may provide an effective treatment for chronic pain states.

It has now been found that certain imidazo[1,2b]pyridazine compounds bearing an aryl or heteroaryl-substituted heterocyclic group at the 6-position and a group having the formula $NR^1C(=O)R^2$ at the 3-position, wherein $R^1$ and $R^2$ are as defined herein, are inhibitors of Trk kinases, in particular inhibitors of TrkA and/or TrkB, which are useful for treating disorders and diseases which can be treated by inhibiting Trk-A and/or TrkB kinases, such as pain, including chronic and acute pain, or cancer. Certain compounds of the invention which are inhibitors of TrkA and/or TrkB may be useful in the treatment of multiple types of pain (including acute and chronic pain) including inflammatory pain, neuropathic pain, and pain associated with cancer, surgery and bone fracture. In addition, compounds of the invention may be useful for treating cancer, inflammation, neurodegenerative diseases and certain infectious diseases.

Accordingly, one embodiment of this invention provides a compound of the general Formula 1:

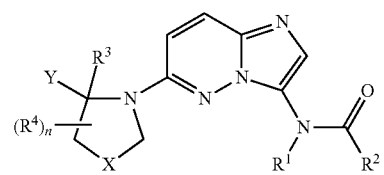

or a pharmaceutically acceptable salt thereof, wherein:

$R^1$ is H or (1-6C alkyl);

$R^2$ is $NR^bR^c$, (1-4 C)alkyl, (1-4 C)fluoro alkyl, $CF_3$, (1-4 C)hydroxyalkyl, -(1-4C alkyl)hetAr$^1$, -(1-4C alkyl)NH(1-4C alkyl), hetAr$^2$, hetCyc$^1$, hetCyc$^2$, phenyl which is optionally substituted with $NHSO_2$(1-4C alkyl), or (3-6C)cycloalkyl which is optionally substituted with (1-4C alkyl), CN, OH, $CF_3$, $CO_2$(1-4C alkyl) or $CO_2H$;

$R^b$ is H or (1-6C alkyl);

$R^c$ is H, (1-4C)alkyl, (1-4C)hydroxyalkyl, hetAr$^3$, or phenyl, wherein said phenyl is optionally substituted with one or more substituents independently selected from halogen, CN, $CF_3$ and —O(1-4C alkyl), or $NR^bR^c$ forms a 4 membered heterocyclic ring having a ring nitrogen atom wherein said heterocyclic ring is optionally substituted with one or more substituents independently selected from halogen, OH, (1-4C alkyl), (1-4 C)alkoxy, —OC(=O)(1-4C alkyl), $NH_2$, —NHC(=O)O(1-4C alkyl), and (1-4C)hydroxyalkyl, or $NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, $NHC(=O)O$(1-4C alkyl) and oxo, or $NR^bR^c$ forms a 7-8 membered bridged heterocyclic ring having 1-2 ring nitrogen atoms and optionally substituted with $CO_2$(1-4C alkyl);

hetAr$^1$ is a 5-membered heteroaryl ring having 1-3 ring nitrogen atoms;

hetAr$^2$ is 5-6 membered heteroaryl ring having at least one nitrogen ring atom and optionally having a second ring heteroatom independently selected from N and S, wherein said heteroaryl ring is optionally substituted with one or more substituents independently selected from (1-4C alkyl), halogen, -(1-4 C)alkoxy, and NH(1-4C alkyl);

hetCyc$^1$ is a carbon-linked 4-6 membered azacyclic ring optionally substituted with one or more substituents independently selected from (1-4C alkyl), $CO_2H$ and $CO_2$(1-4C alkyl);

hetCyc$^2$ is a pyridinone or pyridazinone ring substituted with a substituent selected from (1-4C)alkyl;

hetAr$^3$ is a 5-6 membered heteroaryl ring having 1-2 ring heteroatoms independently selected from N and O and optionally substituted with one or more substituents independently selected from (1-4C)alkyl;

Y is a phenyl ring optionally substituted with one or more substituents independently selected from halogen, (1-4C) alkoxy, $CF_3$ and $CHF_2$, or a 5-6 membered heteroaryl ring having a ring heteroatom selected from N and S;

X is null, —CH$_2$—, CH$_2$CH$_2$—, —CH$_2$O—, or —CH$_2$NR$^d$—;

R$^d$ is H or (1-4C alkyl);

R$^3$ is H or (1-4C alkyl);

each R$^4$ is independently selected from halogen, (1-4C) alkyl, OH, (1-4 C)alkoxy, NH$_2$, NH(1-4C alkyl) and CH$_2$OH; and n is 0, 1, 2, 3, 4, 5 or 6.

In certain embodiments of Formula I, R$^1$ is hydrogen.

In certain embodiments of Formula I, R$^1$ is (1-6C)alkyl. A particular example is methyl.

In certain embodiments of Formula I, R$^2$ is a group having the formula NR$^b$R$^c$, such that the group at the 3 position of the imidazo[1,2b]pyridazine core of Formula I has the formula NR$^1$C(=O)NR$^b$R$^c$.

In certain embodiments, R$^b$ is H. In certain embodiments, R$^b$ is (1-6C alkyl), for example Me. In certain embodiments, R$^c$ is H, (1-4C)alkyl, (1-4C)hydroxyalkyl, hetAr$^3$, or phenyl, wherein said phenyl is optionally substituted with one or more substituents independently selected from halogen, CN, CF$_3$ and —O(1-4C alkyl).

In certain embodiments, R$^2$ is NR$^b$R$^c$, where R$^c$ is hydrogen. In particular embodiments, the group represented by NR$^b$R$^c$ is NH$_2$.

In certain embodiments, R$^2$ is NR$^b$R$^c$, where R$^c$ is (1-4C) alkyl. Examples include methyl, ethyl, propyl, isopropyl, butyl, isobutyl, and the like. In particular embodiments, the group represented by NR$^b$R$^c$ includes NHMe, NMe$_2$ and NH(t-butyl).

In certain embodiments, R$^2$ is NR$^b$R$^c$, where R$^c$ is (1-4C) hydroxyalkyl. Examples include CH$_2$CH$_2$OH and CH$_2$CH$_2$CH$_2$OH. In particular embodiments, the group represented by NR$^b$R$^c$ includes NMe(CH$_2$CH$_2$OH).

In certain embodiments, R$^2$ is NR$^b$R$^c$, where R$^c$ is hetAr$^3$, and hetAr$^3$ is an optionally substituted 5-6 membered heteroaryl ring having 1-2 ring heteroatoms independently selected from N and O. An example of hetAr$^3$ includes an isoxazolyl ring. In certain embodiments, hetAr$^3$ is unsubstituted. In other embodiments, hetAr$^3$ is substituted with one or more substituents independently selected from (1-4C) alkyl, for example one or more substituents independently selected from methyl and ethyl. Examples of hetAr$^3$ include dimethylisoxazolyl. In particular embodiments, the group represented by NR$^b$R$^c$ includes the group having the structure:

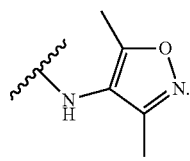 [SMILES: *Nc1c(C)noc1C]

In certain embodiments, R$^2$ is NR$^b$R$^c$, where R$^c$ is a phenyl group optionally substituted with one or more substituents independently selected from halogen, CN, CF$_3$ and O-(1-4C alkyl). Examples of R$^c$ include phenyl, fluorophenyl, chlorophenyl, cyanophenyl, methoxyphenyl, trifluoromethylphenyl, dichlorophenyl, and trimethoxyphenyl. More particular examples include 4-fluorophenyl, 3-chlorophenyl, 4-chlorophenyl, 3-cyanophenyl, 4-cyanophenyl, 4-methoxyphenyl, 2-4-dichlorophenyl, 3-(trifluoromethyl) phenyl, 3,5-dichlorophenyl, and 3,4,5-trimethoxyphenyl. In particular embodiments, the group represented by NR$^b$R$^c$ includes groups having the structures:

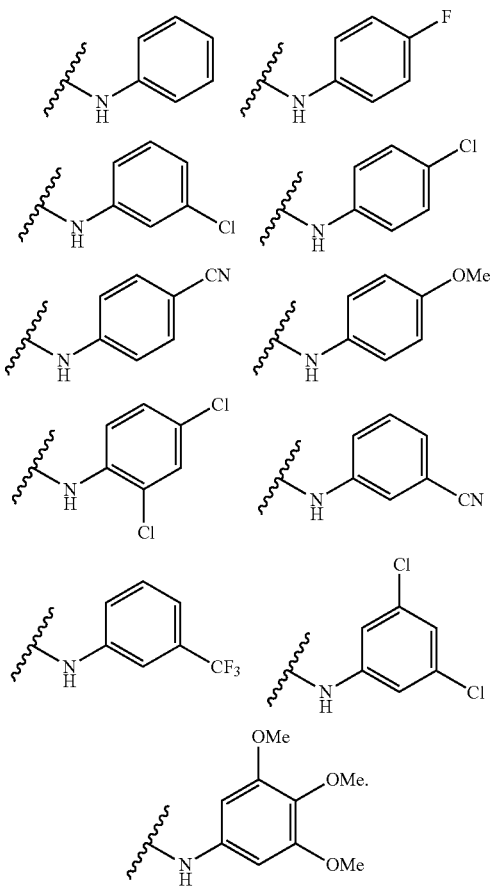

In certain embodiments, R$^2$ is —NR$^b$R$^c$, wherein:

(i) NR$^b$R$^c$ forms a 4 membered heterocyclic ring having a ring nitrogen atom optionally substituted with one or more substituents independently selected from halogen, OH, (1-4C alkyl), (1-4 C)alkoxy, —OC(=O)(1-4C alkyl), NH$_2$, —NHC(=O)O(1-4C alkyl), and (1-4C)hydroxyalkyl, or (ii) NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(=O)O(1-4C alkyl) and oxo, or (iii) NR$^b$R$^c$ forms a 7-8 membered bridged heterocyclic ring having 1-2 ring nitrogen atoms and optionally substituted with CO$_2$(1-4C alkyl).

In certain embodiments, R$^2$ is —NR$^b$R$^c$, wherein —NR$^b$R$^c$ forms a 4 membered heterocyclic ring having a ring nitrogen atom and which is optionally substituted with one or more substituents independently selected from F, OH, (1-4C alkyl), —O(1-4C alkyl), —OC(=O)(1-4C alkyl), NH$_2$, —NHC(=O)O(1-4C alkyl), and (1-4C)hydroxyalkyl. Examples include azetidinyl rings optionally substituted with one or more groups independently selected from OH, methyl, OMe, OC(=O)C(CH$_3$)$_2$, NH$_2$, —NHC(=O)OC (CH$_3$)$_3$ and CH$_2$OH. Particular examples of R$^2$ when represented by —NR$^b$R$^c$, wherein —NR$^b$R$^c$ forms a 4 membered heterocyclic ring, include the structures:

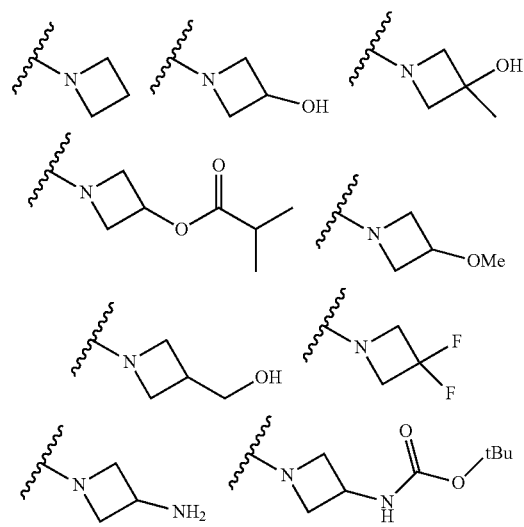

In certain embodiments, $R^2$ is $-NR^bR^c$, wherein $-NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, $NHC(=O)O$(1-4C alkyl) and oxo. Examples include optionally substituted pyrrolidinyl, piperidinyl, piperazinyl, morpholinyl and piperidinesulfone rings. Examples of substituents on the 5-6 membered heterocyclic ring include OH, F, $NH_2$, $CO_2H$, $CO_2Et$, $NHCO_2C(CH_3)_3$, $CF_3$, methyl, ethyl, isopropyl, $CO_2C(CH_2)_3$ and oxo. In one embodiment, the heterocyclic ring is optionally substituted with one or two of said substituents. Particular examples of $R^2$ when represented by $-NR^bR^c$, wherein $-NR^bR^c$ forms a 5-6 membered heterocyclic ring, include the structures:

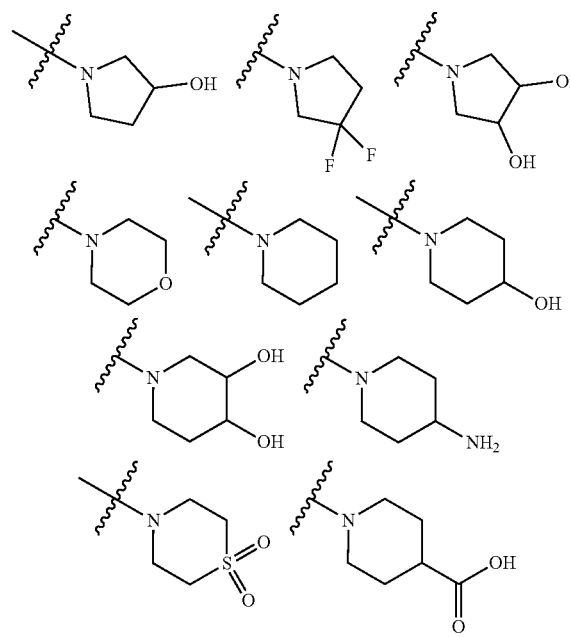

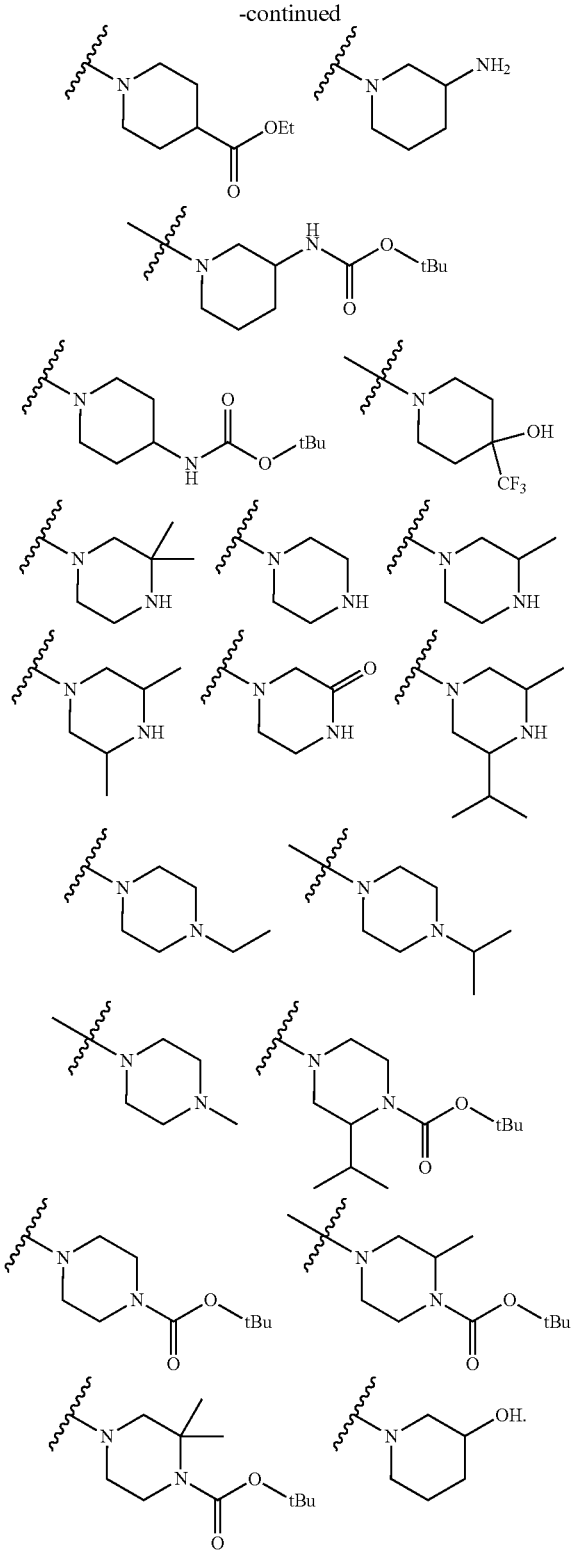

In certain embodiments, $R^2$ is $-NR^bR^c$, wherein $NR^bR^c$ forms a 7-8 membered bridged heterocyclic ring having 1-2 ring nitrogen atoms and optionally substituted with $CO_2$(1-4C alkyl). Examples of bridged heterocyclic rings include diazabicyclooctane rings such as 3,8-diazabicyclo[3.2.1]octane rings, which are optionally substituted with $CO_2$(1-4C alkyl), such as $CO_2C(CH_3)_3$. Particular examples of $R^2$ when represented by —NR$^b$R$^c$, wherein —NR$^b$R$^c$ forms a 7-8 membered bridged heterocyclic ring, include the structures:

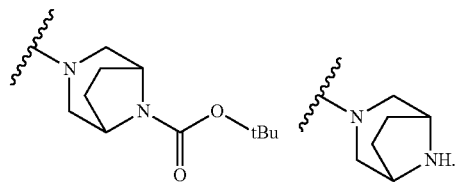 [SMILES: *N1CC2CCC(C1)N2C(=O)OC(C)(C)C ; *N1CC2CCC(C1)N2]

In certain embodiments, R$^2$ is selected from (1-4C)alkyl, (1-4C)fluoroalkyl, CF$_3$, -(1-4C alkyl)hetAr$^1$, and -(1-4C alkyl)NH(1-4C alkyl). In certain embodiments, R$^2$ is selected from (1-4C)alkyl, (1-4C)fluoroalkyl, CF$_3$, -(1-4C) hydroxyalkyl, (1-4C alkyl)hetAr$^1$, and -(1-4C alkyl)NH(1-4C alkyl).

In certain embodiments, R$^2$ is (1-4C)alkyl. Particular examples include methyl, isopropyl and tert-butyl.

In certain embodiments, R$^2$ is (1-4C)fluoroalkyl. A particular example includes CF(CH$_3$)$_2$.

In certain embodiments, R$^2$ is CF$_3$.

In certain embodiments, R$^2$ is (1-4C)hydroxyalkyl. Particular examples include C(CH$_3$)$_2$OH and C(CH$_3$)$_2$CH$_2$OH.

In certain embodiments, R$^2$ is (3-6C cycloalkyl) which is optionally substituted with (1-4C)alkyl, CN, OH, CF$_3$, CO$_2$(1-4C alkyl) or CO$_2$H. In certain embodiments, R$^2$ is an optionally substituted cyclopropyl ring. Particular examples of R$^2$ include the structures:

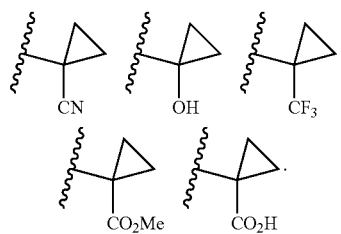

In certain embodiments, R$^2$ is -(1-4C alkyl)hetAr$^1$, where hetAr$^1$ is a 5-membered heteroaryl ring having 1-3 ring nitrogen atoms. An example of hetAr$^1$ is a triazolyl ring, such as 1,2,4-triazolyl. Examples of the (1-4C)alkyl portion include methylene, ethylene, dimethylmethylene, and the like. A particular value for R$^2$ when represented by -(1-4C alkyl)hetAr$^1$ is the structure:

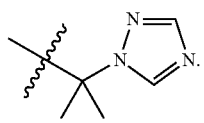 [SMILES: *C(C)(C)n1cncn1]

In certain embodiments, R$^2$ is -(1-4C alkyl)NH(1-4C alkyl). Examples include groups having the formula (1-4C alkyl)NHCH$_3$. A particular value include C(CH$_3$)$_2$NHCH$_3$.

In certain embodiments, R$^2$ is selected from hetAr$^2$, hetCyc$^1$, hetCyc$^2$ and hetAr$^3$. In certain embodiments, R$^2$ is selected from hetAr$^2$, hetCyc$^1$, and hetCyc$^2$.

In certain embodiments, R$^2$ is hetAr$^2$. Examples of hetAr$^2$ include pyridyl, pyrimidyl, pyrazinyl, pyrazolyl, imidazolyl and thiazolyl rings optionally substituted with one or more substituents independently selected from (1-4C alkyl), halogen, —O(1-4C alkyl), and NH(1-4C alkyl). Examples of substituents for hetAr$^2$ include methyl, ethyl, chloro, OMe, and NHCH(CH$_3$)$_2$. Particular values of R$^2$ include the structures:

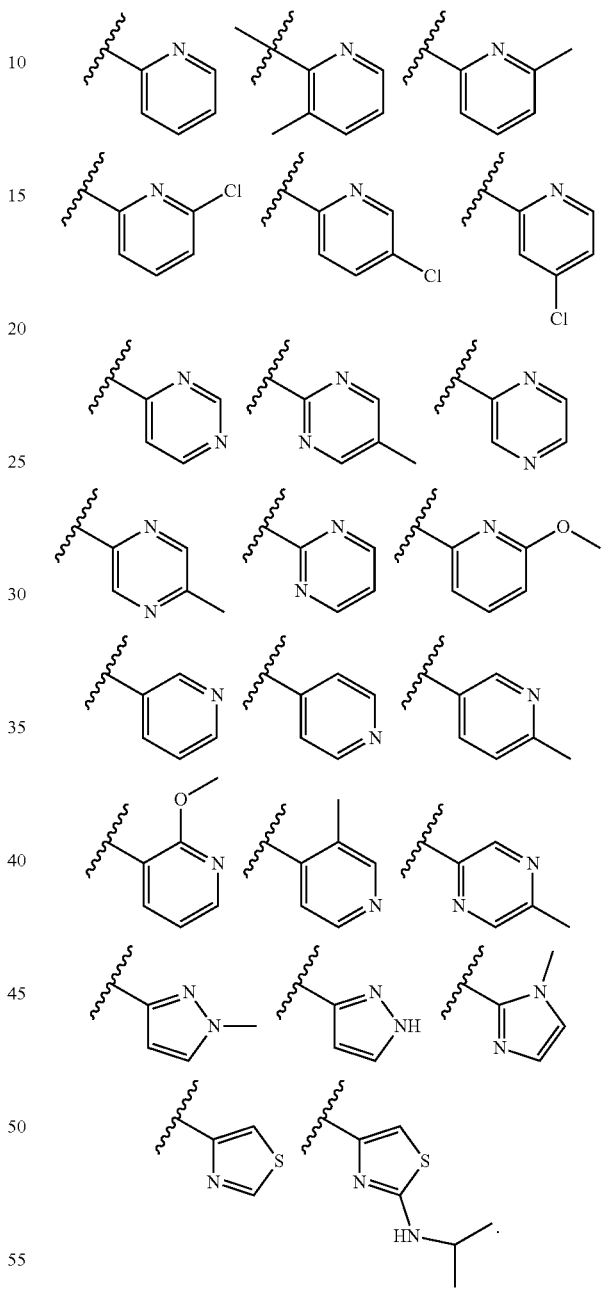

In certain embodiments, R$^2$ is hetCyc$^1$. Examples of hetCyc$^1$ include carbon-linked azetidinyl, pyrrolidinyl and piperidinyl rings optionally substituted with one or more substituents independently selected from (1-4C alkyl), CO$_2$H and CO$_2$(1-4C alkyl). Examples of substituents include methyl, ethyl, propyl, CO$_2$H, CO$_2$Me, CO$_2$Et, and CO$_2$C(CH$_3$)$_3$. In one embodiment, hetCyc$^1$ is optionally substituted with one or two of said substituents. Particular values for R$^2$ represented by hetCyc$^1$ include the structures:

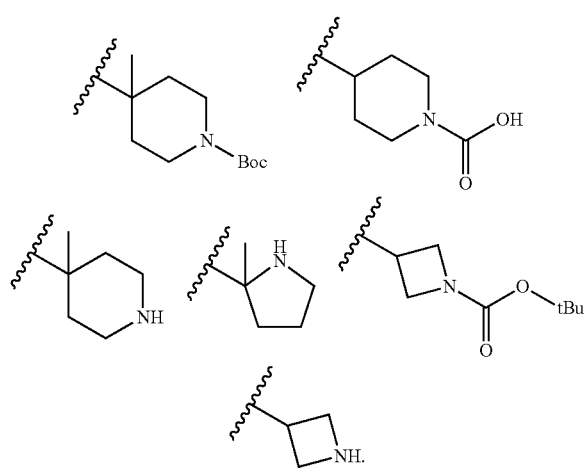

In certain embodiments, R² is hetCyc². Examples include pyridinone or pyridazinone ring substituted with a substituent selected from (1-4C)alkyl such as a methyl or ethyl group. Particular values of R² when represented by hetCyc² include the structures:

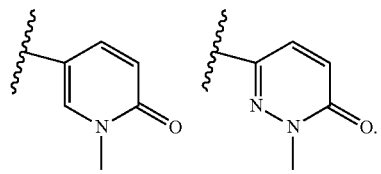

In certain embodiments, R² is phenyl which is optionally substituted with an NHSO₂(1-4C alkyl) group such a methanesulfonamido or an ethanesulfonamido group. Particular values for R² include the structures:

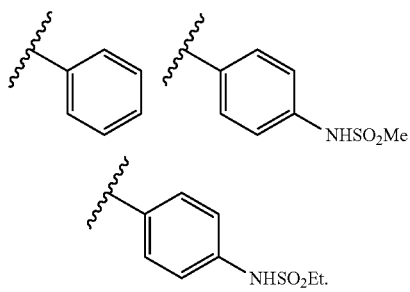

Referring now to the substituents on the ring at the 6-position of Formula I, in one embodiment Y is phenyl optionally substituted with one or more substituents independently selected from halogen, (1-4C)alkoxy, CF₃ and CHF₂. In one embodiment, Y is phenyl optionally substituted with one or more substituents independently selected from F, Cl, OMe, CF₃ and CHF₂. In certain embodiments, Y is phenyl optionally substituted with one or two of said substituents. Particular values for Y include phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl and 3-chloro-5-fluorophenyl.

In one embodiment, Y is a 5-6 membered heteroaryl ring having a ring heteroatom selected from N and S. Examples include pyridyl and thienyl groups. Particular values for Y include 2-pyridyl, 3-pyridyl and 2-thienyl.

In one embodiment, the Y group has the absolute configuration shown in Figure Ia:

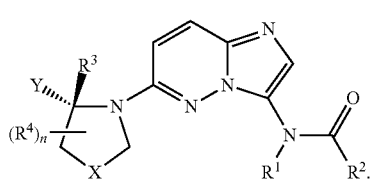

Ia

With reference to the R³ substituent, in one embodiment R³ is H. In one embodiment, R³ is (1-4C)alkyl, for example, methyl, ethyl, propyl, isopropyl, or butyl. Particular values for R³ include hydrogen and methyl.

With reference to the R⁴ substituent, in one embodiment R⁴ is halogen. Particular examples are fluoro and chloro.

In one embodiment, R⁴ is (1-4C)alkyl, such as methyl, ethyl, propyl, isopropyl, or butyl. A particular example is methyl.

In one embodiment, R⁴ is OH.

In one embodiment, R⁴ is (1-4 C)alkoxy, for example OMe and OEt.

In one embodiment, R⁴ is NH₂.

In one embodiment, R⁴ is NH(1-4C alkyl), for example NHMe, NHEt, NHPr, NHiPr and NHBu. A particular example is NHMe.

In one embodiment, R⁴ is CH₂OH.

In one embodiment, each R⁴ is independently selected from F, Cl, OH, OMe, NH₂, Me, CH₂OH, and NHMe.

In one embodiment, n is 0, 1, 2, 3 or 4. In one embodiment, n is 0, 1, 2 or 3. In one embodiment, n is 0, 1 or 2.

With continued reference to the ring at the 6-position of Formula I, in certain embodiments, X is null, —CH₂— or CH₂CH₂—.

In one embodiment X is null, such that the heterocyclic ring at the 6-position of Formula I has the structure:

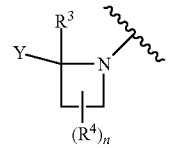

where R³, R⁴, Y and n are as defined herein. In one embodiment, Y is phenyl optionally substituted with one or two F. In one embodiment, Y is a 5-6 membered heteroaryl ring. In one embodiment, R³ is hydrogen. In another embodiment, R³ is methyl. A particular example of the ring at the 6-position of Formula I when X is null includes the structures:

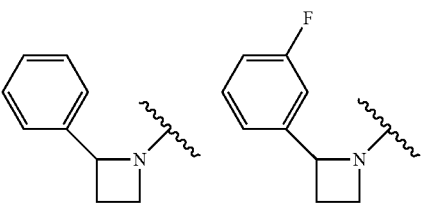

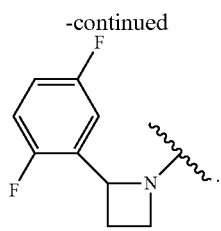

In one embodiment, X is CH$_2$, such that the heterocyclic ring at the 6-position of Formula I has the structure:

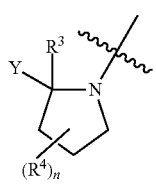

where R$^3$, R$^4$, Y and n are as defined herein. In one embodiment Y is phenyl substituted with one or two fluoro atoms. In one embodiment, R$^3$ is hydrogen. In another embodiment, R$^3$ is methyl. In one embodiment, each R$^4$ is independently selected from F, Cl, Me, OH, OMe, NH$_2$, NHMe, CH$_2$OH, CHF$_2$ and CF$_3$. In one embodiment, n is 0, 1 or 2. Particular examples of the ring at the 6-position of Formula I when X is CH$_2$ include the structures:

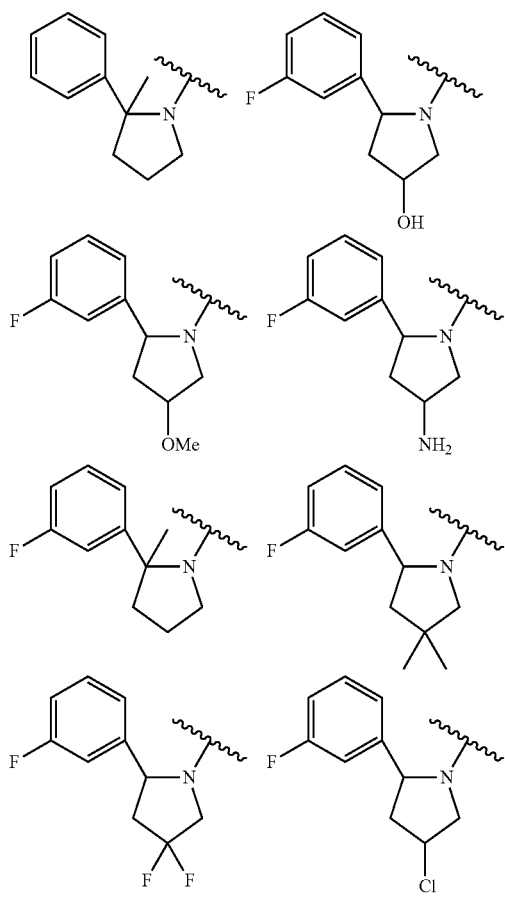

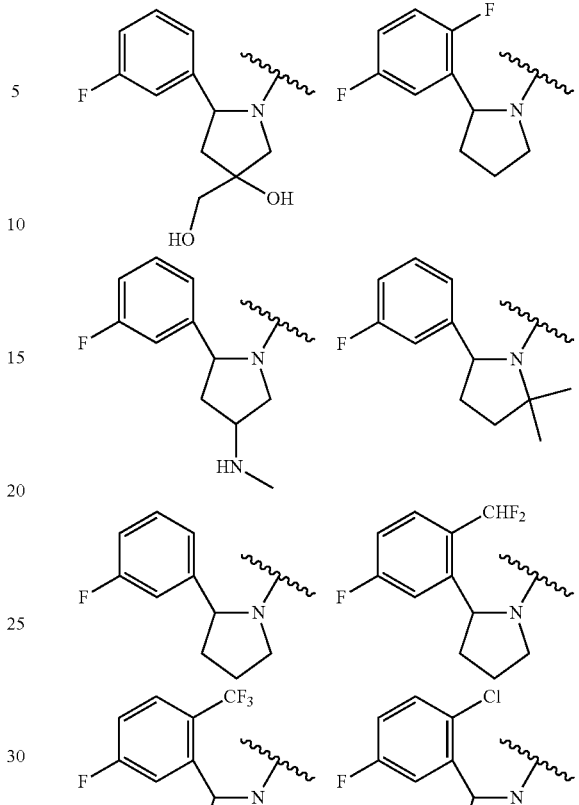

In one embodiment, X is CH$_2$, such that the heterocyclic ring at the 6-position of Formula I has the structure:

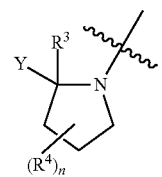

where R$^3$, R$^4$, Y and n are as defined herein. In one embodiment, Y is a 5-6 membered heteroaryl ring having a ring heteroatom selected from N and S. Examples of 5-6 membered heteroaryl rings include pyridyl and thienyl. In one embodiment, R$^3$ is hydrogen. In another embodiment, R$^3$ is methyl. In one embodiment, each R$^4$ is independently selected from F, Cl, Me, OH, OMe, NH$_2$, NHMe and CH$_2$OH. In one embodiment, n is 0, 1 or 2. In one embodiment, n is 0. Particular examples of the ring at the 6-position of Formula I when X is CH$_2$ include the structures:

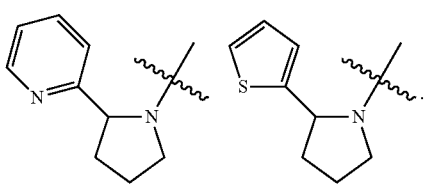 [SMILES: *N1CCCC1c1ccccn1 ; *N1CCCC1c1cccs1]

In one embodiment, X is CH$_2$CH$_2$, such that the heterocyclic ring at the 6-position of Formula I has the structure:

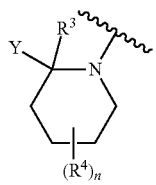

where R$^3$, R$^4$, Y and n are as defined herein. In one embodiment, Y is phenyl optionally substituted with one or two fluoro atoms. In one embodiment, Y is a pyridyl ring. In one embodiment, R$^3$ is hydrogen. In another embodiment, R$^3$ is methyl. In one embodiment, n is 0, 1 or 2. In one embodiment, n is 0. Particular examples of the ring at the 6-position of Formula I when X is CH$_2$CH$_2$ include the structures:

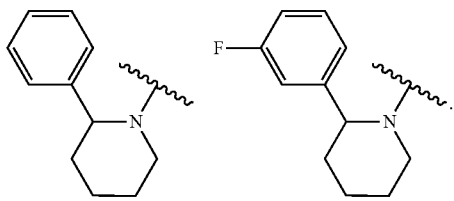 [SMILES: *N1CCCCC1c1ccccc1 ; *N1CCCCC1c1cccc(F)c1]

In one embodiment, X is —CH$_2$O—, such that the heterocyclic ring at the 6-position of Formula I has the structure:

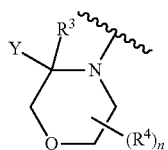

where R$^3$, R$^4$, Y and n are as defined herein. In one embodiment, Y is phenyl optionally substituted with one or more substituents independently selected from F and (1-4C) alkoxy, for example one or two substituents independently selected from F and OMe. In one embodiment, Y is fluorophenyl, difluorophenyl or methoxyphenyl. In one embodiment, Y is pyridyl. In one embodiment, R$^3$ is hydrogen. In another embodiment, R$^3$ is methyl. In one embodiment, n is 0, 1 or 2. Particular examples of the ring at the 6-position of Formula I when X is —CH$_2$O— include the structures:

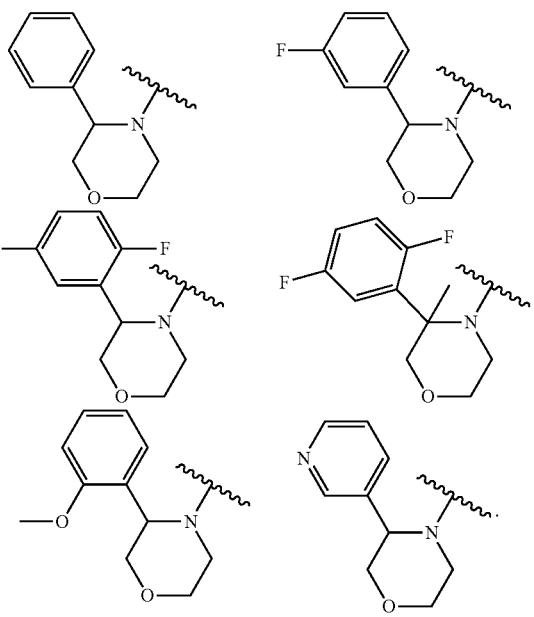

In one embodiment, X is —CH$_2$NR$^d$—, such that the heterocyclic ring at the 6-position of Formula I has the structure:

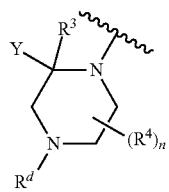

where R$^3$, R$^4$, Y, R$^d$ and n are as defined herein. In one embodiment, R$^d$ is H. In one embodiment, R$^d$ is (1-4C alkyl), for example methyl, ethyl, propyl, isopropyl, or butyl. A particular example is methyl. In one embodiment, Y is phenyl optionally substituted with one or two F. In one embodiment, n is 0. Particular examples of the ring at the 6-position of Formula I when X is —CH$_2$NR$^d$— include the structures:

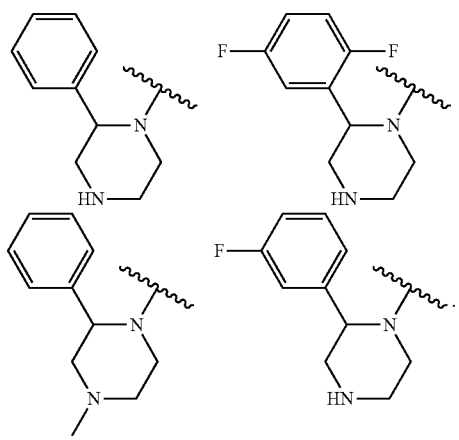

Compounds of Formula I include compound of Formula Ib, wherein:

$R^1$ is H or (1-6C alkyl);

$R^2$ is $NR^bR^c$;

$NR^bR^c$ forms a 4 membered heterocyclic ring having a ring nitrogen atom, wherein said heterocyclic ring is optionally substituted with one or more substituents independently selected from halogen, OH, (1-4C alkyl), (1-4 C)alkoxy, —OC(=O)(1-4C alkyl), $NH_2$, —NHC(=O)O(1-4C alkyl) and (1-4 C)hydroxyalkyl, or $NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, NHC(=O)O(1-4C alkyl) and oxo;

Y is phenyl optionally substituted with one or more substituents independently selected from halogen, (1-4C) alkoxy, $CF_3$ and $CHF_2$;

X is null, —$CH_2$—, or $CH_2CH_2$—;

$R^3$ is H or (1-4C alkyl);

each $R^4$ is independently selected from halogen, (1-4C) alkyl, OH, (1-4 C)alkoxy, $NH_2$, NH(1-4C alkyl) and $CH_2OH$; and n is 0, 1, or 2.

In one embodiment of Formula Ib, Y is phenyl optionally substituted with one or more halogen atoms. In one embodiment of Formula Ib, Y is phenyl optionally substituted with one or two fluorine atoms.

In one embodiment of Formula Ib, (i) $NR^bR^c$ forms a 4 membered heterocyclic ring having a ring nitrogen atom, wherein said ring is optionally substituted with one or more substituents independently selected from halogen, OH, (1-4C alkyl), (1-4 C)alkoxy, —OC(=O)(1-4C alkyl), $NH_2$, —NHC(=O)O(1-4C alkyl) and (1-4C)hydroxyalkyl, or (ii) $NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, NHC(=O)O(1-4C alkyl) and oxo.

In one embodiment of Formula Ib, n is zero or one.

In one embodiment of Formula Ib, $R^3$ is hydrogen.

Compounds of Formula Ib include compounds of Formula Ic wherein:

$R^1$ is H or (1-6C alkyl);

$R^2$ is $NR^bR^c$;

$NR^bR^c$ forms a 4 membered heterocyclic ring having a ring nitrogen atom, wherein said heterocyclic ring is optionally substituted with one or more substituents independently selected from halogen, OH, (1-4C alkyl), (1-4 C)alkoxy, —OC(=O)(1-4C alkyl), $NH_2$, —NHC(=O)O(1-4C alkyl) and (1-4C)hydroxyalkyl;

Y is phenyl optionally substituted with one or more substituents independently selected from halogen, (1-4C) alkoxy, $CF_3$ and $CHF_2$;

X is —$CH_2$—;

$R^3$ is H or (1-4C alkyl);

each $R^4$ is independently selected from halogen, (1-4C) alkyl, OH, (1-4 C)alkoxy, $NH_2$, NH(1-4C alkyl) and $CH_2OH$; and n is 0, 1, or 2.

In one embodiment of Formula Ic, the heterocyclic ring formed by $NR^bR^c$ is optionally substituted with one or two substituents independently selected from F, OH, methyl, OMe, OC(=O)C(CH_3)_2, $NH_2$, —NHC(=O)OC(CH_3)_3 and $CH_2OH$.

In one embodiment of Formula Ic, Y is phenyl optionally substituted with one or more halogen atoms. In one embodiment of Formula Ic, Y is phenyl optionally substituted with one or two fluorine atoms.

Compounds of Formula Ib also include compounds of Formula Id wherein:

$R^1$ is H or (1-6C alkyl);

$R^2$ is $NR^bR^c$;

$NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, NHC(=O)O(1-4C alkyl) and oxo;

Y is phenyl optionally substituted with one or more substituents independently selected from halogen, (1-4C) alkoxy, $CF_3$ and $CHF_2$;

X is —$CH_2$—;

$R^3$ is H or (1-4C alkyl);

each $R^4$ is independently selected from halogen, (1-4C) alkyl, OH, (1-4 C)alkoxy, $NH_2$, NH(1-4C alkyl) and $CH_2OH$; and n is 0, 1, or 2.

In one embodiment of Formula Id, the heterocyclic ring formed by $NR^bR^c$ is optionally substituted with one or two substituents independently selected from OH, F, $NH_2$, $CO_2H$, $CO_2Et$, $NHCO_2C(CH_3)_3$, $CF_3$, methyl, ethyl, isopropyl, $CO_2C(CH_3)_3$ and oxo.

In one embodiment of Formula Id, the heterocyclic ring formed by $NR^bR^c$ is a 5-6 membered azacyclic ring.

In one embodiment of Formula Id, Y is phenyl optionally substituted with one or more halogen atoms. In one embodiment of Formula Id, Y is phenyl optionally substituted with one or two fluorine atoms.

In one embodiment of Formula Ic or Id, n is zero or one.

In one embodiment of Formula Ic or Id, $R^3$ is hydrogen.

In one embodiment of Formula Ic or Id, $R^1$ is hydrogen.

It will be appreciated that certain compounds according to the invention may contain one or more centers of asymmetry and may therefore be prepared and isolated in a mixture of isomers such as a racemic mixture, or in an enantiomerically pure form. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will also be appreciated that certain compounds of Formula I may be used as intermediates for further compounds of Formula I.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Particular examples include hydrochloride and trifluoroacetate salts of compounds of Formula I.

It will further be appreciated that the compounds of Formula I or their salts may be isolated in the form of solvates, and accordingly that any such solvate is included within the scope of the present invention.

The term "(1-4C) alkyl" as used herein refers to saturated linear or branched-chain monovalent hydrocarbon radicals of one to four carbon atoms, respectively. Examples include, but are not limited to, methyl, ethyl, 1-propyl, 2-propyl, 1-butyl, 2-methyl-1-propyl, 2-butyl, and 2-methyl-2-propyl.

The term "(1-4C) alkoxy" as used herein refers to saturated linear or branched-chain monovalent radicals of one to four carbon atoms, respectively, wherein the radical is on the oxygen atom.

The term "(1-4C)hydroxyalkyl" as used herein refers to saturated linear or branched-chain monovalent hydrocarbon radicals of one to four carbon atoms, respectively, wherein one of the hydrogen atoms is replaced with an OH group.

The term "halogen" includes fluoro, chloro, bromo and iodo.

According to another aspect, the present invention provides a process for the preparation of a compound of Formula I or a pharmaceutically acceptable salt thereof as defined herein which comprises:

(a) for a compound of Formula I wherein $R^2$ is $NR^bR^c$, reacting a corresponding compound of formula II

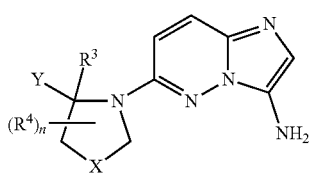

with a compound having the formula $HNR^bR^c$ in the presence of a coupling reagent; or (b) for a compound of Formula I wherein $R^2$ is $NR^bR^c$ and $R^b$ is H, reacting a corresponding compound of formula II with a compound having the formula $O=C=N-R^c$; or (c) for a compound of Formula I wherein $R^2$ is $hetAr^2$ or a phenyl ring which is optionally substituted with $NHSO_2$(1-4C alkyl), reacting a corresponding compound of Formula II with a corresponding compound having the formula $HOC(=O)R^2$ in the presence of a coupling reagent and a base; or (d) for a compound of Formula I wherein $R^2$ is (1-4C) alkyl, (1-4C)fluoroalkyl, $CF_3$, (1-4C)hydroxyalkyl, or (3-6C)cycloalkyl which is optionally substituted with (1-4C alkyl), CN, OH, $CF_3$, $CO_2$(1-4C alkyl) or $CO_2H$, reacting a corresponding compound of Formula II with a corresponding compound having the formula $(R^2CO)_2O$ in the presence of a base; and (e) removing or adding any protecting groups if desired, and forming a salt if desired.

Referring to method (a), examples of coupling reagents include any known coupling reagent, for examples peptide coupling reagents such as CDI (carbonyl diimidazole), DCC (N,N'-dicyclohexylcarbodiimide), and EDCI (1-(3-dimethylaminopropyl)-3-ethylcarboiimide). The reaction is optionally performed in the presence of an amine base, such as DIEA (diisopropylethylamine). Suitable solvents include dichloromethane, dichloroethane, THF, and DMF. The reaction is conveniently performed at ambient temperature.

Compounds of formula II

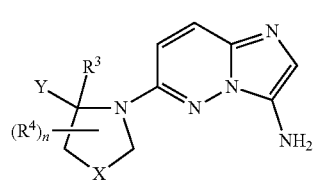

can be prepared by reducing a corresponding compound of formula III

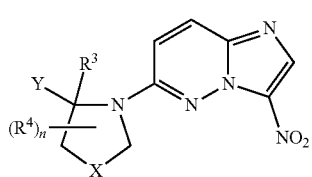

under standard reducing conditions, for example reacting a compound of formula II with zinc dust under acidic conditions, such as in the presence of an acid such as $NH_4Cl$.

Compounds of Formula III can be prepared by coupling a corresponding compound having the formula IV

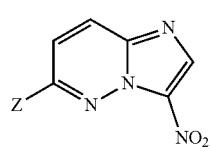

where Z is a leaving atom or group such as a halogen (for example Cl), with a corresponding compound having the formula V

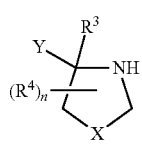

where $R^3$, $R^4$, n, X and Y are as defined herein, in a suitable solvent such as an alcohol (for example n-butanol or isopropanol), at elevated temperatures, for example at temperatures between 100 and 180° C., for example at a temperature of about 140° C.

Compounds of the formula IV can be prepared from a corresponding compound of Formula V

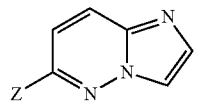

using standard nitrating conditions known in the art, for example by reacting a corresponding compound of Formula V with nitric acid in the presence of an activating agent such as TFA or concentrated sulfuric acid. Compounds of Formula V are commercially available or can be prepared by standard methods known in the art.

Compounds of Formula II and III are also believed to be novel and provide a further embodiment of this invention.

Referring to method (b), suitable solvents include dichloromethane, dichloroethane, THF, and DMF. The reaction is conveniently performed at ambient temperature.

Referring to method (c), suitable coupling reagents include HATU, HBTU and other coupling reagents well known to persons skilled in the art. Suitable bases include amine bases such as diisopropylethylamine (DIEA) and triethylamine. Suitable solvents include DMF and CH$_3$CN. The reaction is conveniently performed at temperatures between 0° C. and ambient temperature.

Referring to method (d), suitable bases include amine bases such as pyridine or triethylamine. Suitable solvents include dichloromethane and dichloroethane. The reaction is conveniently performed at temperatures between 0° C. and ambient temperature.

Referring to method (e), suitable bases include amine bases (for example DIEA or triethylamine) and alkali metal carbonate bases (for example, potassium carbonate or sodium carbonate). In certain embodiments, compounds of formula II are treated with an amine base, and subsequently the chloroformate compound is added followed by the addition of the alkali metal carbonate base. Suitable solvents include DCM, DCE and THF. The reaction is conveniently performed at ambient temperature.

The ability of compounds to act as Trk-A inhibitors may be demonstrated by the assays described in Examples A and B. The ability of compounds to act as Trk-A inhibitors may be demonstrated by the assay described in Example B.

Compounds of Formula I are useful for treating chronic and acute pain, including pain associated with cancer. Certain compounds which are inhibitors of TrkA and/or TrkB may be useful in the treatment of multiple types of pain including inflammatory pain, neuropathic pain, and pain associated with cancer, surgery, and bone fracture.

Compounds of Formula I are also useful for treating cancers including neuroblastoma, ovarian, pancreatic and colorectal cancer.

Compounds of Formula I are also useful for treating inflammation and certain infectious diseases.

In addition, compounds of Formula I may also be used to treat interstitial cystitis (IC), painful bladder syndrome (PBS), urinary incontinence, asthma, anorexia, atopic dermatitis, and psoriasis.

Compounds of Formula I may also be used to treat demyelination and dysmyelination by promoting myelination, neuronal survival, and oligodendrocyte differentiation via blocking Sp35-TrkA interaction.

Compounds of Formula I may be of therapeutic value for the useful in the treatment of bone-related diseases (such as those involving bone resorption). Examples of bone-related diseases include metastatic bone disease, treatment-induced bone loss, osteoporosis, rheumatoid arthritis, ankylosing spondylitis, Paget's disease, and periodontal disease. The osteoporosis may be attributed to (1) menopause in women, (2) aging in men or women, (3) suboptimal bone growth during childhood and adolescence that resulted in failure to reach peak bone mass, and/or (4) bone loss secondary to other disease conditions, eating disorders, medications and/or medical treatments.

Other osteolytic diseases that can be treated according to the present invention are more localized. A particular example is metastatic tumor-induced osteolysis. In this condition, bone cancers or bone metastases induce localized osteolysis that causes pain, bone weakness and fractures. Such localized osteolysis also permits tumors to grow larger by creating more space for them in the bone and releasing growth factors from the bone matrix. Cancers presently known to cause tumor-induced osteolysis include hematological malignancies (e.g., myeloma and lymphoma) and solid tumors (e.g., breast, prostate, lung, renal and thyroid), all of which the present invention contemplates treating.

As used herein, the term treatment includes prophylaxis as well as treatment of an existing condition.

Accordingly, another aspect of this invention provides a method of treating diseases or medical conditions in a mammal, wherein said disease or condition is treatable with an inhibitor or Trk-A and/or Trk-B, comprising administering to said mammal one or more compounds of Formula I or a pharmaceutically acceptable salt thereof in an amount effective to treat or prevent said disorder. In a particular embodiment, the invention provides a method of treating pain, cancer, inflammation, neurodegenerative disease or *Typanosoma cruzi* infection in a mammal, which comprises administering to said mammal a therapeutically effective amount of a compound of Formula I or a pharmaceutically acceptable salt thereof. In another embodiment, the invention provides a method of treating osteolytic disease in a mammal, which comprises administering to said mammal a therapeutically effective amount of a compound of Formula I or a pharmaceutically acceptable salt thereof.

The compounds of the present invention can be used in combination with one or more additional drugs that work by the same or a different mechanism of action. Examples include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

The phrase "effective amount" means an amount of compound that, when administered to a mammal in need of such treatment, is sufficient to (i) treat or prevent a particular disease, condition, or disorder which can be treated with an inhibitor or Trk-A and/or Trk-B, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

According to another aspect, the present invention provides a compound of Formula I or a pharmaceutically acceptable salt thereof, for use in therapy, such as the treatment of a condition treatable with an inhibitor or Trk-A and/or Trk-B, such as one or more conditions described herein.

According to a further aspect, the present invention provides the use of a compound of Formula I or a pharmaceutically acceptable salt thereof, in the treatment of a condition that can be treated with an inhibitor or Trk-A and/or Trk-B, such as a condition as defined hereinabove. In one embodiment, the invention provides a compound of Formula I, or a pharmaceutically acceptable salt thereof, for use in the treatment of pain, cancer, inflammation, neurodegenerative disease or *Typanosoma cruzi* infection.

In one embodiment, a compound of the invention is selected from any one of:

(R)-1-(6-(2-(2,5-difluorophenyl)pyrrolidin-1-yl)imidazo[12,-b]pyridazin-3-yl)-3-phenylurea;
(R)—N-(6-(2-(2,5-difluorophenyl)pyrrolidin-1-yl)imidazo[1,2-b]pyridazin-3-yl)morpholine-4-carboxamide;
(R)—N-(6-(2-(2,5-difluorophenyl)pyrrolidin-1-yl)imidazo[1,2-b]pyridazin-3-yl)acetamide;
(R)—N-(6-(2-(2,5-difluorophenyl)pyrrolidin-1-yl)imidazo[1,2-b]pyridazin-3-yl)-4-(methylsulfonamido)benzamide;
(R)-1-(3-cyanophenyl)-3-(6-(2-(2,5-difluorophenyl)pyrrolidin-1-yl)imidazo[1,2-b]pyridazin-3-yl)urea;
(R)-1-(4-cyanophenyl)-3-(6-(2-(2,5-difluorophenyl)pyrrolidin-1-yl)imidazo[1,2-b]pyridazin-3-yl)urea;
(R)-1-(2,4-dichlorophenyl)-3-(6-(2-(2,5-difluorophenyl)pyrrolidin-1-yl)imidazo[1,2-b]pyridazin-3-yl)urea;
(R)-1-(6-(2-(2,5-difluorophenyl)pyrrolidin-1-yl)imidazo[1,2-b]pyridazin-3-yl)-3-(3-(trifluoromethyl)phenyl)urea;
(R)-1-(3,5-dichlorophenyl)-3-(6-(2-(2,5-difluorophenyl)pyrrolidin-1-yl)imidazo[1,2-b]pyridazin-3-yl)urea;
(S)—N-(6-((R)-2-(2,5-difluorophenyl)pyrrolidin-1-yl)imidazo[1,2-b]pyridazin-3-yl)-3-hydroxypyrrolidine-1-carboxamide;
(R)—N-(6-((R)-2-(2,5-difluorophenyl)pyrrolidin-1-yl)imidazo[1,2-b]pyridazin-3-yl)-3-hydroxypyrrolidine-1-carboxamide;
(R)-tert-butyl 1-(6-(2-(2,5-difluorophenyl)pyrrolidin-1-yl)imidazo[1,2-b]pyridazin-3-ylcarbamoyl)piperidin-4-ylcarbamate;
(R)—N-(6-(2-(2,5-difluorophenyl)pyrrolidin-1-yl)imidazo[1,2-b]pyridazin-3-yl)-3-hydroxyazetidine-1-carboxamide;
(R)-tert-butyl 1-(6-(2-(2,5-difluorophenyl)pyrrolidin-1-yl)imidazo[1,2-b]pyridazin-3-ylcarbamoyl)azetidin-3-ylcarbamate;
(R)-tert-butyl 4-(6-(2-(2,5-difluorophenyl)pyrrolidin-1-yl)imidazo[1,2-b]pyridazin-3-ylcarbamoyl)piperazine-1-carboxylate;
(R)-3-(6-(2-(2,5-difluorophenyl)pyrrolidin-1-yl)imidazo[1,2-b]pyridazin-3-yl)-1,1-dimethylurea;
tert-Butyl 1-(6-((R)-2-(2,5-difluorophenyl)pyrrolidin-1-yl)imidazo[1,2-b]pyridazin-3-ylcarbamoyl)piperidin-3-ylcarbamate;
(R)-4-amino-N-(6-(2-(2,5-difluorophenyl)pyrrolidin-1-yl)imidazo[1,2-b]pyridazin-3-yl)piperidine-1-carboxamide;
(R)-3-amino-N-(6-(2-(2,5-difluorophenyl)pyrrolidin-1-yl)imidazo[1,2-b]pyridazin-3-yl)azetidine-1-carboxamide;
(R)—N-(6-(2-(2,5-difluorophenyl)pyrrolidin-1-yl)imidazo[1,2-b]pyridazin-3-yl)piperazine-1-carboxamide;
3-Amino-N-(6-((R)-2-(2,5-difluorophenyl)pyrrolidin-1-yl)imidazo[1,2-b]pyridazin-3-yl)piperidine-1-carboxamide;
(R)-1-(6-(2-(2,5-difluorophenyl)pyrrolidin-1-yl)imidazo[1,2-b]pyridazin-3-yl)-3-(4-fluorophenyl)urea;
tert-Butyl 3-(6-((R)-2-(2,5-difluorophenyl)pyrrolidin-1-yl)imidazo[1,2-b]pyridazin-3-ylcarbamoyl)-3,8-diazabicyclo[3.2.1]octane-8-carboxylate;
N-(6-((R)-2-(2,5-difluorophenyl)pyrrolidin-1-yl)imidazo[1,2-b]pyridazin-3-yl)-3,8-diazabicyclo[3.2.1]octane-3-carboxamide;
(R)—N-(6-(2-(2,5-difluorophenyl)pyrrolidin-1-yl)imidazo[1,2-b]pyridazin-3-yl)-4-hydroxypiperidine-1-carboxamide;
(R)—N-(6-(2-(2,5-difluorophenyl)pyrrolidin-1-yl)imidazo[1,2-b]pyridazin-3-yl)piperidine-1-carboxamide;
(R)-1-(6-(2-(2,5-difluorophenyl)pyrrolidin-1-yl)imidazo[1,2-b]pyridazin-3-yl)urea;
(R)-1-(6-(2-(2,5-difluorophenyl)pyrrolidin-1-yl)imidazo[1,2-b]pyridazin-3-yl)-3-methylurea;
(R)-1-tert-butyl-3-(6-(2-(2,5-difluorophenyl)pyrrolidin-1-yl)imidazo[1,2-b]pyridazin-3-yl)urea;
(R)-1-(6-(2-(2,5-difluorophenyl)pyrrolidin-1-yl)imidazo[1,2-b]pyridazin-3-yl)-3-(4-methoxyphenyl)urea;
(R)-ethyl 1-(6-(2-(2,5-difluorophenyl)pyrrolidin-1-yl)imidazo[1,2-b]pyridazin-3-ylcarbamoyl)piperidine-4-carboxylate;
(R)-1-(6-(2-(2,5-difluorophenyl)pyrrolidin-1-yl)imidazo[1,2-b]pyridazin-3-yl)-3-(3,4,5-trimethoxyphenyl)urea;
(R)-1-(6-(2-(2,5-difluorophenyl)pyrrolidin-1-yl)imidazo[1,2-b]pyridazin-3-yl)-3-(3,5-dimethylisoxazol-4-yl)urea;
(R)-1-(6-(2-(2,5-difluorophenyl)pyrrolidin-1-yl)imidazo[1,2-b]pyridazin-3-ylcarbamoyl)piperidine-4-carboxylic acid;
N-(6-((R)-2-(2,5-difluorophenyl)pyrrolidin-1-yl)imidazo[1,2-b]pyridazin-3-yl)-3,5-dimethylpiperazine-1-carboxamide;
(R)-tert-butyl 4-(6-((R)-2-(2,5-difluorophenyl)pyrrolidin-1-yl)imidazo[1,2-b]pyridazin-3-ylcarbamoyl)-2-methylpiperazine-1-carboxylate;
(S)-tert-butyl 4-(6-((R)-2-(2,5-difluorophenyl)pyrrolidin-1-yl)imidazo[1,2-b]pyridazin-3-ylcarbamoyl)-2-methylpiperazine-1-carboxylate;

(R)—N-(6-((R)-2-(2,5-difluorophenyl)pyrrolidin-1-yl)imidazo[1,2-b]pyridazin-3-yl)-3-methylpiperazine-1-carboxamide;
(S)—N-(6-((R)-2-(2,5-difluorophenyl)pyrrolidin-1-yl)imidazo[1,2-b]pyridazin-3-yl)-3-methylpiperazine-1-carboxamide;
(3R,4R)—N-(6-((R)-2-(2,5-difluorophenyl)pyrrolidin-1-yl) imidazo[1,2-b]pyridazin-3-yl)-3,4-dihydroxypyrrolidine-1-carboxamide;
(R)-1-(6-(2-(2,5-difluorophenyl)pyrrolidin-1-yl)imidazo[1,2-b]pyridazin-3-ylcarbamoyl)piperidin-4-sulfone;
(R)—N-(6-(2-(2,5-difluorophenyl)pyrrolidin-1-yl)imidazo [1,2-b]pyridazin-3-yl)-3-oxopiperazine-1-carboxamide;
N-(6-(2-(3-fluorophenyl)piperidin-1-yl)imidazo[1,2-b] pyridazin-3-yl)-3-hydroxyazetidine-1-carboxamide;
(R)—N-(6-(2-(2,5-difluorophenyl)pyrrolidin-1-yl)imidazo [1,2-b]pyridazin-3-yl)-3,3-difluoropyrrolidine-1-carboxamide;
(R)—N-(6-(2-(2,5-difluorophenyl)pyrrolidin-1-yl)imidazo [1,2-b]pyridazin-3-yl)-3,3-difluoroazetidine-1-carboxamide;
(R)—N-(6-(2-(2,5-difluorophenyl)pyrrolidin-1-yl)imidazo [1,2-b]pyridazin-3-yl)azetidine-1-carboxamide;
(R)-3-(6-(2-(2,5-difluorophenyl)pyrrolidin-1-yl)imidazo[1,2-b]pyridazin-3-yl)-1-(2-hydroxyethyl)-1-methylurea;
(R)-tert-butyl 4-(6-(2-(2,5-difluorophenyl)pyrrolidin-1-yl) imidazo[1,2-b]pyridazin-3-ylcarbamoyl)-2,2-dimethylpiperazine-1-carboxylate;
(S)-tert-butyl 4-(6-((R)-2-(2,5-difluorophenyl)pyrrolidin-1-yl)imidazo[1,2-b]pyridazin-3-ylcarbamoyl)-2-isopropylpiperazine-1-carboxylate;
(R)—N-(6-(2-(2,5-difluorophenyl)pyrrolidin-1-yl)imidazo [1,2-b]pyridazin-3-yl)-3,3-dimethylpiperazine-1-carboxamide;
(S)—N-(6-((R)-2-(2,5-difluorophenyl)pyrrolidin-1-yl)imidazo[1,2-b]pyridazin-3-yl)-3-isopropylpiperazine-1-carboxamide;
(R)—N-(6-(2-(2,5-difluorophenyl)pyrrolidin-1-yl)imidazo [1,2-b]pyridazin-3-yl)-3-(hydroxymethyl)azetidine-1-carboxamide;
(R)—N-(6-(2-(2,5-difluorophenyl)pyrrolidin-1-yl)imidazo [1,2-b]pyridazin-3-yl)-3-methoxyazetidine-1-carboxamide;
(R)—N-(6-(2-(2,5-difluorophenyl)pyrrolidin-1-yl)imidazo [1,2-b]pyridazin-3-yl)-3-hydroxy-3-methylazetidine-1-carboxamide;
(R)-1-(6-(2-(2,5-difluorophenyl)pyrrolidin-1-yl)imidazo[1,2-b]pyridazin-3-ylcarbamoyl)azetidin-3-yl isobutyrate;
(R)—N-(6-(2-(2,5-difluorophenyl)pyrrolidin-1-yl)imidazo [1,2-b]pyridazin-3-yl)-1-methyl-6-oxo-1,6-dihydropyridine-3-carboxamide;
(R)—N-(6-(2-(2,5-difluorophenyl)pyrrolidin-1-yl)imidazo [1,2-b]pyridazin-3-yl)-1-methyl-6-oxo-1,6-dihydropyridazine-3-carboxamide;
(R)—N-(6-(2-(2,5-difluorophenyl)pyrrolidin-1-yl)imidazo [1,2-b]pyridazin-3-yl)-4-methylpiperazine-1-carboxamide;
(R)—N-(6-(2-(2,5-difluorophenyl)pyrrolidin-1-yl)imidazo [1,2-b]pyridazin-3-yl)-4-hydroxy-4-(trifluoromethyl)piperidine-1-carboxamide;
(R)—N-(6-(2-(2,5-difluorophenyl)pyrrolidin-1-yl)imidazo [1,2-b]pyridazin-3-yl)-2,2,2-trifluoroacetamide;

and salts thereof. Particular examples of salts include hydrochloride and trifluoroacetate salts.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

Abbreviations used in the Examples have the following meanings:
CDI: carbonyl diimidazole
HATU: 2(1H-azabenzotriazol-1-yl)-1,1,3,3-tetramethyl uranium hexafluoro-phosphate methanaminium
DIEA: diisopropylethylamine
DMF: dimethylformamide
MTBE: methyl t-butyl ether
TFA: trifluoroacetic acid
ACN: acetonitrile
IPA: isopropyl alcohol

Example A

TrkA ELISA Assay

An enzyme-linked immunosorbant assay (ELISA) was used to assess TrkA kinase activity in the presence of inhibitors. Immulon 4HBX 384-well microtiter plates (Thermo part #8755) were coated with a 0.025 mg/mL solution of poly (Glu, Ala, Tyr; 6:3:1; Sigma P3899). Various concentrations of test compound, 2.5 nM TrkA (Invitrogen Corp., histidine-tagged recombinant human TrkA, cytoplasmic domain), and 500 μM ATP were incubated for 25 minutes at ambient temperature in the coated plates while shaking. The assay buffer consisted of 25 mM MOPS pH 7.5, 0.005% (v/v) Triton X-100 and 5 mM $MgCl_2$. The reaction mixture was removed from the plate by washing with PBS containing 0.1% (v/v) Tween 20. The phosphorylated reaction product was detected using 0.2 μg/mL of a phosphotyrosine specific monoclonal antibody (clone PY20) conjugated to horseradish peroxidase in conjunction with the TMB Peroxidase Substrate System (KPL). After the addition of 1M phosphoric acid, the chromogenic substrate color intensity was quantitated via absorbance at 450 nm. $IC_{50}$ values were calculated using either a 4 or 5-parameter logistic curve fit.

In this assay, compounds of the invention had an average $IC_{50}$ below 1000 nM. Certain compounds had an average $IC_{50}$ below 100 nM.

Table 1 provides $IC_{50}$ values for compounds of the invention when tested in this assay.

TABLE 1

| Example # | TrkA Elisa Enzyme $IC_{50}$ (nM) |
| --- | --- |
| 1 | 8.3 |
| 2 | 23.7 |
| 3 | 5.4 |

TABLE 1-continued

| Example # | TrkA Elisa Enzyme IC$_{50}$ (nM) |
|---|---|
| 4 | 2.1 |
| 5 | 74.2 |
| 6 | 10.7 |
| 7 | 39.4 |
| 8 | 507.8 |
| 9 | 716.7 |
| 10 | 3.8 |
| 11 | 15.5 |
| 12 | 17.2 |
| 13 | 9.4 |
| 14 | 23.2 |
| 15 | 33.6 |
| 16 | 18 |
| 17 | 13.8 |
| 18 | 52.9 |
| 19 | 126.3 |
| 20 | 94.7 |
| 21 | 42 |
| 22 | 10 |
| 23 | 75.5 |
| 24 | 107.1 |
| 25 | 13.8 |
| 26 | 7.1 |
| 27 | 77.1 |
| 28 | 65.7 |
| 29 | 9.8 |
| 30 | 5.5 |
| 31 | 20.1 |
| 32 | 175.6 |
| 33 | 901 |
| 34 | 64.4 |
| 35 | 49.6 |
| 36 | 13 |
| 37 | 40.6 |
| 38 | 47.9 |
| 39 | 29.9 |
| 40 | 2.2 |
| 41 | 884.4 |
| 42 | 26.2 |
| 43 | 215.6 |
| 44 | 22.7 |
| 45 | 92 |
| 46 | 17.9 |
| 47 | 10.3 |
| 48 | 8.3 |
| 49 | 857 |
| 50 | 60.6 |
| 51 | 27.7 |
| 52 | 14 |
| 53 | 16.4 |
| 54 | 8.9 |
| 55 | 19.4 |
| 56 | 10.2 |
| 57 | 2.3 |
| 58 | 53.2 |
| 59 | 16.5 |
| 60 | 22 |

Example B

TrkA and TrkB Omnia Assay

Trk enzymatic selectivity was assessed using Omnia™ Kinase Assay reagents from Invitrogen Corp. Enzyme (either TrkA or TrkB from Invitrogen Corp.) and test compound (various concentrations) were incubated for 10 minutes at ambient temperature in a 384-well white polypropylene plate (Nunc catalog #267462). Omnia Tyr Peptide #4 (for TrkA) or #5 (for TrkB), as well as ATP, were then added to the plate. Final concentrations were as follows: 20 nM enzyme, 500 µM of ATP for TrkA assay or 1 mM ATP for TrkB assay, 10 µM peptide substrate. The assay buffer consisted of 25 mM MOPS pH 7.5, 0.005% (v/v) Triton X-100 and 5 mM MgCl$_2$. The production of phosphorylated peptide was monitored continuously for 70 minutes using a Molecular Devices FlexStation II$^{384}$ microplate reader (excitation=360 nm; emission=485 nm). Initial rates were calculated from the progress curves. IC$_{50}$ values were then calculated from these rates using either a 4 or 5-parameter logistic curve fit.

In this assay, compounds of the invention had an average IC$_{50}$ below 1000 nM. Certain compounds had an average IC$_{50}$ below 100 nM.

Preparation A

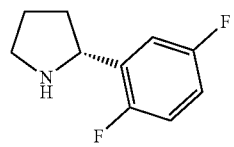 [SMILES: Fc1ccc(F)c([C@H]2CCCN2)c1]

Preparation of (R)-2-(2,5-difluorophenyl)pyrrolidine

Step A: Preparation of (R)-tert-butyl 2-(2,5-difluorophenyl)pyrrolidine-1-carboxylate A solution of tert-butyl pyrrolidine-1-carboxylate (20 g, 116.8 mmol) and (−)sparteine (32.9, 140 mmol) in MTBE (360 mL) was cooled to −78° C., and sec-BuLi (100 mL, 140 mmol, 1.4 M in cyclohexane) was introduced drop-wise via cannula, keeping the internal temperature under −70° C. The resulting solution was stirred for 3 hours at −78° C., followed by addition of a solution of ZnCl$_2$ (93.4 mL, 93.4 mmol, 1M in Et$_2$O) drop-wise with rapid stirring, keeping the internal temperature below −65° C. The resulting light suspension was stirred at −78° C. for 30 minutes and then warmed to ambient temperature. The resulting mixture was charged with 2-bromo-1,4-difluorobenzene (14.5 mL, 128 mmol), followed by Pd(OAc)$_2$ (1.31 g, 5.8 mmol) and t-Bu$_3$P-HBF$_4$ (2.03 g, 7.0 mmol) in one portion. After stirring overnight at ambient temperature, 10.5 mL of NH$_4$OH solution was added and the reaction was stirred for another hour. The resulting slurry was filtered through CELITE and washed with Et$_2$O (1 L). The filtrate was washed with HCl (0.5 L, 1M aq.) and brine. The organic layer was filtered and concentrated, and the crude product was purified by silica column chromatography, eluting with 5-10% EtOAc/hexanes to give product (R)-tert-butyl 2-(2,5-difluorophenyl)pyrrolidine-1-carboxylate as yellow oil (23.9 g, 72% yield).

Step B: Preparation of (R)-2-(2,5-difluorophenyl)pyrrolidine

To (R)-tert-butyl 2-(2,5-difluorophenyl)pyrrolidine-1-carboxylate (23.9 g, 84.4 mmol) was added 56.2 mL 4N HCl (dioxane). After stirring at ambient temperature for 2 hours, 200 mL of ether was added and the mixture was stirred for 10 minutes. The resulting slurry was filtered, yielding the hydrochloride salt of the product as a white solid (17.2 g). To obtain the free base, the HCl salt product was dispersed in a mixture of EtOAc (200 mL) and NaOH solution (100 mL, 2 N aq.) The layers were separated and the aqueous layer was extracted with EtOAc. The combined organic extracts were filtered and concentrated to give the desired product as a liquid (13.2 g, 85% yield).

The Enantiomeric Excess (ee %) of (R)-2-(2,5-difluorophenyl)pyrrolidine was determined as follows: To an ethanol solution of (R)-2-(2,5-difluorophenyl)pyrrolidine was added excess N-(2,4-dinitro-5-fluorophenyl)-L-alanine amide (FDAA, Marfey's reagent). The mixture was heated to reflux for approximately two minutes. After cooling to ambient temperature, the reaction mixture was diluted with acetonitrile and injected onto HPLC (YMC ODS-AQ 4.6× 50 mm 3 μm 120 Å column; mobile phase: 5-95% solvent B in A; solvent A: H$_2$O/1% IPA/10 mM ammonium acetate, and solvent B: ACN/1% IPA/10 mM ammonium acetate; flow rate: 2 mL/min) to determine the enantiomeric excess of the product by calculating the peak areas of the two diastereomeric derivatives formed. A 1:1 racemic sample was prepared according the same procedure described herein, replacing (R)-2-(2,5-difluorophenyl)pyrrolidine with (rac)-2-(2,5-difluorophenyl)pyrrolidine. The ee % of the product obtained as described above was determined to be >93%.

Preparation B

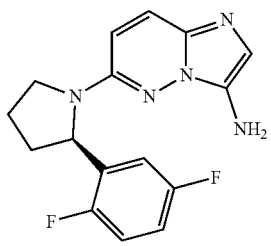 [SMILES: Nc1cnc2ccc(N3CCC[C@@H]3c3cc(F)ccc3F)nn12]

Preparation of (R)-6-(2-(2,5-difluorophenyl)pyrrolidin-1-yl)imidazo[1,2-b]pyridazin-3-amine Step 1: Preparation of 6-chloro-3-nitroimidazo[1,2-b]pyridazine 6-Chloroimidazo[1,2-b]pyridazine (4.95 g, 31.6 mmol) [purchased from Combi-Blocks] was dissolved in 60 mL concentrated sulfuric acid, cooled in an ice bath, and nitric acid (9.9 mL, 158 mmol) was added dropwise while stirring. The reaction was stirred at 0° C. for 30 minutes, then at ambient temperature for 4.5 hours to reach completion. The reaction was poured onto ice, and the resulting aqueous mixture was neutralized with 50% NaOH aqueous solution and then extracted with EtOAc (3×400 mL). The organic layers were combined and washed with water (2×400 mL) and brine (400 mL), dried (Na$_2$SO$_4$), filtered and concentrated to yield the product as a yellowish powder (5.7 g, 91% yield).

Step 2: Preparation of (R)-6-(2-(2,5-difluorophenyl) pyrrolidin-1-yl)-3-nitroimidazo[1,2-b]pyridazine A suspension of 6-chloro-3-nitroimidazo[1,2-b] pyridazine (1.0 g, 5.0 mmol) and (R)-2-(2,5-difluorophenyl) pyrrolidine (Prepared as described in Preparation A; 1.9 g, 11 mmol) in n-butanol (4.6 mL, 50 mmol) was sealed in a pressure reaction tube and stirred in a 140° C. oil bath overnight. After cooling to ambient temperature, the reaction mixture was diluted with EtOAc (250 mL), then washed with water (2×150 mL) and brine (150 mL), filtered through a Biotage Phase Separator filter paper and concentrated. The crude material was purified by silica gel chromatography, eluting with 2:1 EtOAc/hexanes to yield the product as a foamy yellow powder (1.3 g, 75% yield).

Step 3: Preparation of (R)-6-(2-(2,5-difluorophenyl) pyrrolidin-1-yl)imidazo[1,2-b]pyridazin-3-amine To a mixture of (R)-6-(2-(2,5-difluorophenyl)pyrrolidin-1-yl)-3-nitroimidazo[1,2-b]pyridazine (4.17 g, 12.1 mmol) and SnCl$_2$ dihydrate (10.9 g, 48.4 mmol) in a flask was added 200 mL EtOH to form a suspension. The reaction was heated at 70° C. for 1 hour to reach completion. After cooling to ambient temperature, the reaction mixture was concentrated. Water (200 mL) was added to the resulting crude solid residue, and the mixture was briefly sonicated and then vacuum-filtered. The filtrate pH was neutralized with 6N NaOH solution and extracted with DCM (3×250 mL). The combined organic layers were washed with brine (200 mL), dried over Na$_2$SO$_4$, and concentrated to yield the crude product as a yellowish foamy solid. The crude material was purified by C-18 reverse-phase column chromatography (eluent=5 to 60% acetonitrile/water) to provide the pure product as a light yellowish powder (3 g, 78% yield).

Example 1

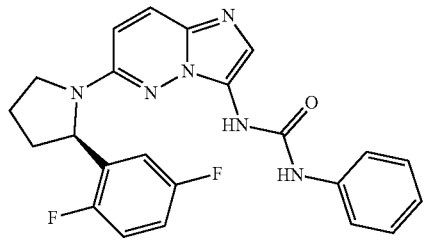 [SMILES: O=C(Nc1ccccc1)Nc1cnc2ccc(N3CCC[C@@H]3c3cc(F)ccc3F)nn12]

Preparation of (R)-1-(6-(2-(2,5-difluorophenyl)pyrrolidin-1-yl)imidazo[1,2-b]pyridazin-3-yl)-3-phenylurea To a DCM (0.1 mL) solution of (R)-6-(2-(2,5-difluorophenyl)pyrrolidin-1-yl)imidazo[1,2-b]pyridazin-3-amine (Preparation B; 6 mg, 0.019 mmol) cooled in an ice bath was added the isocyanatobenzene (2.5 mg, 0.021 mmol) in DCM (0.1 mL) dropwise. The reaction was slowly warmed to ambient temperature and stirred for 1 hour. The reaction was diluted with DCM (2 mL), washed with water, and concentrated. The crude product was purified by silica gel chromatography (eluent=50% EtOAc/hexanes first, then 5% MeOH in DCM) to yield the pure final product as a solid (5 mg, 60%). MS (apci) m/z=435.2 (M+H).

Example 2

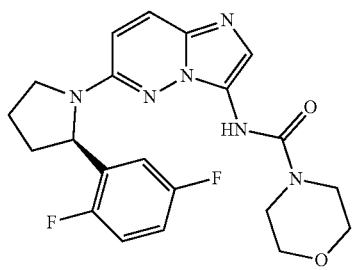 [SMILES: O=C(Nc1cnc2ccc(N3CCC[C@@H]3c3cc(F)ccc3F)nn12)N1CCOCC1]

(R)—N-(6-(2-(2,5-difluorophenyl)pyrrolidin-1-yl)imidazo[1,2-b]pyridazin-3-yl)morpholine-4-carboxamide To a DCM (1.9 mL) solution of (R)-6-(2-(2,5-difluorophenyl)pyrrolidin-1-yl)imidazo[1,2-b]pyridazin-3-amine (Preparation B; 72 mg, 0.19 mmol) was added 1,1'-carbonyldiimidazole (CDI) (47 mg, 0.29 mmol) at ambient temperature in one portion. After stirring for 2 hours, morpholine (34 mg, 0.39 mmol) was added in one portion. The reaction was stirred for another hour before it was concentrated, then directly purified by reverse-phase column chromatography, eluting with 5 to 60% acetonitrile/water to yield (R)—N-(6-(2-(2,5-difluorophenyl)pyrrolidin-1-yl)imidazo[1,2-b]pyridazin-3-yl)morpholine-4-carboxamide as a solid (64 mg, 77% yield). MS (apci) m/z=429.1 (M+H).

Example 3

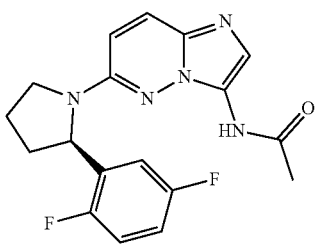 [SMILES: CC(=O)Nc1cnc2ccc(N3CCC[C@@H]3c3cc(F)ccc3F)nn12]

(R)—N-(6-(2-(2,5-difluorophenyl)pyrrolidin-1-yl)imidazo[1,2-b]pyridazin-3-yl)acetamide To a DCM (0.1 mL) solution of (R)-6-(2-(2,5-difluorophenyl)pyrrolidin-1-yl)imidazo[1,2-b]pyridazin-3-amine (Preparation B; 6 mg, 0.019 mmol) cooled in an ice bath was added acetic anhydride (2.1 mg, 0.021 mmol), followed by pyridine (2 mg, 0.025 mmol). The reaction was warmed to ambient temperature and stirred for 1 hour before it was concentrated and directly purified by reverse-phase column chromatography, eluting with 5 to 60% acetonitrile/water to yield (R)—N-(6-(2-(2,5-difluorophenyl)pyrrolidin-1-yl)imidazo[1,2-b]pyridazin-3-yl)acetamide as an off-white solid (6 mg, 81% yield). MS (apci) m/z=358.2 (M+H).

Example 4

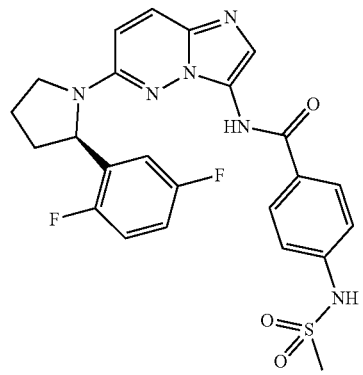 [SMILES: CS(=O)(=O)Nc1ccc(C(=O)Nc2cnc3ccc(N4CCC[C@@H]4c4cc(F)ccc4F)nn23)cc1]

(R)—N-(6-(2-(2,5-difluorophenyl)pyrrolidin-1-yl)imidazo[1,2-b]pyridazin-3-yl)-4-(methylsulfonamido)benzamide A reaction vial was charged with (R)-6-(2-(2,5-difluorophenyl)pyrrolidin-1-yl)imidazo[1,2-b]pyridazin-3-amine (Preparation B; 30 mg, 0.095 mmol), 4-(methylsulfonamido)benzoic acid (41 mg, 0.19 mmol), and 2(1H-azabenzotriazol-1-yl)-1,1,3,3-tetramethyl uranium hexafluorophophate methanaminium (HATU; 72 mg, 0.19 mmol). DMF (0.8 mL) was added to the mixture to make a solution. The reaction mixture was cooled in an ice bath for 10 minutes before DIEA (0.05 mL, 0.29 mmol) was added dropwise. After addition, reaction was warmed to ambient temperature and stirred overnight. The reaction mixture was diluted with EtOAc (20 mL), washed with water and brine (10 mL each), and concentrated. The crude material was purified by reverse-phase column chromatography, eluting with 5 to 60% acetonitrile/water to yield (R)—N-(6-(2-(2,5-difluorophenyl)pyrrolidin-1-yl)imidazo[1,2-b]pyridazin-3-yl)-4-(methylsulfonamido)benzamide as a yellowish solid (13 mg, 27% yield). MS (apci negative) m/z=511.4 (M−H).

Example 5

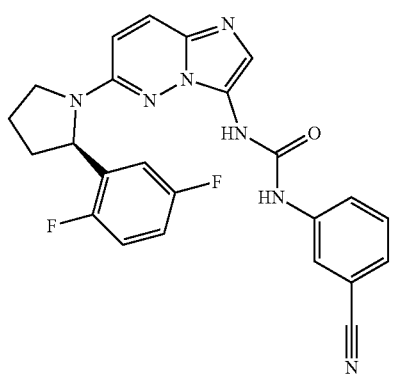 [SMILES: N#Cc1cccc(NC(=O)Nc2cnc3ccc(N4CCC[C@@H]4c4cc(F)ccc4F)nn23)c1]

(R)-1-(3-cyanophenyl)-3-(6-(2-(2,5-difluorophenyl)pyrrolidin-1-yl)imidazo[1,2-b]pyridazin-3-yl)urea To a DCM (0.1 mL) solution of (R)-6-(2-(2,5-difluorophenyl)pyrrolidin-1-yl)imidazo[1,2-b]pyridazin-3-amine (Preparation B; 6 mg, 0.019 mmol) cooled in an ice bath was added 3-cyanophenylisocyanate (14 mg, 0.095 mmol) in DCM (0.1 mL) drop-wise. The reaction was slowly warmed to ambient temperature and stirred for 1 hour. The reaction was diluted with DCM (2 mL), washed with water, and concentrated. The crude material was purified by reverse-phase column chromatography, eluting with 5 to 85% acetonitrile/water to yield the pure final product as a solid (3.2 mg, 37% yield). MS (apci) m/z=460.2 (M+H).

Example 6

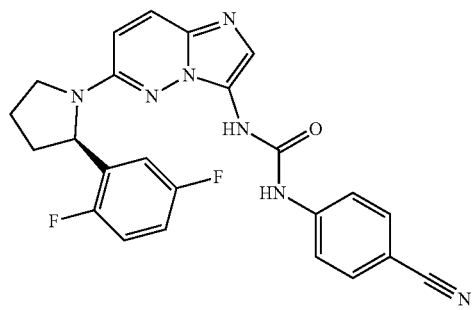 [SMILES: N#Cc1ccc(NC(=O)Nc2cnc3ccc(N4CCC[C@@H]4c4cc(F)ccc4F)nn23)cc1]

(R)-1-(4-cyanophenyl)-3-(6-(2-(2,5-difluorophenyl)pyrrolidin-1-yl)imidazo[1,2-b]pyridazin-3-yl)urea Prepared according to Example 5, replacing 3-cyanophenylisocyanate with 4-cyanophenylisocyanate to yield the final product as a solid. MS (apci) m/z=460.2 (M+H).

Example 7

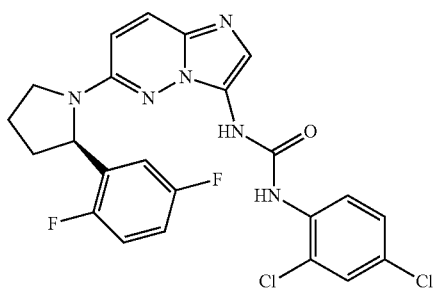 [SMILES: O=C(Nc1ccc(Cl)cc1Cl)Nc1cnc2ccc(N3CCC[C@@H]3c3cc(F)ccc3F)nn12]

(R)-1-(2,4-dichlorophenyl)-3-(6-(2-(2,5-difluorophenyl)pyrrolidin-1-yl)imidazo[1,2-b]pyridazin-3-yl)urea Prepared according to Example 5, replacing 3-cyanophenylisocyanate with 2,4-dichlorophenylisocyanate to yield the final product as a solid. MS (apci) m/z=503.1, 505.1 (M+H, M+3H).

Example 8

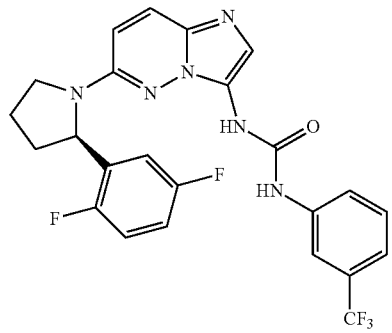 [SMILES: O=C(Nc1cccc(C(F)(F)F)c1)Nc1cnc2ccc(N3CCC[C@@H]3c3cc(F)ccc3F)nn12]

(R)-1-(6-(2-(2,5-difluorophenyl)pyrrolidin-1-yl)imidazo[1,2-b]pyridazin-3-yl)-3-(3-(trifluoromethyl)phenyl)urea Prepared according to Example 5, replacing 3-cyanophenylisocyanate with 3-trifluoromethylphenylisocyanate to yield the final product as a solid (6.5 mg, 68% yield). MS (apci) m/z=503.2 (M+H).

Example 9

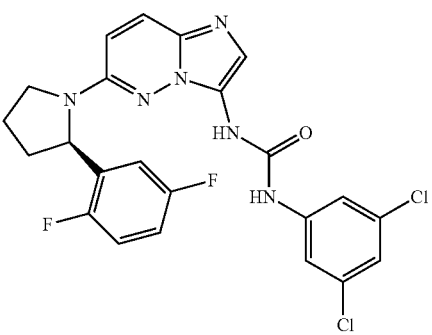 [SMILES: O=C(Nc1cc(Cl)cc(Cl)c1)Nc1cnc2ccc(N3CCC[C@@H]3c3cc(F)ccc3F)nn12]

(R)-1-(3,5-dichlorophenyl)-3-(6-(2-(2,5-difluorophenyl)pyrrolidin-1-yl)imidazo[1,2-b]pyridazin-3-yl)urea Prepared according to Example 5, replacing 3-cyanophenylisocyanate with 3,5-dichlorophenylisocyanate to yield the final product as a solid. MS (apci) m/z=503.1 (M+H), 505.1 (M+3H).

Example 10

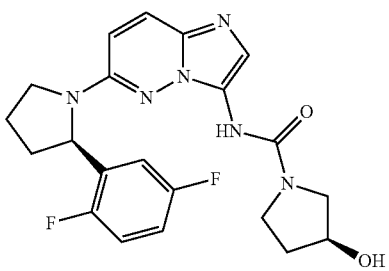 [SMILES: O=C(Nc1cnc2ccc(N3CCC[C@@H]3c3cc(F)ccc3F)nn12)N1CC[C@H](O)C1]

(S)—N-(6-((R)-2-(2,5-difluorophenyl)pyrrolidin-1-yl)imidazo[1,2-b]pyridazin-3-yl)-3-hydroxypyrrolidine-1-carboxamide Prepared according to the method of Example 2, replacing morpholine with (S)-pyrrolidin-3-ol [purchased from SUVEN Life Sciences] to yield the final product as a solid (79 mg, 68% yield). MS (apci) m/z=429.2 (M+H).

Example 11

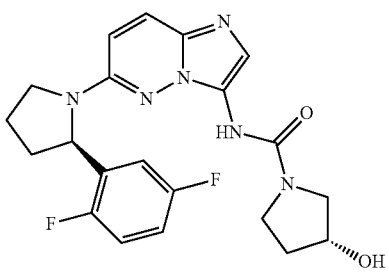 [SMILES: O=C(Nc1cnc2ccc(N3CCC[C@@H]3c3cc(F)ccc3F)nn12)N1CC[C@@H](O)C1]

(R)—N-(6-((R)-2-(2,5-difluorophenyl)pyrrolidin-1-yl)imidazo[1,2-b]pyridazin-3-yl)-3-hydroxypyrrolidine-1-carboxamide Prepared according to the method of Example 2, replacing morpholine with (R)-pyrrolidin-3-ol to yield the final product as a solid (8 mg, 77% yield). MS (apci) m/z=429.2 (M+H).

Example 11A

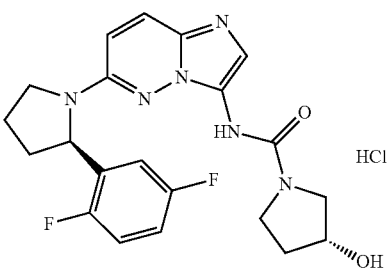 [SMILES: O=C(Nc1cnc2ccc(N3CCC[C@@H]3c3cc(F)ccc3F)nn12)N1CC[C@@H](O)C1 ; Cl]

(R)—N-(6-((R)-2-(2,5-difluorophenyl)pyrrolidin-1-yl) imidazo[1,2-b]pyridazin-3-yl)-3-hydroxypyrrolidine-1-carboxamide hydrochloride To a methanol (1 mL) solution of (S)—N-(6-((R)-2-(2,5-difluorophenyl)pyrrolidin-1-yl)imidazo[1,2-b]pyridazin-3-yl)-3-hydroxypyrrolidine-1-carboxamide (10.1 mg, 0.0236 mmol) was added HCl as a solution is dioxane (30 μL). After 5 minutes, the reaction was concentrated to provide (S)—N-(6-((R)-2-(2,5-difluorophenyl)pyrrolidin-1-yl)imidazo[1,2-b]pyridazin-3-yl)-3-hydroxypyrrolidine-1-carboxamide hydrochloride as a yellow solid.

Example 12

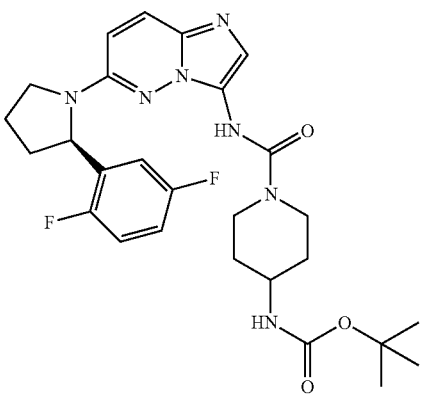 [SMILES: CC(C)(C)OC(=O)NC1CCN(C(=O)Nc2cnc3ccc(N4CCC[C@@H]4c4cc(F)ccc4F)nn23)CC1]

(R)-tert-butyl 1-(6-(2-(2,5-difluorophenyl)pyrrolidin-1-yl)imidazo[1,2-b]pyridazin-3-ylcarbamoyl) piperidin-4-ylcarbamate Prepared according to the method of Example 2, replacing morpholine with tert-butyl piperidin-4-ylcarbamate to yield the final product as a solid (10 mg, 76% yield). MS (apci) m/z=542.2 (M+H).

Example 13

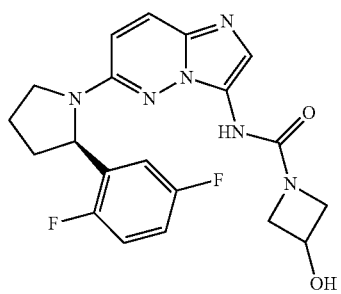 [SMILES: O=C(Nc1cnc2ccc(N3CCC[C@@H]3c3cc(F)ccc3F)nn12)N1CC(O)C1]

(R)—N-(6-(2-(2,5-difluorophenyl)pyrrolidin-1-yl) imidazo[1,2-b]pyridazin-3-yl)-3-hydroxyazetidine-1-carboxamide To a DCM (1 mL) solution of (R)-6-(2-(2,5-difluorophenyl)pyrrolidin-1-yl)imidazo[1,2-b]pyridazin-3-amine (Preparation B; 50 mg, 0.16 mmol) was added CDI (39 mg, 0.24 mmol) at ambient temperature in one portion while stirring. After 1 hour stirring, azetidin-3-ol hydrochloride (35 mg, 0.32 mmol) [purchased from Oakwood] was added in one portion, followed by addition of DIEA (83 μL, 0.48 mmol). The reaction mixture was briefly sonicated to help break up the solid particles from azetidine material. After 30 minute stirring at ambient temperature, the reaction was concentrated and directly purified by reverse-phase column chromatography, eluting with 5 to 50% acetonitrile/water to yield the final product as a pale-yellowish solid (65 mg, 99% yield). MS (apci) m/z=415.2 (M+H).

Example 14

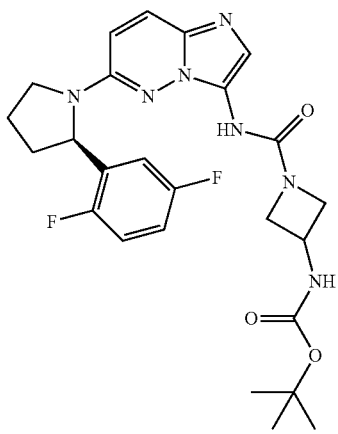 [SMILES: CC(C)(C)OC(=O)NC1CN(C(=O)Nc2cnc3ccc(N4CCC[C@@H]4c4cc(F)ccc4F)nn23)C1]

(R)-tert-butyl 1-(6-(2-(2,5-difluorophenyl)pyrrolidin-1-yl)imidazo[1,2-b]pyridazin-3-ylcarbamoyl)azetidin-3-yl carbamate Prepared according to the method of Example 2, replacing morpholine with tert-butyl azetidin-3-ylcarbamate to yield the final product as a solid (10 mg, 80% yield). MS (apci) m/z=514.2 (M+H).

Example 15

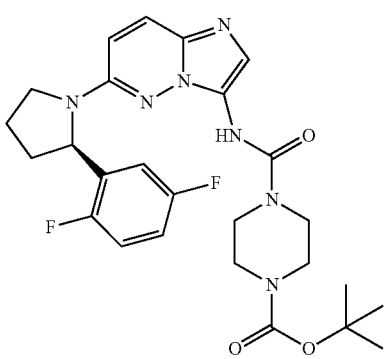 [SMILES: CC(C)(C)OC(=O)N1CCN(C(=O)Nc2cnc3ccc(N4CCC[C@@H]4c4cc(F)ccc4F)nn23)CC1]

(R)-tert-butyl 4-(6-(2-(2,5-difluorophenyl)pyrrolidin-1-yl)imidazo[1,2-b]pyridazin-3-ylcarbamoyl)piperazine-1-carboxylate Prepared according to the method of Example 2, replacing morpholine with tert-butyl piperazine-1-carboxylate to yield the final product as a solid (10 mg, 78% yield). MS (apci) m/z=528.2 (M+H).

Example 16

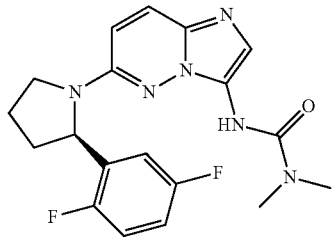 [SMILES: CN(C)C(=O)Nc1cnc2ccc(N3CCC[C@@H]3c3cc(F)ccc3F)nn12]

(R)-3-(6-(2-(2,5-difluorophenyl)pyrrolidin-1-yl)imidazo[1,2-b]pyridazin-3-yl)-1,1-dimethylurea Prepared according to the method of Example 2, replacing morpholine with dimethylamine to yield the final product as a solid (8 mg, 85% yield). MS (apci) m/z=387.2 (M+H).

Example 17

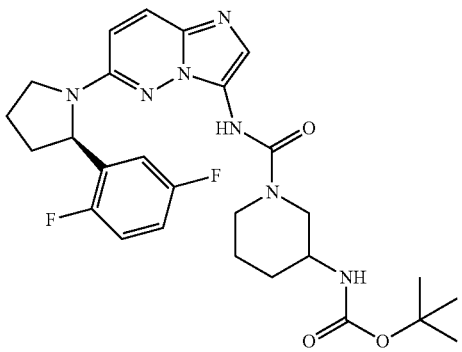 [SMILES: CC(C)(C)OC(=O)NC1CCCN(C(=O)Nc2cnc3ccc(N4CCC[C@@H]4c4cc(F)ccc4F)nn23)C1]

tert-Butyl 1-(6-((R)-2-(2,5-difluorophenyl)pyrrolidin-1-yl)imidazo[1,2-b]pyridazin-3-ylcarbamoyl)piperidin-3-ylcarbamate Prepared according to the method of Example 2, replacing morpholine with tert-butyl piperidin-3-ylcarbamate to yield the final product as a solid (10 mg, 76% yield). MS (apci) m/z=542.3 (M+H).

Example 18

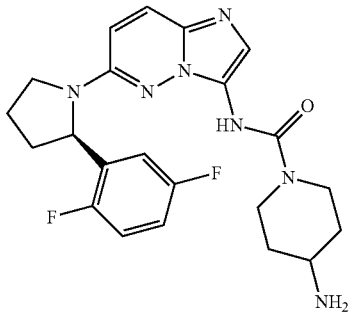 [SMILES: NC1CCN(C(=O)Nc2cnc3ccc(N4CCC[C@@H]4c4cc(F)ccc4F)nn23)CC1]

(R)-4-amino-N-(6-(2-(2,5-difluorophenyl)pyrrolidin-1-yl)imidazo[1,2-b]pyridazin-3-yl)piperidine-1-carboxamide (Example 12, 10 mg, 0.018 mmol) was dissolved in 0.2 mL DCM, followed by addition of 0.5 mL 4 N HCl (dioxane) solution in one portion. After stirring at ambient temperature overnight, the reaction was concentrated to yield the final product salt form as a light yellowish solid. MS (apci) m/z=442.1 (M+H).

Example 19

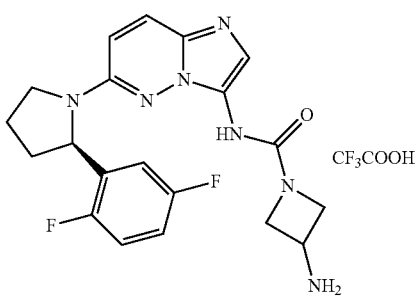 [SMILES: NC1CN(C(=O)Nc2cnc3ccc(N4CCC[C@@H]4c4cc(F)ccc4F)nn23)C1 ; "CF3COOH"]

(R)-3-amino-N-(6-(2-(2,5-difluorophenyl)pyrrolidin-1-yl)imidazo[1,2-b]pyridazin-3-yl)azetidine-1-carboxamide trifluoroacetate (R)-tert-butyl 1-(6-(2-(2,5-difluorophenyl)pyrrolidin-1-yl)imidazo[1,2-b]pyridazin-3-ylcarbamoyl)azetidin-3-ylcarbamate (Example 14; 10 mg, 0.019 mmol) was dissolved in 0.5 mL 50% TFA in DCM and stirred at ambient temperature for 2 hours. The reaction is concentrated, treated with ether, and concentrated again to yield the final product salt form as a white solid. MS (apci) m/z=414.2 (M+H).

Example 20

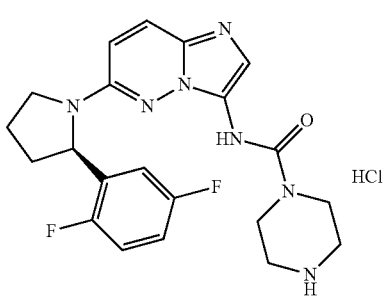 [SMILES: O=C(Nc1cnc2ccc(N3CCC[C@@H]3c3cc(F)ccc3F)nn12)N1CCNCC1 ; Cl]

(R)—N-(6-(2-(2,5-difluorophenyl)pyrrolidin-1-yl)imidazo[1,2-b]pyridazin-3-yl)piperazine-1-carboxamide hydrochloride (R)-tert-butyl 4-(6-(2-(2,5-difluorophenyl)pyrrolidin-1-yl)imidazo[1,2-b]pyridazin-3-ylcarbamoyl)piperazine-1-carboxylate (Example 15; 10 mg, 0.019 mmol) was dissolved in 0.2 mL DCM, followed by addition of 0.5 mL 4 N HCl (dioxane) solution in one portion. After stirring at ambient temperature overnight, the reaction was concentrated to yield the final product salt form as a light yellowish solid. MS (apci) m/z=428.2 (M+H).

Example 21

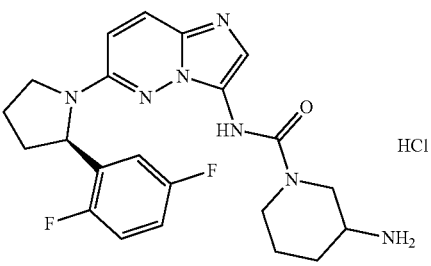 [SMILES: NC1CCCN(C(=O)Nc2cnc3ccc(N4CCC[C@@H]4c4cc(F)ccc4F)nn23)C1 ; Cl]

3-Amino-N-(6-((R)-2-(2,5-difluorophenyl)pyrrolidin-1-yl)imidazo[1,2-b]pyridazin-3-yl)piperidine-1-carboxamide hydrochloride tert-Butyl 1-(6-((R)-2-(2,5-difluorophenyl)pyrrolidin-1-yl)imidazo[1,2-b]pyridazin-3-ylcarbamoyl)piperidin-3-ylcarbamate (Example 17; 10 mg, 0.018 mmol) was dissolved in 0.1 mL DCM, followed by addition of 0.5 mL 4 N HCl (dioxane) solution in one portion. After stirring at ambient temperature overnight, the reaction was concentrated to yield the final product salt form as a light yellowish solid. MS (apci) m/z=442.1 (M+H).

Example 22

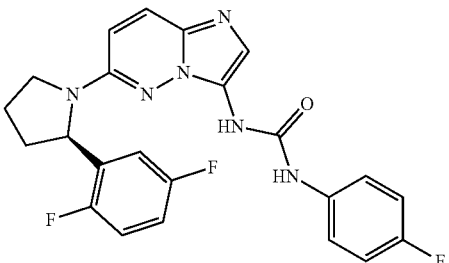

(R)-1-(6-(2-(2,5-difluorophenyl)pyrrolidin-1-yl)imidazo[1,2-b]pyridazin-3-yl)-3-(4-fluorophenyl)urea Prepared according to Example 5, replacing 3-cyanophenylisocyanate with 1-fluoro-4-isocyanatobenzene to yield the final product as a solid. MS (apci) m/z=453.2 (M+H).

Example 23

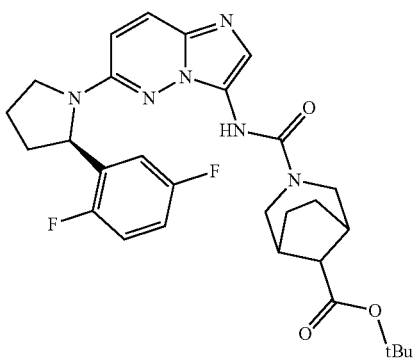 [SMILES: CC(C)(C)OC(=O)C1C2CCC1CN(C(=O)Nc1cnc3ccc(N4CCC[C@@H]4c4cc(F)ccc4F)nn13)C2]

tert-Butyl 3-(6-((R)-2-(2,5-difluorophenyl)pyrrolidin-1-yl)imidazo[1,2-b]pyridazin-3-ylcarbamoyl)-3,8-diazabicyclo[3.2.1]octane-8-carboxylate Prepared according to the method of Example 2, replacing morpholine with tert-butyl 3,8-diazabicyclo[3.2.1]octane-8-carboxylate to yield the final product as a solid. MS (apci) m/z=554.2 (M+H).

Example 24

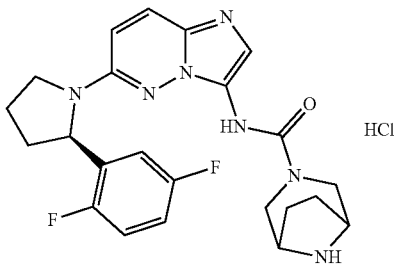 [SMILES: O=C(Nc1cnc2ccc(N3CCC[C@@H]3c3cc(F)ccc3F)nn12)N1CC2CCC(C1)N2 ; Cl]

N-(6-((R)-2-(2,5-difluorophenyl)pyrrolidin-1-yl)imidazo[1,2-b]pyridazin-3-yl)-3,8-diazabicyclo[3.2.1]octane-3-carboxamide hydrochloride tert-Butyl 3-(6-((R)-2-(2,5-difluorophenyl)pyrrolidin-1-yl)imidazo[1,2-b]pyridazin-3-ylcarbamoyl)-3,8-diazabicyclo[3.2.1]octane-8-carboxylate (Example 23, 10 mg, 0.018 mmol) was dissolved in 0.1 mL DCM, followed by addition of 0.5 mL 4 N HCl (dioxane) solution in one portion. After stirring at ambient temperature overnight, the reaction was concentrated to yield the final product salt form as a light yellowish solid. MS (apci) m/z=454.1 (M+H).

Example 25

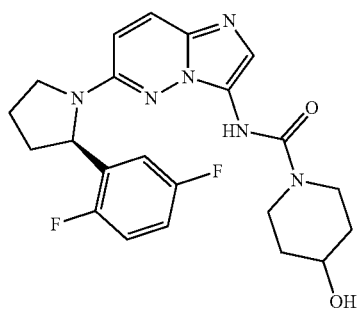 [SMILES: O=C(Nc1cnc2ccc(N3CCC[C@@H]3c3cc(F)ccc3F)nn12)N1CCC(O)CC1]

(R)—N-(6-(2-(2,5-difluorophenyl)pyrrolidin-1-yl)imidazo[1,2-b]pyridazin-3-yl)-4-hydroxypiperidine-1-carboxamide Prepared according to the method of Example 2, replacing morpholine with piperidin-4-ol to yield the final product as a solid. MS (apci) m/z=443.2 (M+H).

Example 26

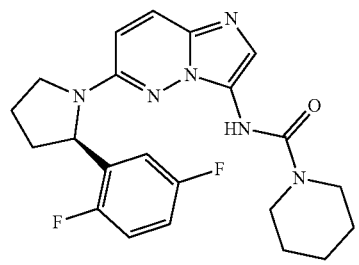 [SMILES: O=C(Nc1cnc2ccc(N3CCC[C@@H]3c3cc(F)ccc3F)nn12)N1CCCCC1]

(R)—N-(6-(2-(2,5-difluorophenyl)pyrrolidin-1-yl)imidazo[1,2-b]pyridazin-3-yl)piperidine-1-carboxamide Prepared according to the method of Example 2, replacing morpholine with piperidine, to yield the final product as a solid. MS (apci) m/z=427.2 (M+H).

Example 26A

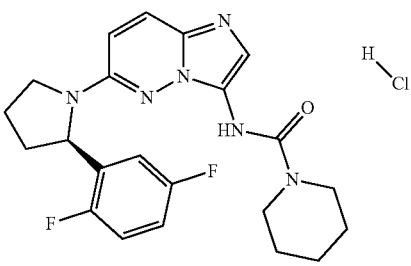 [SMILES: O=C(Nc1cnc2ccc(N3CCC[C@@H]3c3cc(F)ccc3F)nn12)N1CCCCC1 ; Cl]

(R)—N-(6-(2-(2,5-difluorophenyl)pyrrolidin-1-yl)
imidazo[1,2-b]pyridazin-3-yl)piperidine-1-carbox-
amide hydrochloride To a methanol (1 mL) solution of (R)—N-(6-(2-(2,5-difluorophenyl)pyrrolidin-1-yl)imidazo[1,2-b]pyridazin-3-yl)piperidine-1-carboxamide (4.9 mg, 0.011 mmol) was added HCl as a solution is dioxane (30 µL). After 30 minutes, the reaction was concentrated to provide (R)—N-(6-(2-(2,5-difluorophenyl)pyrrolidin-1-yl)imidazo[1,2-b]pyridazin-3-yl)piperidine-1-carboxamide hydrochloride (4.2 mg, 0.0091 mmol, 79% yield) as a yellow solid. MS (apci) m/z=427.4 (M+H).

Example 27

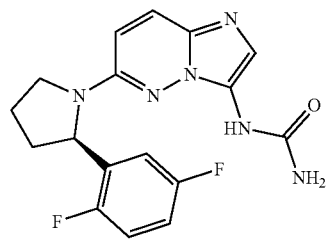 [SMILES: NC(=O)Nc1cnc2ccc(N3CCC[C@@H]3c3cc(F)ccc3F)nn12]

(R)-1-(6-(2-(2,5-difluorophenyl)pyrrolidin-1-yl)imi-
dazo[1,2-b]pyridazin-3-yl)urea Prepared according to the method of Example 2, replacing morpholine with ammonia, to yield the final product as a solid. MS (apci) m/z=359.2 (M+H).

Example 28

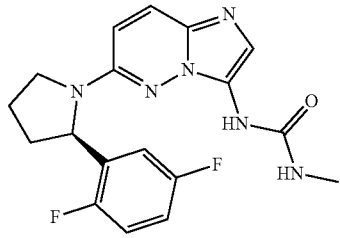 [SMILES: CNC(=O)Nc1cnc2ccc(N3CCC[C@@H]3c3cc(F)ccc3F)nn12]

(R)-1-(6-(2-(2,5-difluorophenyl)pyrrolidin-1-yl)imi-
dazo[1,2-b]pyridazin-3-yl)-3-methylurea Prepared according to the method of Example 2, replacing morpholine with methylamine, to yield the final product as a solid. MS (apci) m/z=373.2 (M+H).

Example 29

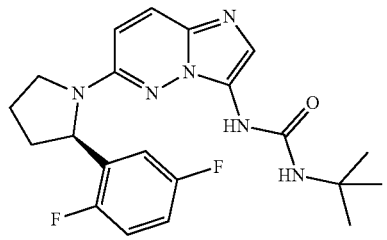 [SMILES: CC(C)(C)NC(=O)Nc1cnc2ccc(N3CCC[C@@H]3c3cc(F)ccc3F)nn12]

(R)-1-tert-butyl-3-(6-(2-(2,5-difluorophenyl)pyrroli-
din-1-yl)imidazo[1,2-b]pyridazin-3-yl)urea Prepared according to Example 5, replacing 3-cyanophenylisocyanate with 2-isocyanato-2-methylpropane, to yield the final product as a solid. MS (apci) m/z=415.2 (M+H).

Example 30

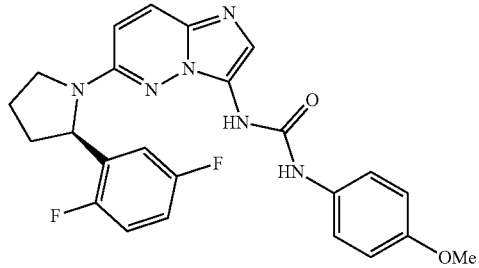 [SMILES: COc1ccc(NC(=O)Nc2cnc3ccc(N4CCC[C@@H]4c4cc(F)ccc4F)nn23)cc1]

(R)-1-(6-(2-(2,5-difluorophenyl)pyrrolidin-1-yl)imi-
dazo[1,2-b]pyridazin-3-yl)-3-(4-methoxyphenyl)urea Prepared according to Example 5, replacing 3-cyanophenylisocyanate with 1-isocyanato-4-methoxybenzene to yield the final product as a solid (7.5 mg, 85% yield). MS (apci) m/z=465.2 (M+H).

Example 31

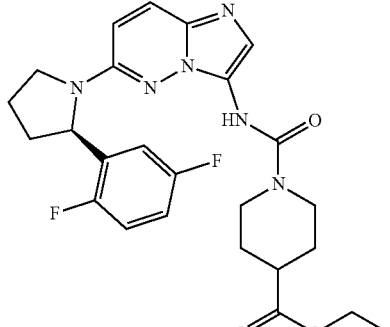

(R)-ethyl 1-(6-(2-(2,5-difluorophenyl)pyrrolidin-1-yl)imidazo[1,2-b]pyridazin-3-ylcarbamoyl)piperidine-4-carboxylate Prepared according to the method of Example 2, replacing morpholine with ethyl piperidine-4-carboxylate, to yield the final product as a solid. MS (apci) m/z=499.2 (M+H).

Example 32

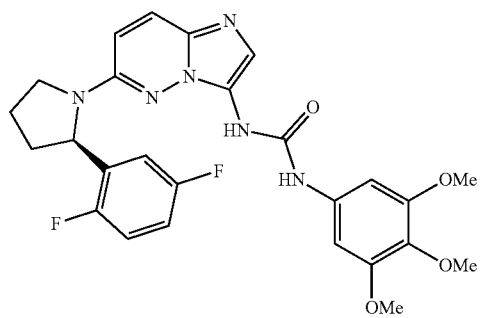 [SMILES: COc1cc(NC(=O)Nc2cnc3ccc(N4CCC[C@@H]4c4cc(F)ccc4F)nn23)cc(OC)c1OC]

(R)-1-(6-(2-(2,5-difluorophenyl)pyrrolidin-1-yl)imidazo[1,2-b]pyridazin-3-yl)-3-(3,4,5-trimethoxyphenyl)urea Prepared according to Example 5, replacing 3-cyanophenylisocyanate with 5-isocyanato-1,2,3-trimethoxybenzene to yield the final product as a solid (3.2 mg, 32% yield). MS (apci) m/z=525.2 (M+H).

Example 33

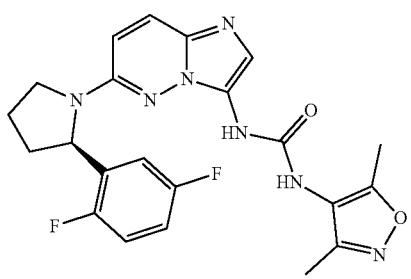 [SMILES: Cc1noc(C)c1NC(=O)Nc1cnc2ccc(N3CCC[C@@H]3c3cc(F)ccc3F)nn12]

(R)-1-(6-(2-(2,5-difluorophenyl)pyrrolidin-1-yl)imidazo[1,2-b]pyridazin-3-yl)-3-(3,5-dimethylisoxazol-4-yl)urea Prepared according to Example 5, replacing 3-cyanophenylisocyanate with 4-isocyanato-3,5-dimethylisoxazole to yield the final product as a solid (8.1 mg, 94% yield). MS (apci) m/z=454.2 (M+H).

Example 34

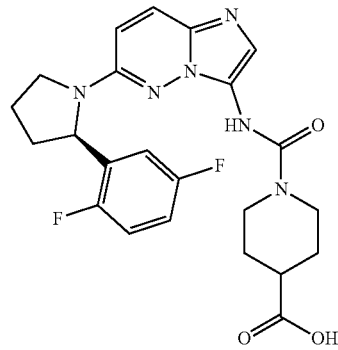 [SMILES: O=C(O)C1CCN(C(=O)Nc2cnc3ccc(N4CCC[C@@H]4c4cc(F)ccc4F)nn23)CC1]

(R)-1-(6-(2-(2,5-difluorophenyl)pyrrolidin-1-yl)imidazo[1,2-b]pyridazin-3-ylcarbamoyl)piperidine-4-carboxylic acid (R)-ethyl 1-(6-(2-(2,5-difluorophenyl)pyrrolidin-1-yl)imidazo[1,2-b]pyridazin-3-ylcarbamoyl)piperidine-4-carboxylate (Example 31, 9.2 mg, 0.018 mmol) was dissolved in a mixture solvent of THF:MeOH:water (2:2:1 v/v; 0.2 mL), followed by addition of lithium hydroxide monohydrate (2.3 mg, 0.055 mmol). After stirring at ambient temperature overnight, the reaction was diluted with water (1 mL), acidified with 10% citric acid, and extracted with EtOAc (3×1 mL). The combined organic layers were concentrated, and the crude material was purified by reverse-phase column chromatography, eluting with 5 to 55% MeOH/water to yield the final product as a solid. MS (apci) m/z=471.2 (M+H).

Example 35

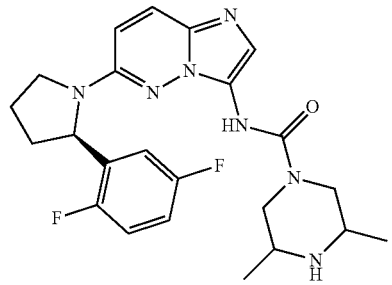 [SMILES: CC1CN(C(=O)Nc2cnc3ccc(N4CCC[C@@H]4c4cc(F)ccc4F)nn23)CC(C)N1]

N-(6-((R)-2-(2,5-difluorophenyl)pyrrolidin-1-yl)imidazo[1,2-b]pyridazin-3-yl)-3,5-dimethylpiperazine-1-carboxamide Prepared according to the method of Example 2, replacing morpholine with 2,6-dimethylpiperazine to yield the final product as a yellowish foamy powder (7.5 mg, 61% yield). MS (apci) m/z=456.2 (M+H).

Example 36

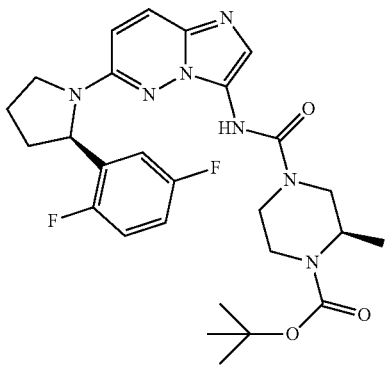 [SMILES: C[C@@H]1CN(C(=O)Nc2cnc3ccc(N4CCC[C@@H]4c4cc(F)ccc4F)nn23)CCN1C(=O)OC(C)(C)C]

(R)-tert-butyl 4-(6-((R)-2-(2,5-difluorophenyl)pyrrolidin-1-yl)imidazo[1,2-b]pyridazin-3-ylcarbamoyl)-2-methylpiperazine-1-carboxylate Prepared according to the method of Example 2, replacing morpholine with (R)-tert-butyl 2-methylpiperazine-1-carboxylate, to yield the final product as an off-white foamy powder (12 mg, 82% yield). MS (apci) m/z=542.2 (M+H).

Example 37

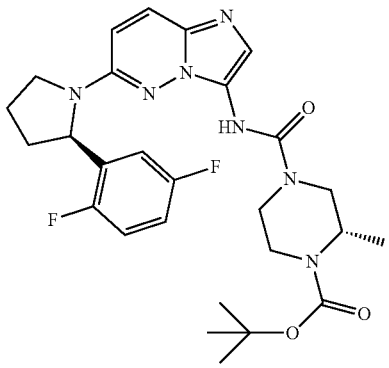 [SMILES: C[C@H]1CN(C(=O)Nc2cnc3ccc(N4CCC[C@@H]4c4cc(F)ccc4F)nn23)CCN1C(=O)OC(C)(C)C]

(S)-tert-butyl 4-(64R)-2-(2,5-difluorophenyl)pyrrolidin-1-yl)imidazo[1,2-b]pyridazin-3-ylcarbamoyl)-2-methylpiperazine-1-carboxylate Prepared according to the method of Example 2, replacing morpholine with (S)-tert-butyl 2-methylpiperazine-1-carboxylate to yield the desired product as an off-white foamy powder (10 mg, 69% yield). MS (apci) m/z=542.2 (M+H).

Example 38

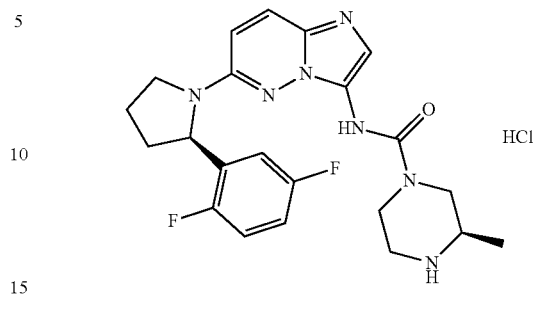

(R)—N-(6-((R)-2-(2,5-difluorophenyl)pyrrolidin-1-yl)imidazo[1,2-b]pyridazin-3-yl)-3-methylpiperazine-1-carboxamide hydrochloride To a reaction vial containing (R)-tert-butyl 4-(6-((R)-2-(2,5-difluorophenyl)pyrrolidin-1-yl)imidazo[1,2-b]pyridazin-3-ylcarbamoyl)-2-methylpiperazine-1-carboxylate (Example 36; 12 mg, 0.022 mmol) was added 0.5 mL 4 N HCl (dioxane) solution in one portion. After stirring at ambient temperature for 4 hours, the reaction was concentrated. The resulting solid residue was treated with ether and concentrated again to yield the final product salt form as a pale-yellowish powder. MS (apci) m/z=442.2 (M+H).

Example 39

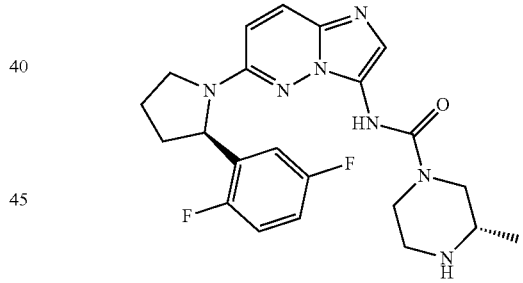

S)—N-(6-((R)-2-(2,5-difluorophenyl)pyrrolidin-1-yl)imidazo[1,2-b]pyridazin-3-yl)-3-methylpiperazine-1-carboxamide Prepared according to the method of Example 38, replacing (R)-tert-butyl 4-(6-((R)-2-(2,5-difluorophenyl)pyrrolidin-1-yl)imidazo[1,2-b]pyridazin-3-ylcarbamoyl)-2-methylpiperazine-1-carboxylate with (S)-tert-butyl 4-(6-((R)-2-(2,5-difluorophenyl) pyrrolidin-1-yl)imidazo[1,2-b] pyridazin-3-ylcarbamoyl)-2-methylpiperazine-1-carboxylate (Example 37). The final product was a fine pale-yellowish powder. MS (apci) m/z=442.2 (M+H).

Example 40

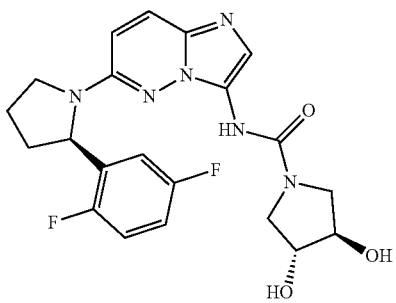 [SMILES: O=C(Nc1cnc2ccc(N3CCC[C@@H]3c3cc(F)ccc3F)nn12)N1C[C@@H](O)[C@H](O)C1]

(3R,4R)—N-(6-((R)-2-(2,5-difluorophenyl)pyrrolidin-1-yl)imidazo[1,2-b]pyridazin-3-yl)-3,4-dihydroxypyrrolidine-1-carboxamide Prepared according to the method of Example 2, replacing morpholine with (3R,4R)-pyrrolidine-3,4-diol [obtained from benzyl de-protection of commercially available (3R,4R)-1-benzylpyrrolidine-3,4-diol] to yield the final product as a solid (11 mg, 92% yield). MS (apci) m/z=445.2 (M+H).

Example 41

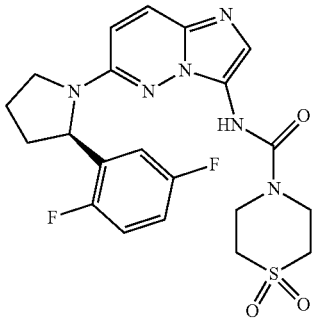 [SMILES: O=C(Nc1cnc2ccc(N3CCC[C@@H]3c3cc(F)ccc3F)nn12)N1CCS(=O)(=O)CC1]

(R)-1-(6-(2-(2,5-difluorophenyl)pyrrolidin-1-yl)imidazo[1,2-b]pyridazin-3-ylcarbamoyl)piperidin-4-sulfone Prepared according to the method of Example 2, replacing morpholine with piperidin-4-sulfone to yield the final product as a solid (10 mg, 78% yield). MS (apci) m/z=477.2 (M+H).

Example 42

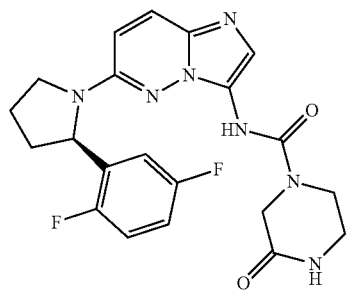 [SMILES: O=C1CN(C(=O)Nc2cnc3ccc(N4CCC[C@@H]4c4cc(F)ccc4F)nn23)CCN1]

(R)—N-(6-(2-(2,5-difluorophenyl)pyrrolidin-1-yl)imidazo[1,2-b]pyridazin-3-yl)-3-oxopiperazine-1-carboxamide Prepared according to the method of Example 2, replacing morpholine with piperazin-2-one to yield the final product as a solid (10 mg, 84% yield). MS (apci) m/z=442.1 (M+H).

Example 43

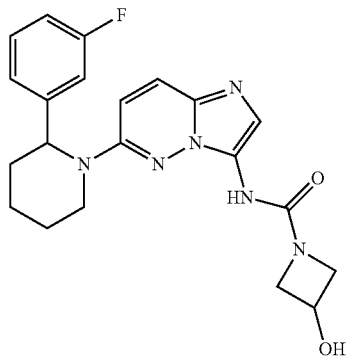 [SMILES: O=C(Nc1cnc2ccc(N3CCCCC3c3cccc(F)c3)nn12)N1CC(O)C1]

N-(6-(2-(3-fluorophenyl)piperidin-1-yl)imidazo[1,2-b]pyridazin-3-yl)-3-hydroxyazetidine-1-carboxamide Step 1: Preparation of 6-(2-(3-fluorophenyl)piperidin-1-yl)-3-nitroimidazo[1,2-b]pyridazine To a pressure reaction tube were charged 6-chloro-3-nitroimidazo[1,2-b]pyridazine (450 mg, 2.27 mmol), 2-(3-fluorophenyl)piperidine (609 mg, 3.40 mmol, purchased from ChemBridge), and N-ethyl-N-isopropylpropan-2-amine (0.51 mL, 2.95 mmol), followed by addition of 1.0 mL n-butanol. The reaction mixture was then sealed and stirred at 180° C. for 24 hours. After completion, the reaction was cooled to ambient temperature, and diluted with water and EtOAc. The organic layer was separated, and the aqueous layer was extracted with EtOAc twice. The combined organic layers was dried over Na$_2$SO$_4$ and concentrated. The crude product was purified by silica column chromatography, eluting with 20 to 50% EtOAc in hexanes to yield the desired product for the next step.

Step 2: Preparation of 6-(2-(3-fluorophenyl)piperidin-1-yl)imidazo[1,2-b]pyridazin-3-amine A mixture of 6-(2-(3-fluorophenyl)piperidin-1-yl)-3-nitroimidazo[1,2-b]pyridazine (50 mg, 0.146 mmol) and SnCl$_2$ dihydrate (165 mg, 0.732 mmol) in 5 mL EtOH was first stirred at 70° C. for 30 minutes, then cooled to ambient temperature and concentrated. EtOAc and water (10 mL each) were added to the solid residue, followed by Na$_2$CO$_3$ aqueous solution (2 mL×2 N) to obtain a phase break. The organic layer was separated, and the aqueous layer was extracted with EtOAc (3×10 mL). The combined organic layers was dried with Na$_2$SO$_4$ and concentrated to provide the product for the next step.

Step 3: Preparation of N-(6-(2-(3-fluorophenyl)piperidin-1-yl)imidazo[1,2-b]pyridazin-3-yl)-3-hydroxyazetidine-1-carboxamide To a DCM (2 mL) solution of 6-(2-(3-fluorophenyl)piperidin-1-yl)imidazo[1,2-b]pyridazin-3-amine (45 mg, 0.14 mmol) was added CDI (35 mg, 0.22 mmol) at ambient temperature in one portion. After stirring for five hours, azetidin-3-ol hydrochloride (54 mg, 0.33 mmol) was added in one portion, followed by DIEA (0.05 mL, 0.29 mmol), and the reaction was stirred at ambient temperature overnight. The reaction was diluted with DCM, washed with water, dried over Na$_2$SO$_4$ and concentrated. The crude product was purified by reversed phase column, eluting with 0 to 55% CH$_3$CN/water to obtain the desired product as a solid (30 mg, 51% yield). MS (apci) m/z=411.2 (M+H).

Example 44

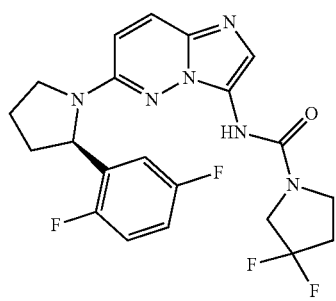 [SMILES: O=C(Nc1cnc2ccc(N3CCC[C@@H]3c3cc(F)ccc3F)nn12)N1CCC(F)(F)C1]

(R)—N-(6-(2-(2,5-difluorophenyl)pyrrolidin-1-yl)imidazo[1,2-b]pyridazin-3-yl)-3,3-difluoropyrrolidine-1-carboxamide Prepared according to Example 13, replacing azetidin-3-ol hydrochloride with 3,3-difluoropyrrolidine hydrochloride to yield the final product as a white solid. MS (apci) m/z=449.2 (M+H).

Example 45

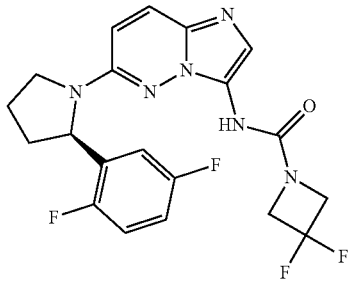 [SMILES: O=C(Nc1cnc2ccc(N3CCC[C@@H]3c3cc(F)ccc3F)nn12)N1CC(F)(F)C1]

(R)—N-(6-(2-(2,5-difluorophenyl)pyrrolidin-1-yl)imidazo[1,2-b]pyridazin-3-yl)-3,3-difluoroazetidine-1-carboxamide Prepared according to Example 13, replacing azetidin-3-ol hydrochloride with 3,3-difluoroazetidine hydrochloride to yield the final product as a solid (20 mg, 77% yield). MS (apci) m/z=435.2 (M+H).

Example 46

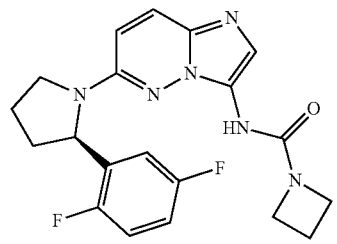 [SMILES: O=C(Nc1cnc2ccc(N3CCC[C@@H]3c3cc(F)ccc3F)nn12)N1CCC1]

(R)—N-(6-(2-(2,5-difluorophenyl)pyrrolidin-1-yl)imidazo[1,2-b]pyridazin-3-yl)azetidine-1-carboxamide Prepared according to Example 13, replacing azetidin-3-ol hydrochloride with azetidine to yield the final product as a solid (20 mg, 77% yield). MS (apci) m/z=399.2 (M+H).

Example 47

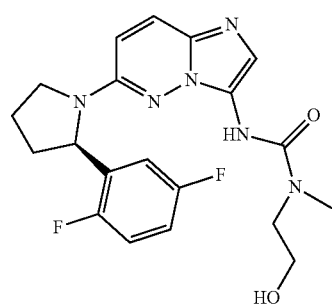 [SMILES: CN(CCO)C(=O)Nc1cnc2ccc(N3CCC[C@@H]3c3cc(F)ccc3F)nn12]

(R)-3-(6-(2-(2,5-difluorophenyl)pyrrolidin-1-yl)imidazo[1,2-b]pyridazin-3-yl)-1-(2-hydroxyethyl)-1-methylurea Prepared according to Example 13, replacing azetidin-3-ol hydrochloride with 2-(methylamino)ethanol to yield the final product as a solid (20 mg, 81% yield). MS (apci) m/z=417.2 (M+H).

Example 48

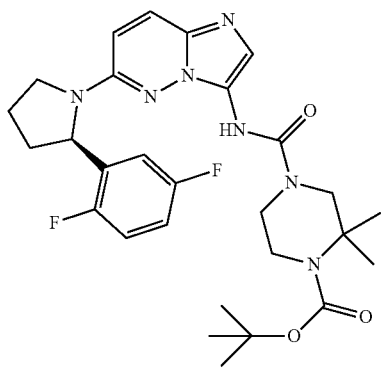 [SMILES: CC(C)(C)OC(=O)N1CCN(C(=O)Nc2cnc3ccc(N4CCC[C@@H]4c4cc(F)ccc4F)nn23)CC1(C)C]

(R)-tert-butyl 4-(6-(2-(2,5-difluorophenyl)pyrrolidin-1-yl)imidazo[1,2-b]pyridazin-3-ylcarbamoyl)-2,2-dimethylpiperazine-1-carboxylate Prepared according to the method of Example 2, replacing morpholine with tert-butyl 2,2-dimethylpiperazine-1-carboxylate to yield the final product as a solid (40 mg, 91% yield). MS (apci) m/z=556.3 (M+H).

Example 49

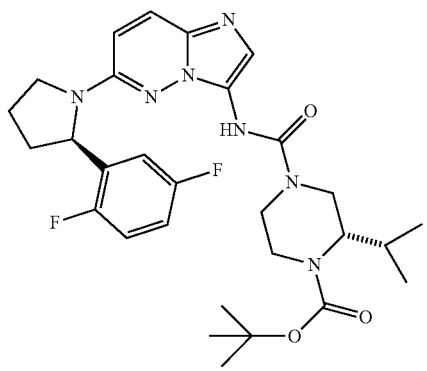 [SMILES: CC(C)[C@H]1CN(C(=O)Nc2cnc3ccc(N4CCC[C@@H]4c4cc(F)ccc4F)nn23)CCN1C(=O)OC(C)(C)C]

(S)-tert-butyl 4-(6-((R)-2-(2,5-difluorophenyl)pyrrolidin-1-yl)imidazo[1,2-b]pyridazin-3-ylcarbamoyl)-2-isopropylpiperazine-1-carboxylate Prepared according to the method of Example 2, replacing morpholine with (S)-tert-butyl 2-isopropylpiperazine-1-carboxylate to yield the final product as a white foamy solid (42 mg, 93% yield). MS (apci) m/z=570.3 (M+H).

Example 50

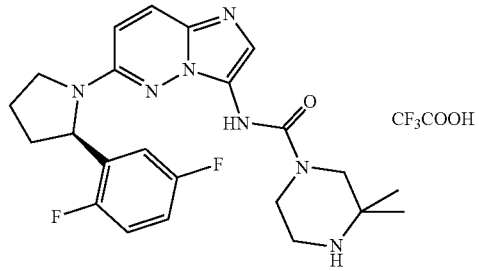 [SMILES: CC1(C)CN(C(=O)Nc2cnc3ccc(N4CCC[C@@H]4c4cc(F)ccc4F)nn23)CCN1 ; "CF3COOH"]

(R)—N-(6-(2-(2,5-difluorophenyl)pyrrolidin-1-yl)imidazo[1,2-b]pyridazin-3-yl)-3,3-dimethylpiperazine-1-carboxamide trifluoroacetate To a reaction vial containing (R)-tort-butyl 4-(6-(2-(2,5-difluorophenyl)pyrrolidin-1-yl)imidazo[1,2-b]pyridazin-3-ylcarbamoyl)-2,2-dimethylpiperazine-1-carboxylate (Example 48, 33.5 mg, 0.06 mmol) was added 1 mL TFA/DCM (1:1 v/v) and left at ambient temperature for 1 hour. After removal of solvent, the crude oil was treated with ether and gave the product TFA salt as a white solid. MS (apci) m/z=456.2 (M+H).

Example 51

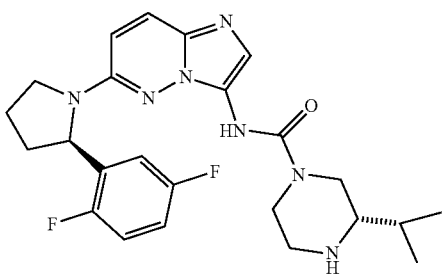 [SMILES: CC(C)[C@H]1CN(C(=O)Nc2cnc3ccc(N4CCC[C@@H]4c4cc(F)ccc4F)nn23)CCN1]

(S)—N-(6-((R)-2-(2,5-difluorophenyl)pyrrolidin-1-yl)imidazo[1,2-b]pyridazin-3-yl)-3-isopropylpiperazine-1-carboxamide Prepared according to the method of Example 50, replacing (R)-tert-butyl 4-(6-(2-(2,5-difluorophenyl)pyrrolidin-1-yl)imidazo[1,2-b]pyridazin-3-ylcarbamoyl)-2,2-dimethylpiperazine-1-carboxylate with (S)-tert-butyl 4-(6-((R)-2-(2,5-difluorophenyl)pyrrolidin-1-yl)imidazo[1,2-b]pyridazin-3-ylcarbamoyl)-2-isopropylpiperazine-1-carboxylate (Example 49). The final product was a fine white solid. MS (apci) m/z=470.2 (M+H).

Example 52

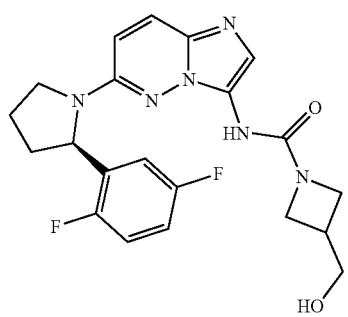

(R)—N-(6-(2-(2,5-difluorophenyl)pyrrolidin-1-yl)imidazo[1,2-b]pyridazin-3-yl)-3-(hydroxymethyl)azetidine-1-carboxamide Prepared according to Example 13, replacing azetidin-3-ol hydrochloride with azetidin-3-ylmethanol hydrochloride to yield the final product as a pale-yellowish solid (18 mg, 53% yield). MS (apci) m/z=429.2 (M+H).

Example 52A

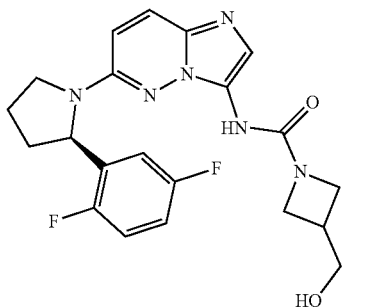 [SMILES: O=C(Nc1cnc2ccc(N3CCC[C@@H]3c3cc(F)ccc3F)nn12)N1CC(CO)C1]

(R)—N-(6-(2-(2,5-difluorophenyl)pyrrolidin-1-yl)imidazo[1,2-b]pyridazin-3-yl)-3-(hydroxymethyl)azetidine-1-carboxamide hydrochloride To a methanol (1 mL) solution of (R)—N-(6-(2-(2,5-difluorophenyl)pyrrolidin-1-yl)imidazo[1,2-b]pyridazin-3-yl)-3-(hydroxymethyl)azetidine-1-carboxamide (9.9 mg, 0.0231 mmol) was added HCl as a solution is dioxane (30 µL). After 30 minutes, the reaction was concentrated to provide (R)—N-(6-(2-(2,5-difluorophenyl)pyrrolidin-1-yl)imidazo[1,2-b]pyridazin-3-yl)-3-(hydroxymethyl)azetidine-1-carboxamide hydrochloride (10.2 mg, 0.0219 mmol, 94.9% yield) as a yellow solid. MS (apci) m/z=429.4 (M+H).

Example 53

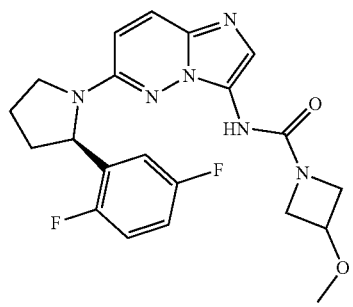 [SMILES: COC1CN(C(=O)Nc2cnc3ccc(N4CCC[C@@H]4c4cc(F)ccc4F)nn23)C1]

(R)—N-(6-(2-(2,5-difluorophenyl)pyrrolidin-1-yl)imidazo[1,2-b]pyridazin-3-yl)-3-methoxyazetidine-1-carboxamide Prepared according to Example 13, replacing azetidin-3-ol hydrochloride with 3-methoxyazetidine hydrochloride to yield the final product as a pale-yellowish solid (60 mg, 88% yield). MS (apci) m/z=429.2 (M+H).

Example 54

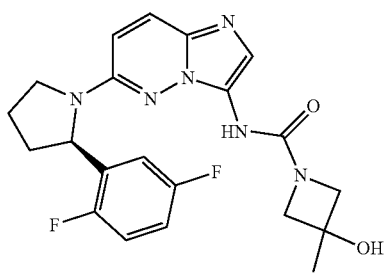 [SMILES: CC1(O)CN(C(=O)Nc2cnc3ccc(N4CCC[C@@H]4c4cc(F)ccc4F)nn23)C1]

(R)—N-(6-(2-(2,5-difluorophenyl)pyrrolidin-1-yl)imidazo[1,2-b]pyridazin-3-yl)-3-hydroxy-3-methyl-azetidine-1-carboxamide Prepared according to Example 13, replacing azetidin-3-ol hydrochloride with 3-methylazetidin-3-ol hydrochloride to yield the final product as a pale-yellowish solid (63 mg, 93% yield). MS (apci) m/z=429.2 (M+H).

Example 54A

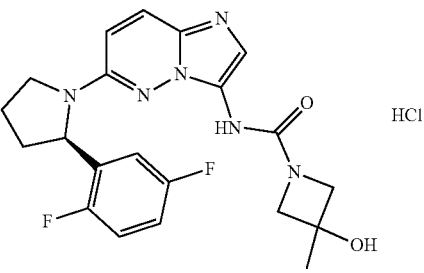 [SMILES: CC1(O)CN(C(=O)Nc2cnc3ccc(N4CCC[C@@H]4c4cc(F)ccc4F)nn23)C1 ; Cl]

(R)—N-(6-(2-(2,5-difluorophenyl)pyrrolidin-1-yl)imidazo[1,2-b]pyridazin-3-yl)-3-hydroxy-3-methylazetidine-1-carboxamide hydrochloride To a methanol (1 mL) solution of (R)—N-(5-(2-(2,5-difluorophenyl)pyrrolidin-1-yl)pyrazolo[1,5-a]pyrimidin-3-yl)-3-hydroxy-3-methylazetidine-1-carboxamide (10.2 mg, 0.0238 mmol) was added HCl as a solution is dioxane (30 µL). After 30 minutes, the reaction was concentrated to provide (R)—N-(5-(2-(2,5-difluorophenyl)pyrrolidin-1-yl)pyrazolo[1,5-a]pyrimidin-3-yl)-3-hydroxy-3-methylazetidine-1-carboxamide hydrochloride (8.3 mg, 0.0179 mmol, 75.0% yield) as a yellow solid.

Example 55

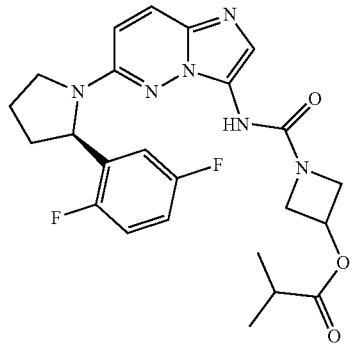 [SMILES: CC(C)C(=O)OC1CN(C(=O)Nc2cnc3ccc(N4CCC[C@@H]4c4cc(F)ccc4F)nn23)C1]

(R)-1-(6-(2-(2,5-difluorophenyl)pyrrolidin-1-yl)imidazo[1,2-b]pyridazin-3-ylcarbamoyl)azetidin-3-yl isobutyrate (R)—N-(6-(2-(2,5-difluorophenyl)pyrrolidin-1-yl)imidazo[1,2-b]pyridazin-3-yl)-3-hydroxyazetidine-1-carboxamide (Example 13; 21.5 mg, 0.05 mmol) was first dissolved in 0.5 mL DMF, followed by addition of isobutyric anhydride (24 mg, 0.15 mmol) and a few drops of DIEA. After overnight stirring at ambient temperature, the crude material was concentrated and directly purified by silica chromatography, eluting with 3 to 8% MeOH in DCM to provide the final product as a beige foamy solid (12 mg, 50% yield). MS (apci) m/z=485.2 (M+H).

Example 56

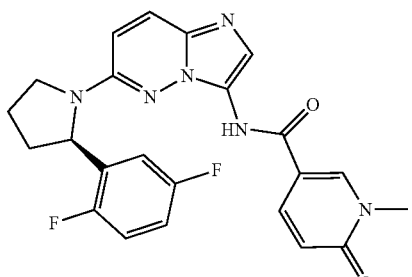

(R)—N-(6-(2-(2,5-difluorophenyl)pyrrolidin-1-yl)imidazo[1,2-b]pyridazin-3-yl)-1-methyl-6-oxo-1,6-dihydropyridine-3-carboxamide Prepared according to Example 4, replacing 4-(methylsulfonamido)benzoic acid with 1-methyl-6-oxo-1,6-dihydropyridine-3-carboxylic acid to yield the final product as a yellowish solid (16 mg, 37% yield). MS (apci) m/z=451.2 (M+H).

Example 57

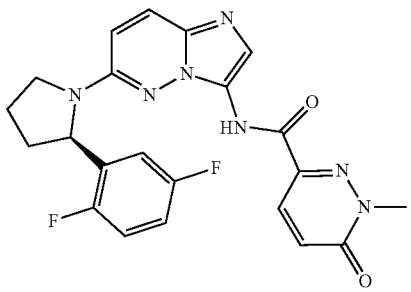 [SMILES: Cn1nc(C(=O)Nc2cnc3ccc(N4CCC[C@@H]4c4cc(F)ccc4F)nn23)ccc1=O]

(R)—N-(6-(2-(2,5-difluorophenyl)pyrrolidin-1-yl)imidazo[1,2-b]pyridazin-3-yl)-1-methyl-6-oxo-1,6-dihydropyridazine-3-carboxamide Prepared according to Example 4, replacing 4-(methylsulfonamido)benzoic acid with 1-methyl-6-oxo-1,6-dihydropyridazine-3-carboxylic acid. The resulting light yellowish heavy suspension was vacuum-filtered, and the solid was rinsed with acetonitrile and ether, giving the first batch of pure product as a yellow powder (52 mg). A second batch of product was obtained through treating the concentrated filtrate from above with reverse-phase chromatography, eluting with 5 to 60% acetonitrile/water (total product from combining two batches: 65 mg, 91% yield). MS (apci) m/z=452.3 (M+H).

Example 58

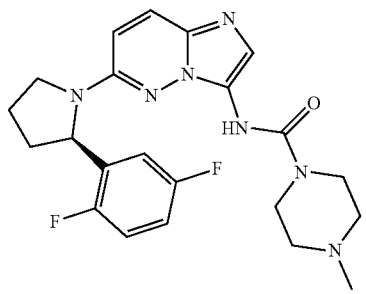 [SMILES: CN1CCN(C(=O)Nc2cnc3ccc(N4CCC[C@@H]4c4cc(F)ccc4F)nn23)CC1]

(R)—N-(6-(2-(2,5-difluorophenyl)pyrrolidin-1-yl)imidazo[1,2-b]pyridazin-3-yl)-4-methylpiperazine-1-carboxamide Prepared according to the method of Example 2, replacing morpholine with 1-methylpiperazine, to yield the final product as a pale-yellowish foamy solid (4.5 mg, 63% yield). MS (apci) m/z=442.1 (M+H).

Example 59

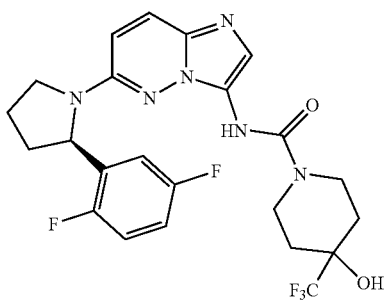 [SMILES: O=C(Nc1cnc2ccc(N3CCC[C@@H]3c3cc(F)ccc3F)nn12)N1CCC(O)(C(F)(F)F)CC1]

(R)—N-(6-(2-(2,5-difluorophenyl)pyrrolidin-1-yl)
imidazo[1,2-b]pyridazin-3-yl)-4-hydroxy-4-(trifluoromethyl)piperidine-1-carboxamide Prepared according to Example 13, replacing azetidin-3-ol hydrochloride with 4-(trifluoromethyl)piperidin-4-ol, to yield the final product as a pale-yellowish solid (35 mg, 86% yield). MS (apci) m/z=511.2 (M+H).

Example 60

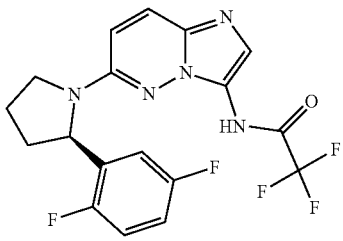 [SMILES: O=C(Nc1cnc2ccc(N3CCC[C@@H]3c3cc(F)ccc3F)nn12)C(F)(F)F]

(R)—N-(6-(2-(2,5-difluorophenyl)pyrrolidin-1-yl)
imidazo[1,2-b]pyridazin-3-yl)-2,2,2-trifluoroacetamide A DCM (1 mL) solution of (R)-6-(2-(2,5-difluorophenyl)pyrrolidin-1-yl)imidazo[1,2-b]pyridazin-3-amine (Preparation B; 50 mg, 0.16 mmol) was cooled in an ice bath, followed by addition of 2,2,2-trifluoroacetic anhydride (24 μl, 0.17 mmol) and pyridine (14 μl, 0.17 mmol) drop-wise. The ice bath was removed after reagent addition and the reaction was warmed to ambient temperature. After stirring for one hour, the reaction was concentrated and directly purified by reverse-phase column chromatography, eluting with 5 to 70% acetonitrile/water to yield the final product as an off-white powder (45 mg, 69% yield). MS (apci) m/z=412.3 (M+H).

What is claimed is:
1. A method for attenuating or ameliorating one or more symptoms of a solid tumor exhibiting one or more of overexpression, activation, amplification, and mutation of a Trk kinase in a mammal in need thereof, the method comprising:
   (a) detecting a tumor in a mammal that exhibits one or more of overexpression, activation, amplification, and mutation of a Trk kinase; and
   (b) administering to the mammal a therapeutically effective amount of a compound having the general formula I

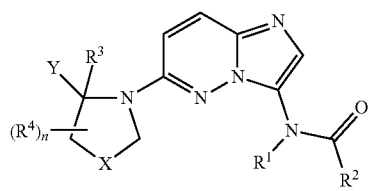

or a pharmaceutically acceptable salt thereof, wherein:
$R^1$ is H or (1-6C alkyl);
$R^2$ is $NR^bR^c$, (1-4C)alkyl, (1-4C)fluoroalkyl, $CF_3$, (1-4C) hydroxyalkyl, -(1-4C alkyl)hetAr$^1$, -(1-4C alkyl)NH(1-4C alkyl), hetAr$^2$, hetCyc$^1$, hetCyc$^2$, phenyl which is optionally substituted with $NHSO_2$(1-4C alkyl), or (3-6C)cycloalkyl which is optionally substituted with (1-4C alkyl), CN, OH, $CF_3$, $CO_2$(1-4C alkyl) or $CO_2H$;
$R^b$ is H or (1-6C alkyl);
$R^c$ is H, (1-4C)alkyl, (1-4C)hydroxyalkyl, hetAr$^3$, or phenyl, wherein said phenyl is optionally substituted with one or more substituents independently selected from halogen, CN, $CF_3$ and —O(1-4C alkyl),
or $NR^bR^c$ forms a 4 membered heterocyclic ring having a ring nitrogen atom, wherein said heterocyclic ring is optionally substituted with one or more substituents independently selected from halogen, OH, (1-4C alkyl), (1-4 C)alkoxy, —OC(=O)(1-4C alkyl), $NH_2$, —NHC(=O)O(1-4C alkyl), and (1-4C)hydroxyalkyl,
or $NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, NHC(=O)O(1-4C alkyl) and oxo,
or $NR^bR^c$ forms a 7-8 membered bridged heterocyclic ring having 1-2 ring nitrogen atoms and optionally substituted with $CO_2$(1-4C alkyl);
hetAr$^1$ is a 5-membered heteroaryl ring having 1-3 ring nitrogen atoms;
hetAr$^2$ is 5-6 membered heteroaryl ring having at least one nitrogen ring atom and optionally having a second ring heteroatom independently selected from N and S, wherein said heteroaryl ring is optionally substituted with one or more substituents independently selected from (1-4C alkyl), halogen, -(1-4 C)alkoxy, and NH(1-4C alkyl);
hetCyc$^1$ is a carbon-linked 4-6 membered azacyclic ring optionally substituted with one or more substituents independently selected from (1-4C alkyl), $CO_2H$ and $CO_2$(1-4C alkyl);
hetCyc$^2$ is a pyridinone or pyridazinone ring substituted with a substituent selected from (1-4C)alkyl;
hetAr$^3$ is a 5-6 membered heteroaryl ring having 1-2 ring heteroatoms independently selected from N and O and optionally substituted with one or more substituents independently selected from (1-4C)alkyl;
Y is a phenyl ring optionally substituted with one or more substituents independently selected from halogen, (1-4C)alkoxy, CF$_3$ and CHF$_2$, or a 5-6 membered heteroaryl ring having a ring heteroatom selected from N and S;
X is null, —CH$_2$—, CH$_2$CH$_2$—, —CH$_2$O—, or —CH$_2$NR$^d$—;
R$^d$ is H or (1-4C alkyl);
R$^3$ is H or (1-4C alkyl);
each R$^4$ is independently selected from halogen, (1-4C) alkyl, OH, (1-4 C)alkoxy, NH$_2$, NH(1-4C alkyl) and CH$_2$OH; and
n is 0, 1, 2, 3, 4, 5 or 6.

2. The method of claim 1, wherein the solid tumor is selected from the group consisting of: breast, prostate, lung, renal, thyroid, neuroblastoma, ovarian cancer, breast cancer, pancreatic cancer, astrocytoma and medulloblastoma, glioma, melanoma, lung adenocarcinoma, large cell neuroendocrine tumors, colorectal cancer, stomach, bladder, uterus, rectum, and kidney.

3. The method of claim 1, wherein R$^2$ is NR$^b$R$^c$.

4. The method of claim 1, wherein:
NR$^b$R$^c$ forms a 4 membered heterocyclic ring having a ring nitrogen atom optionally substituted with one or more substituents independently selected from halogen, OH, (1-4C alkyl), (1-4 C)alkoxy, —OC(═O)(1-4C alkyl), NH$_2$, —NHC(═O)O(1-4C alkyl), and (1-4C)hydroxyalkyl,
or NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(═O)O(1-4C alkyl) and oxo,
or NR$^b$R$^c$ forms a 7-8 membered bridged heterocyclic ring having 1-2 ring nitrogen atoms and optionally substituted with CO$_2$(1-4C alkyl).

5. The method of claim 1, wherein:
R$^b$ is H or (1-6C alkyl); and
R$^c$ is H, (1-4C)alkyl, (1-4C)hydroxyalkyl, hetAr$^3$, or phenyl, wherein said phenyl is optionally substituted with one or more substituents independently selected from halogen, CN, CF$_3$ and —O(1-4C alkyl).

6. The method of claim 1, wherein R$^2$ is (1-4C)alkyl, (1-4C)fluoroalkyl, CF$_3$, -(1-4C alkyl)hetAr$^1$, or -(1-4C alkyl)NH(1-4C alkyl).

7. The method of claim 1, wherein X is null, —CH$_2$— or CH$_2$CH$_2$—.

8. The method of claim 1, wherein Y is a phenyl ring optionally substituted with one or more substituents independently selected from halogen, (1-4C)alkoxy, CF$_3$ and CHF$_2$.

9. The method of claim 1, wherein Y has the absolute configuration of Figure Ia:

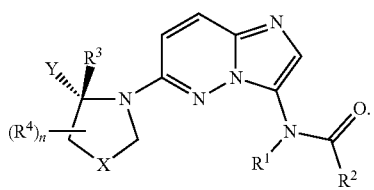

10. The method of claim 1, wherein R$^3$ is H.

11. The method of claim 1, wherein:
R$^1$ is H or (1-6C alkyl);
R$^2$ is NR$^b$R$^c$;
NR$^b$R$^c$ forms a 4 membered heterocyclic ring having a ring nitrogen atom, wherein said heterocyclic ring is optionally substituted with one or more substituents independently selected from halogen, OH, (1-4C alkyl), (1-4 C)alkoxy, —OC(═O)(1-4C alkyl), NH$_2$, —NHC(═O)O(1-4C alkyl) and (1-4C)hydroxyalkyl,
or NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(═O)O(1-4C alkyl) and oxo;
Y is phenyl optionally substituted with one or more substituents independently selected from halogen, (1-4C)alkoxy, CF$_3$ and CHF$_2$;
X is null, —CH$_2$—, or —CH$_2$CH$_2$—;
R$^3$ is H or (1-4C alkyl);
each R$^4$ is independently selected from halogen, (1-4C) alkyl, OH, (1-4 C)alkoxy, NH$_2$, NH(1-4C alkyl) and CH$_2$OH; and
n is 0, 1, or 2.

12. The method of claim 11, wherein:
R$^1$ is H or (1-6C alkyl);
R$^2$ is NR$^b$R$^c$;
NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(═O)O(1-4C alkyl) and oxo;
Y is phenyl optionally substituted with one or more substituents independently selected from halogen, (1-4C)alkoxy, CF$_3$ and CHF$_2$;
X is —CH$_2$—;
R$^3$ is H or (1-4C alkyl);
each R$^4$ is independently selected from halogen, (1-4C) alkyl, OH, (1-4 C)alkoxy, NH$_2$, NH(1-4C alkyl) and CH$_2$OH; and
n is 0, 1, or 2.

13. The method of claim 12, wherein the heterocyclic ring formed by NR$^b$R$^c$ is optionally substituted with one or two substituents independently selected from OH, F, NH$_2$, CO$_2$H, CO$_2$Et, NHCO$_2$C(CH$_3$)$_3$, CF$_3$, methyl, ethyl, isopropyl, CO$_2$C(CH$_3$)$_3$ and oxo.

14. The method of claim 13, wherein Y is phenyl optionally substituted with one or more halogen atoms.

15. The method of claim 14, wherein Y is phenyl optionally substituted with one or two fluorine atoms.

16. The method of claim 11, wherein
R$^1$ is H or (1-6C alkyl);
R$^2$ is NR$^b$R$^c$;
NR$^b$R$^c$ forms a 4 membered heterocyclic ring having a ring nitrogen atom, wherein said ring is optionally substituted with one or more substituents independently selected from halogen, OH, (1-4C alkyl), (1-4 C)alkoxy, —OC(═O)(1-4C alkyl), NH$_2$, —NHC(═O)O(1-4C alkyl) and (1-4C)hydroxyalkyl;

Y is phenyl optionally substituted with one or more substituents independently selected from halogen, (1-4C)alkoxy, $CF_3$ and $CHF_2$;

X is $-CH_2-$;

$R^3$ is H or (1-4C alkyl);

each $R^4$ is independently selected from halogen, (1-4C) alkyl, OH, (1-4 C)alkoxy, $NH_2$, NH(1-4C alkyl) and $CH_2OH$; and n is 0, 1, or 2.

17. The method of claim 16, wherein the heterocyclic ring formed by $NR^bR^c$ is optionally substituted with one or two substituents independently selected from F, OH, methyl, OMe, $OC(=O)C(CH_3)_2$, $NH_2$, $—NHC(=O)OC(CH_3)_3$ and $CH_2OH$.

18. The method of claim 17, wherein Y is phenyl optionally substituted with one or more halogen atoms.

19. The method of claim 18, wherein Y is phenyl optionally substituted with one or two fluorine atoms.

20. The method of claim 11, wherein n is zero or one.

21. The method of claim 20, wherein $R^3$ is hydrogen.

22. The method of claim 21, wherein $R^1$ is hydrogen.

* * * * *